US011890002B2

(12) United States Patent
Patel et al.

(10) Patent No.: US 11,890,002 B2
(45) Date of Patent: Feb. 6, 2024

(54) KNOTLESS ANCHOR INSERTION

(71) Applicant: Medos International Sarl, LeLocle (CH)

(72) Inventors: Ravi Patel, Providence, RI (US); Daniel Gamache, Dedham, MA (US); Brian H. Otrando, Raynham, MA (US); Timothy Reppert, Foster City, CA (US); Mark Shainwald, Raynham, MA (US); Jordan Jacobs, Raynham, MA (US)

(73) Assignee: Medos International Sarl, Le Locle (CH)

( * ) Notice: Subject to any disclaimer, the term of this patent is extended or adjusted under 35 U.S.C. 154(b) by 145 days.

(21) Appl. No.: 17/241,296

(22) Filed: Apr. 27, 2021

(65) Prior Publication Data
US 2021/0338223 A1 Nov. 4, 2021

Related U.S. Application Data

(60) Provisional application No. 63/017,009, filed on Apr. 29, 2020.

(51) Int. Cl.
*A61B 17/04* (2006.01)
*A61B 17/00* (2006.01)
(Continued)

(52) U.S. Cl.
CPC .... *A61B 17/0401* (2013.01); *A61B 2017/042* (2013.01); *A61B 2017/0409* (2013.01);
(Continued)

(58) Field of Classification Search
CPC ............ A61B 17/0401; A61B 17/0642; A61B 2017/0409; A61B 2017/0445;
(Continued)

(56) References Cited

U.S. PATENT DOCUMENTS

| 5,092,870 A | 3/1992 | Mittermeier |
| 5,171,314 A | 12/1992 | Dulebohn |

(Continued)

FOREIGN PATENT DOCUMENTS

| EP | 2422712 A2 | 2/2012 |
| EP | 3069663 A1 | 9/2016 |

(Continued)

OTHER PUBLICATIONS

Harvey Tool, "Thread Milling Cutters—Multi-Form—N.P.T. Threads," dated no later than Apr. 10, 2021, available at <https://www.harveytool.com/products/thread-milling-cutters---multi-form---n.p.t.-threads> (2 pages).

(Continued)

*Primary Examiner* — Kelly J Bekker
*Assistant Examiner* — Lindsey R. Rivers

(57) ABSTRACT

Various exemplary systems and devices for knotless anchor insertion and methods of knotless anchor insertion are provided. In general, an inserter tool is configured for knotless anchor insertion in a soft tissue repair surgical procedure. The inserter tool is configured to insert an anchor into a bone of a patient to secure a soft tissue relative to the bone. A suture coupled to the soft tissue is secured relative to the bone by being trapped between an exterior surface of the anchor and a bone surface defining a hole in the bone in which the anchor is positioned.

26 Claims, 40 Drawing Sheets

(51) Int. Cl.
*A61B 17/92* (2006.01)
*A61B 90/00* (2016.01)

(52) U.S. Cl.
CPC ............... *A61B 2017/0441* (2013.01); *A61B 2017/0445* (2013.01); *A61B 2017/0446* (2013.01); *A61B 2017/0464* (2013.01)

(58) Field of Classification Search
CPC .... A61B 2017/0446; A61B 2017/0414; A61B 2017/0412; A61B 17/7074; A61B 17/68; A61B 17/7077; A61B 17/7083; A61B 17/0469; A61B 2017/0474; A61B 2017/047; A61B 2017/0469; A61F 2/0811
See application file for complete search history.

(56) References Cited

U.S. PATENT DOCUMENTS

| | | | |
|---|---|---|---|
| 5,366,133 A | 11/1994 | Geiste | |
| 5,499,991 A | 3/1996 | Garman et al. | |
| 5,569,269 A | 10/1996 | Hart et al. | |
| 5,645,566 A | 7/1997 | Brenneman et al. | |
| 5,707,394 A | 1/1998 | Miller et al. | |
| 5,752,964 A | 5/1998 | Mericle | |
| 5,762,255 A | 6/1998 | Chrisman et al. | |
| 5,817,111 A | 10/1998 | Riza | |
| 6,508,830 B2 | 1/2003 | Steiner | |
| 6,544,281 B2 | 4/2003 | ElAttrache et al. | |
| 6,605,047 B2 | 8/2003 | Zarins et al. | |
| 6,991,636 B2 | 1/2006 | Rose | |
| 7,083,576 B2 | 8/2006 | Zarins et al. | |
| 7,329,272 B2 | 2/2008 | Burkhart et al. | |
| 7,494,461 B2 | 2/2009 | Wells et al. | |
| D605,764 S | 12/2009 | Griffis, III et al. | |
| 7,662,160 B2 | 2/2010 | Bojarski et al. | |
| 7,780,055 B2 | 8/2010 | Scirica et al. | |
| 7,842,050 B2 | 11/2010 | Diduch et al. | |
| 7,879,046 B2 | 2/2011 | Weinert et al. | |
| 7,993,369 B2 | 8/2011 | Dreyfuss | |
| 8,114,128 B2 | 2/2012 | Cauldwell et al. | |
| 8,133,257 B2 | 3/2012 | Cook et al. | |
| 8,133,258 B2 | 3/2012 | Foerster et al. | |
| 8,317,829 B2 | 11/2012 | Foerster et al. | |
| 8,425,536 B2 | 4/2013 | Foerster et al. | |
| 8,430,909 B2 | 4/2013 | Dreyfuss | |
| 8,435,264 B2 | 5/2013 | Sojka et al. | |
| 8,469,983 B2 | 6/2013 | Fung et al. | |
| 8,556,970 B2 | 10/2013 | Piccirillo | |
| 8,808,313 B2 | 8/2014 | Thorne et al. | |
| 8,882,801 B2 | 11/2014 | DiMatteo et al. | |
| 9,034,001 B2 | 5/2015 | Cheng et al. | |
| 9,107,662 B2 | 8/2015 | Kostrzewski | |
| 9,113,859 B2 | 8/2015 | Dooney, Jr. et al. | |
| 9,179,907 B2 | 11/2015 | ElAttrache et al. | |
| 9,220,497 B1 | 12/2015 | Lanois et al. | |
| 9,226,817 B2 | 1/2016 | Dougherty et al. | |
| 9,277,910 B2 | 3/2016 | Nason et al. | |
| 9,277,951 B1 | 3/2016 | Hovis | |
| 9,295,460 B2 | 3/2016 | Hoof et al. | |
| 9,370,351 B2 | 6/2016 | Sojka et al. | |
| 9,451,951 B2 | 9/2016 | Sullivan et al. | |
| 9,456,818 B2 | 10/2016 | Torrie | |
| 9,486,207 B2 | 11/2016 | Dooney, Jr. et al. | |
| 9,526,492 B2 | 12/2016 | Lombardo et al. | |
| 9,545,252 B2 | 1/2017 | Howard et al. | |
| 9,566,060 B2 | 2/2017 | Dougherty et al. | |
| 9,706,986 B2 | 7/2017 | ElAttrache et al. | |
| 9,717,587 B2 | 8/2017 | Dougherty et al. | |
| 9,763,655 B2 | 9/2017 | Sengun | |
| 9,770,240 B2 | 9/2017 | Dougherty et al. | |
| 9,775,599 B2 | 10/2017 | ElAttrache et al. | |
| 9,782,250 B2 | 10/2017 | Dougherty et al. | |
| 9,795,374 B2 | 10/2017 | Dougherty et al. | |
| 9,801,621 B2 | 10/2017 | Benavitz | |
| 9,801,629 B2 | 10/2017 | Farascioni et al. | |
| 9,808,240 B2 | 11/2017 | Parsons et al. | |
| 9,888,915 B2 | 2/2018 | Torrie | |
| 9,907,548 B2 | 3/2018 | Dougherty et al. | |
| 9,936,940 B2 * | 4/2018 | Palese | A61B 17/0401 |
| 9,999,496 B2 | 6/2018 | Dougherty et al. | |
| 10,039,546 B2 | 8/2018 | Williams et al. | |
| 10,052,091 B2 | 8/2018 | Dreyfuss et al. | |
| 10,085,746 B2 | 10/2018 | Fischvogt | |
| 10,149,678 B1 | 12/2018 | Martin et al. | |
| 10,149,752 B2 | 12/2018 | Dougherty et al. | |
| 10,159,478 B2 | 12/2018 | Howard et al. | |
| D842,471 S | 3/2019 | Alladu et al. | |
| 10,238,377 B2 | 3/2019 | Nason et al. | |
| 10,265,062 B2 | 4/2019 | Foerster et al. | |
| 10,335,137 B2 | 7/2019 | Arai et al. | |
| 10,433,830 B2 | 10/2019 | Sengun et al. | |
| 10,512,454 B2 | 12/2019 | Heneveld | |
| 10,548,711 B2 | 2/2020 | Dougherty et al. | |
| 10,582,925 B2 | 3/2020 | Marks et al. | |
| 10,709,436 B2 | 7/2020 | Burkhart et al. | |
| 10,716,556 B2 | 7/2020 | ElAttrache et al. | |
| 10,888,312 B2 | 1/2021 | Balboa et al. | |
| 2004/0082956 A1 | 4/2004 | Baldwin et al. | |
| 2004/0153074 A1 | 8/2004 | Bojarski et al. | |
| 2007/0219557 A1* | 9/2007 | Bourque | A61B 17/0401 606/326 |
| 2009/0076545 A1 | 3/2009 | DiMatteo et al. | |
| 2009/0248068 A1 | 10/2009 | Lombardo et al. | |
| 2011/0224726 A1 | 9/2011 | Lombardo et al. | |
| 2013/0144334 A1* | 6/2013 | Bouduban | A61B 17/0401 606/232 |
| 2014/0243892 A1 | 8/2014 | Choinski | |
| 2015/0209026 A1 | 7/2015 | Lanois et al. | |
| 2016/0135801 A1* | 5/2016 | Lombardo | A61B 17/0401 606/232 |
| 2016/0310127 A1* | 10/2016 | Cavallazzi | A61B 17/0401 |
| 2017/0000476 A1 | 1/2017 | Dougherty et al. | |
| 2017/0042533 A1 | 2/2017 | Lunn et al. | |
| 2017/0172562 A1 | 6/2017 | Lombardo | |
| 2017/0303912 A1 | 10/2017 | ElAttrache et al. | |
| 2018/0235598 A1 | 8/2018 | Burkhart et al. | |
| 2018/0235599 A1 | 8/2018 | Burkhart et al. | |
| 2018/0256152 A1 | 9/2018 | Palese et al. | |
| 2018/0338755 A1 | 11/2018 | Palese et al. | |
| 2019/0053888 A1 | 2/2019 | Dougherty et al. | |
| 2019/0090868 A1* | 3/2019 | Bracy | A61B 17/0401 |
| 2019/0159771 A1 | 5/2019 | Balboa et al. | |
| 2019/0159772 A1 | 5/2019 | Norton et al. | |
| 2019/0167252 A1 | 6/2019 | Nason et al. | |
| 2019/0290420 A1 | 9/2019 | Dougherty et al. | |
| 2019/0350577 A1 | 11/2019 | Norton et al. | |
| 2019/0380692 A1 | 12/2019 | Brazil et al. | |
| 2020/0008926 A1 | 1/2020 | Power | |
| 2020/0015809 A1 | 1/2020 | Cauldwell et al. | |
| 2020/0015816 A1 | 1/2020 | Cauldwell et al. | |
| 2020/0155137 A1 | 5/2020 | Brunsvold et al. | |
| 2020/0205805 A1 | 7/2020 | Marks et al. | |
| 2020/0253598 A1 | 8/2020 | Holmes, Jr. | |
| 2021/0338223 A1 | 11/2021 | Patel et al. | |
| 2021/0338224 A1 | 11/2021 | Patel et al. | |
| 2021/0338225 A1 | 11/2021 | Patel et al. | |
| 2023/0149009 A1 | 5/2023 | Housman et al. | |

FOREIGN PATENT DOCUMENTS

| | | | |
|---|---|---|---|
| WO | 2012177386 A1 | 12/2012 | |
| WO | WO-2019014557 A1 | 1/2019 | |

OTHER PUBLICATIONS

MSC Industrial Supply Co., "Tech Essentials: Thread Forming Taps," dated no later than Apr. 10, 2021, available at <https://www.mscdirect.com/basicsof/thread-forming-taps> (1 page).

Invitation to Pay Additional Fees and, Where Applicable, Protest Fee for Intl. App. No. PCT/US2021/029293 dated Aug. 13, 2021 (16 pages).

(56) References Cited

OTHER PUBLICATIONS

International Search Report and Written Opinion for Intl. App. No. PCT/US2021/029293 dated Nov. 3, 2021 (28 pages).
U.S. Appl. No. 17/241,308, filed Apr. 27, 2021, Ravi Patel et al.
U.S. Appl. No. 17/241,317, filed Apr. 27, 2021, Ravi Patel et al.
U.S. Appl. No. 29/780,871, filed Apr. 27, 2021, Mark Shainwald et al.

* cited by examiner

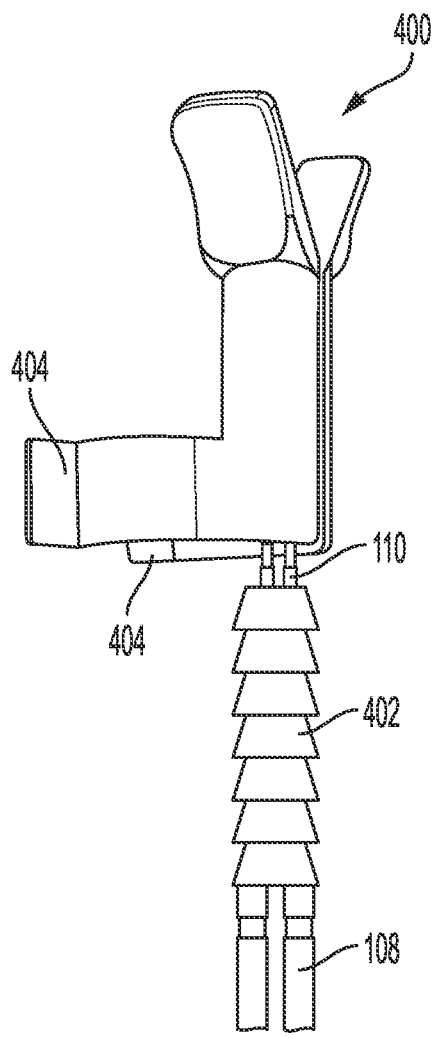
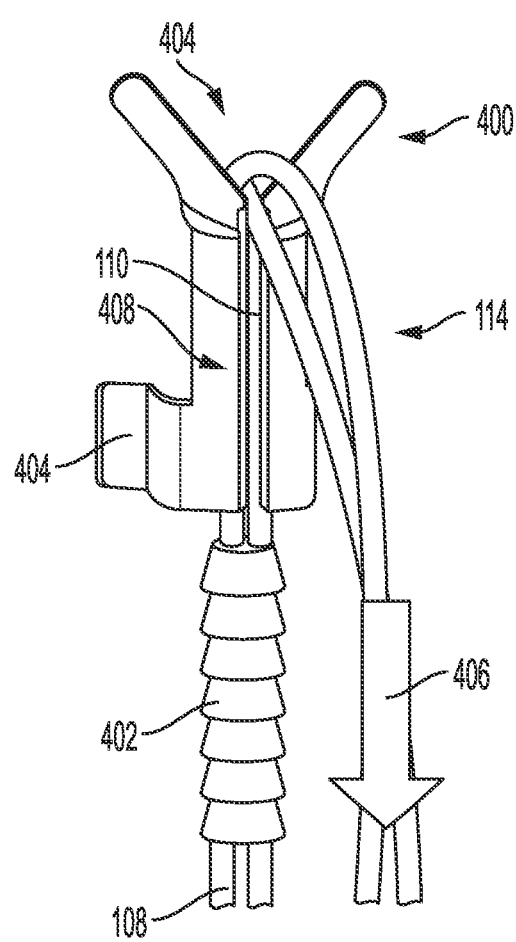
FIG. 14
FIG. 15

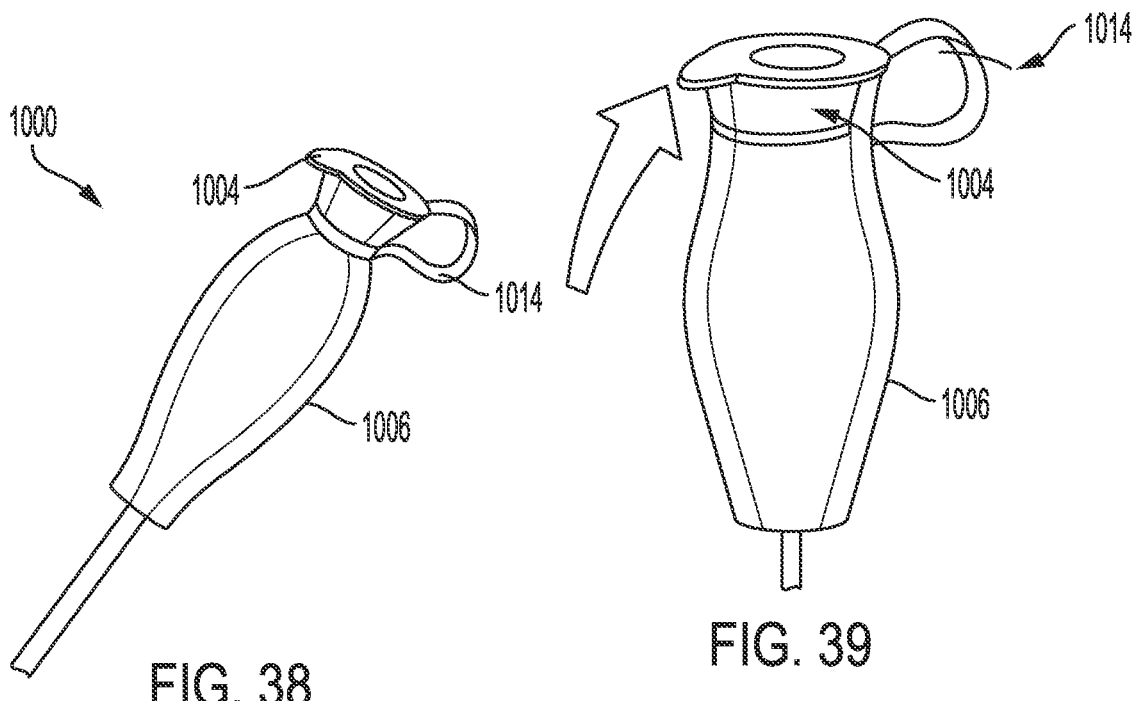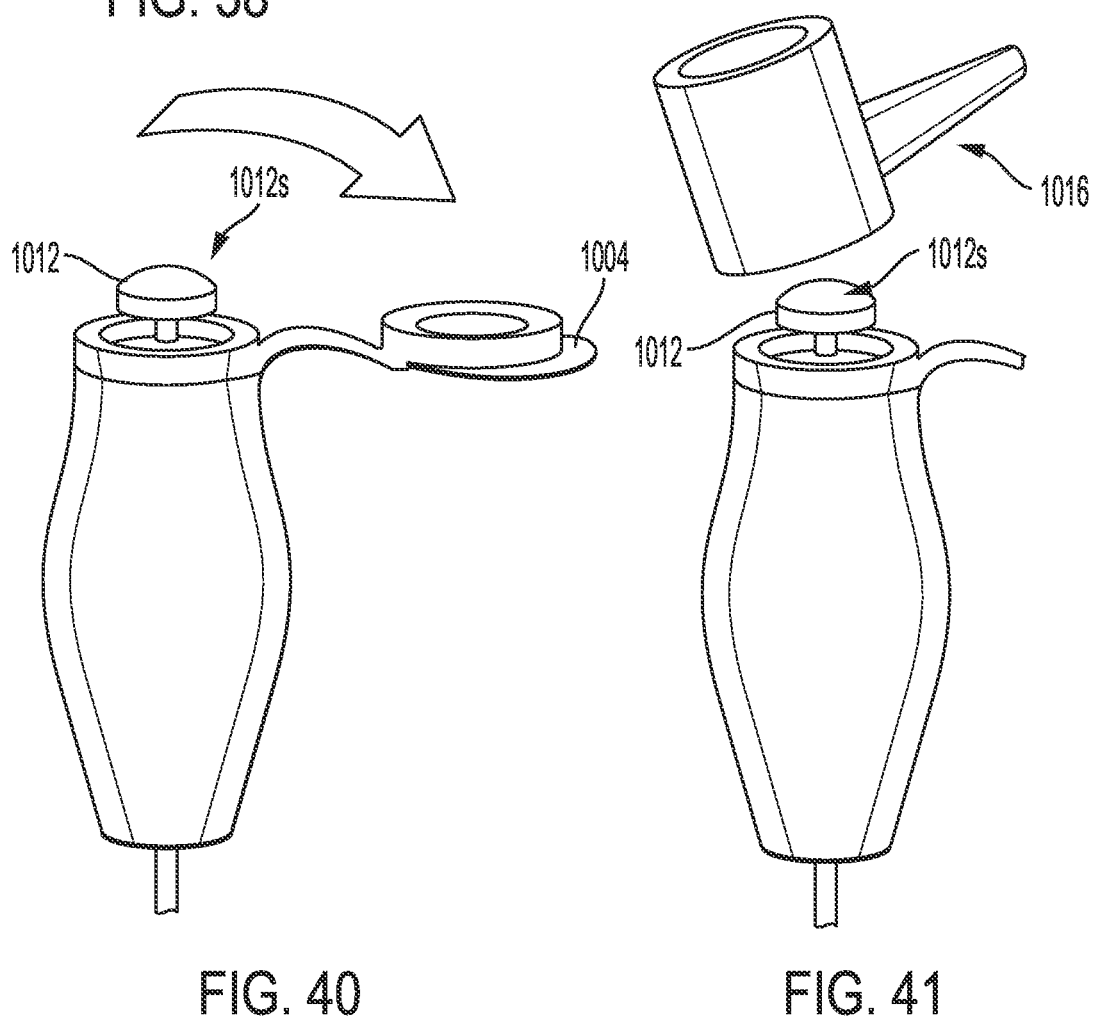

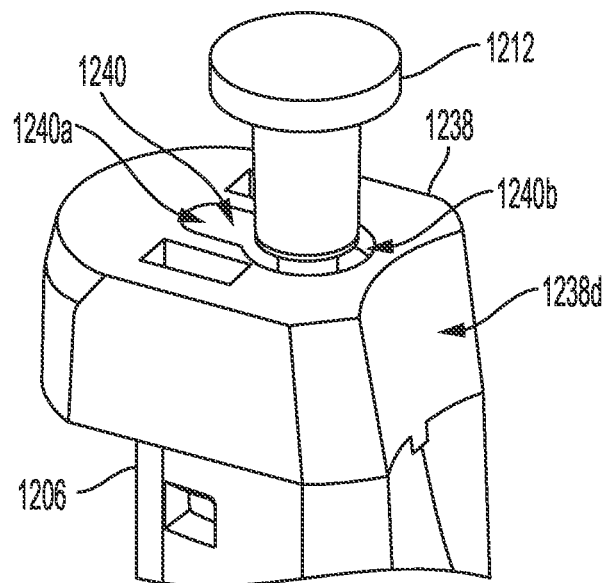
FIG. 54
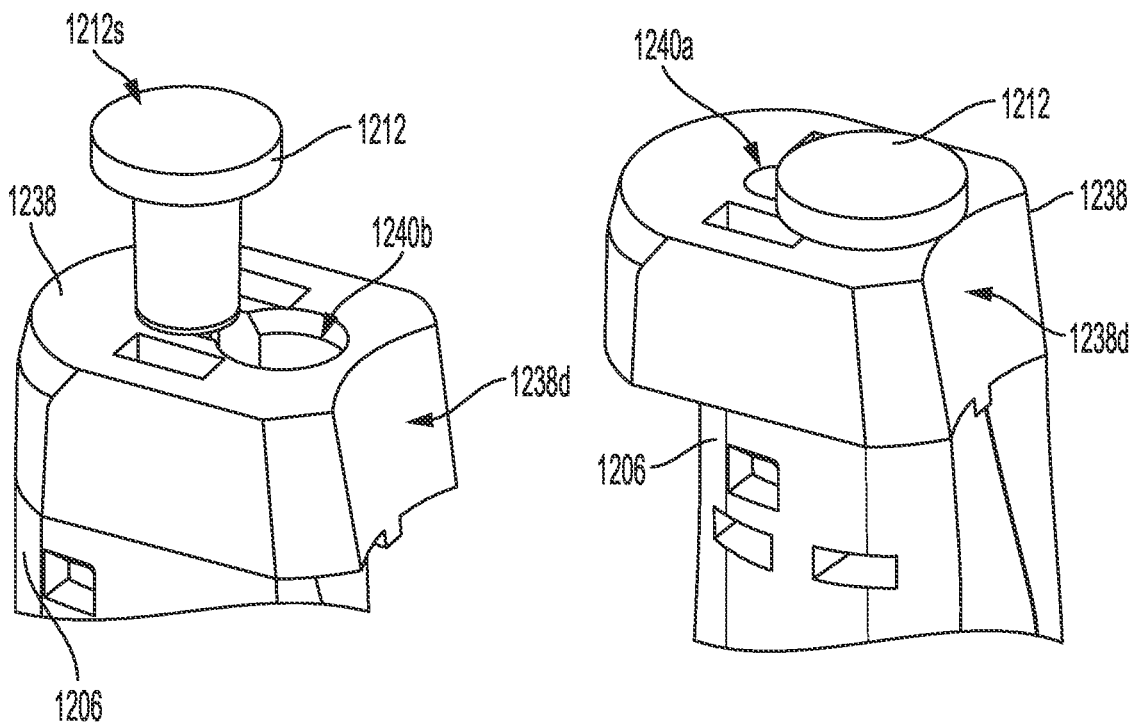
FIG. 55
FIG. 56

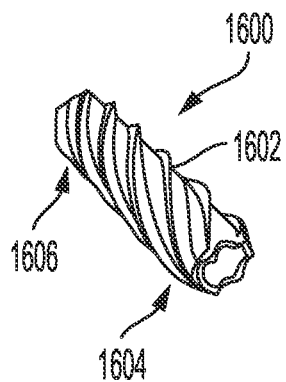 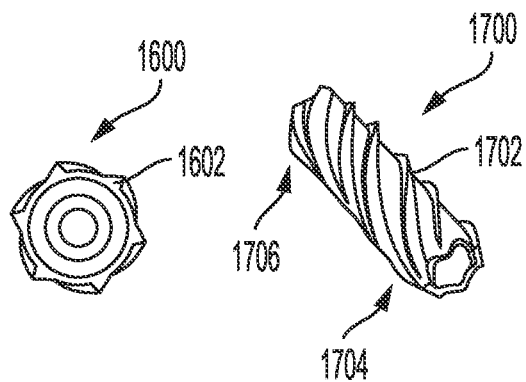 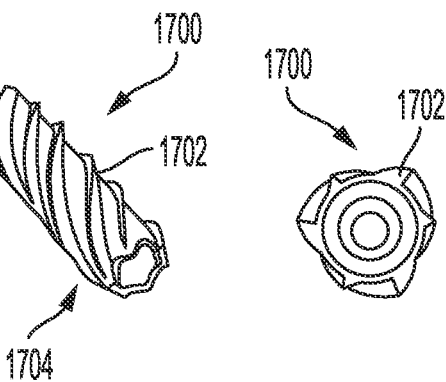 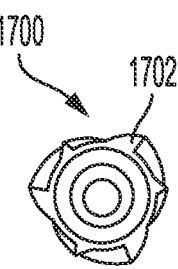
FIG. 80   FIG. 81   FIG. 82   FIG. 83
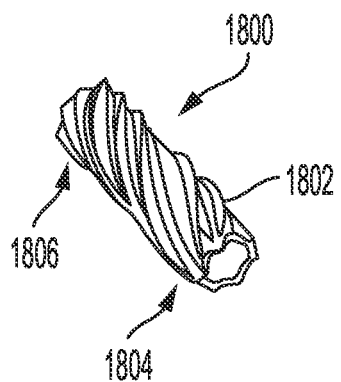 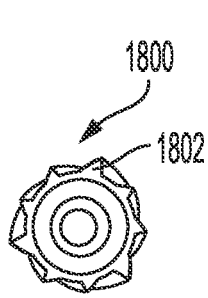 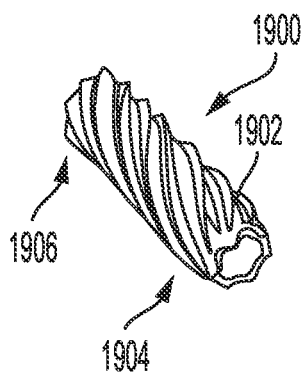 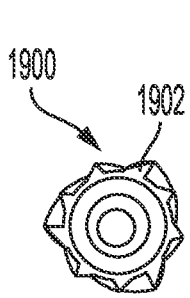
FIG. 84   FIG. 85   FIG. 86   FIG. 87
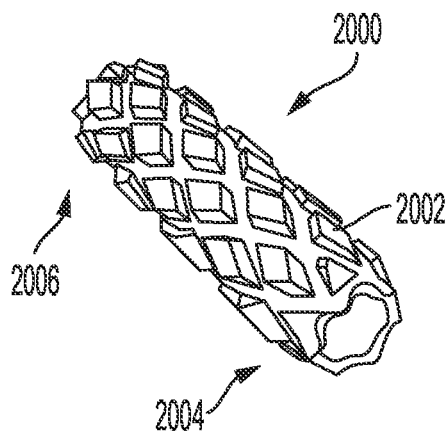 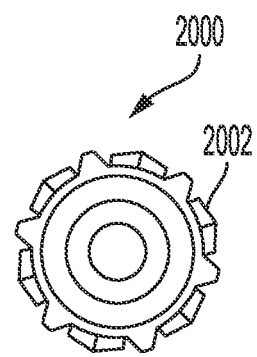
FIG. 88   FIG. 89

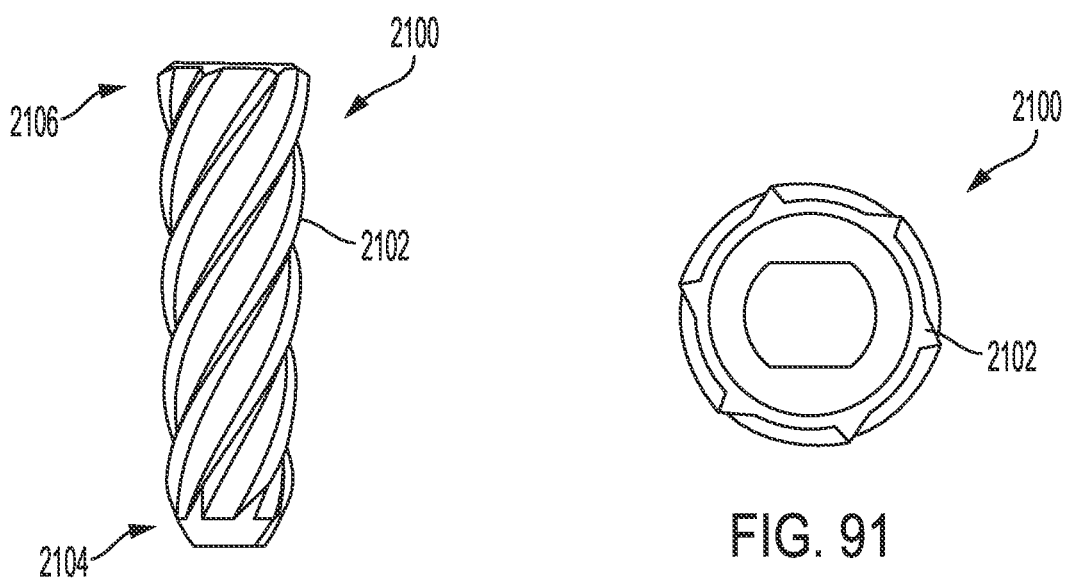
FIG. 90
FIG. 91
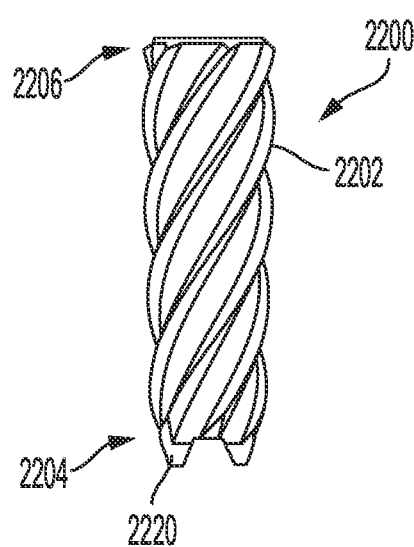
FIG. 92
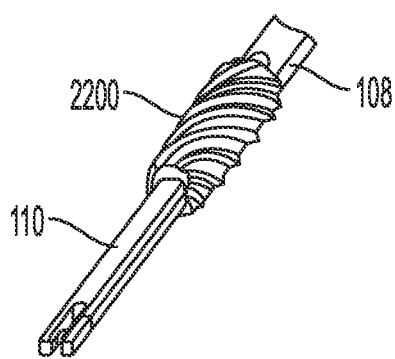
FIG. 93
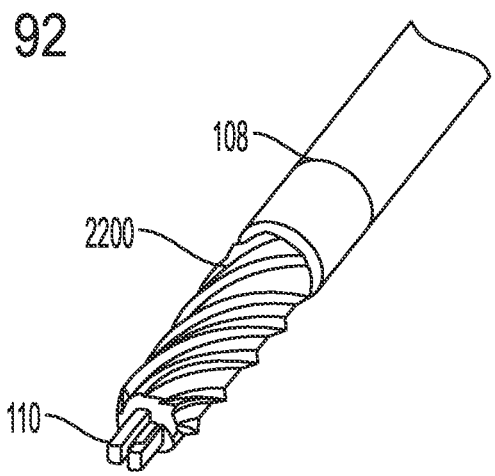
FIG. 94

KNOTLESS ANCHOR INSERTION

CROSS REFERENCE TO RELATED APPLICATIONS

The present application claims priority to U.S. Prov. Pat. App. No. 63/017,009 entitled "Knotless Anchor Insertion" filed Apr. 29, 2020, which is hereby incorporated by reference in its entirety.

FIELD

The present disclosure relates generally to knotless anchor insertion.

BACKGROUND

A variety of injuries and conditions require repair of soft tissue damage, or reattachment of soft tissue to bone and/or surrounding tissue. For example, when otherwise healthy tissue has been torn away from a bone, such as a labrum tearing away from a glenoid (shoulder instability), surgery is often required to reattach the tissue to the bone, to allow healing and a natural reattachment to occur. A number of devices and methods have been developed for performing these surgical repairs. Some of the more successful methods including the use of suture fixation members, such as suture anchors, which typically include an anchor body having a suture attachment feature and a tissue or bone engaging feature for retaining the suture anchor within or adjacent to the tissue or bone. Depending on the specific injury, one or more suture anchors connected to, or interconnected by, one or more segment of suture, may be used to perform the repair.

Surgery can also be required when a tear occurs in the substance of a single type of tissue. Sutures can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small diameter cannula, an endoscopic tube, or otherwise percutaneously, which can make the knotting process difficult and tedious. However, while knotless anchors can be very effective in reattaching soft tissue to bone, the small size of the anchor and patient anatomy can make it difficult to locate and insert the anchor into the bone hole. Additionally, visualization of the hole can be difficult due to challenging angles and the tight nature of the joint space.

Accordingly, there remains a need for improved knotless anchor insertion.

SUMMARY

In general, systems and devices for knotless anchor insertion and methods of knotless anchor insertion are provided.

In one aspect, a surgical system is provided that in one embodiment includes a handle, an outer shaft extending distally from the handle and including an inner lumen, and an inner shaft extending distally from the handle. The inner shaft is positioned in the inner lumen of the outer shaft, a distal end of the inner shaft is positioned distal to an open distal end of the outer shaft, and the distal end of the inner shaft has a notch formed therein that is configured to seat a suture therein. The system also includes an anchor configured to be implanted in bone. The anchor includes an inner lumen, and the inner shaft is positioned in the inner lumen of the anchor. With the distal end of the inner shaft positioned in a bone hole, the outer shaft is configured to translate longitudinally and distally relative to the inner shaft and thereby cause the anchor to translate longitudinally and distally into the bone hole.

The system can vary in any number of ways. For example, after the translation of the outer shaft, the outer shaft and the inner shaft can be configured to simultaneously translate longitudinally and proximally relative to the anchor in the bone hole. For another example, prior to the translation of the outer shaft, a distal end of the outer shaft can abut a proximal end of the anchor having the inner shaft positioned in the inner lumen of the anchor.

For yet another example, the notch can have an open distal end and a closed proximal end. The system can also include a pliable member that extends along the open distal end of the notch so as to define an enclosed passage in cooperation with the inner shaft, and the enclosed passage can be configured to seat the suture therethrough. The pliable member can be configured to bend such that the enclosed passage is opened to allow the suture to be released. The pliable member can be made from a shape memory or superelastic material.

For still another example, the notch can extend longitudinally along a longitudinal axis of the inner shaft. For yet another example, the notch can define a tortuous path. For still another example, the anchor can have a plurality of bone-engaging surface features configured to engage a wall of the bone hole to secure the anchor in the bone hole. For yet another example, a distal portion of the inner shaft including the notch can be made from a shape memory or superelastic material.

For another example, the inner shaft can include distal arms that define the notch therebetween. The notch can have an open distal end, and the arms can each be configured to flex radially outward in response to a suture passing through the open distal end. The arms can be made from a shape memory or superelastic material.

For yet another example, the system can include the suture seated in the notch. The suture can be seated in the notch prior to the distal end of the inner shaft being positioned in the bone hole and can be seated in the notch after the translation of the outer shaft such that the anchor traps the suture between an exterior surface of the anchor and a wall of the bone hole. The system can include a suture retention member at the handle, and the suture retention member can be configured to releasably retain the suture therein. After the translation of the outer shaft, the inner shaft can be configured to translate longitudinally and proximally relative to the anchor in the bone hole, the notch can have an open distal end, and the suture can be configured to pass out of the notch through the open distal end in response to the longitudinal and proximal translation of the inner shaft.

For still another example, the system can include a locking mechanism configured to move from a locked position, in which the outer shaft is prevented from translating longitudinally and distally relative to the inner shaft, to an unlocked position, in which the outer shaft is allowed to translate longitudinally and distally relative to the inner shaft.

For yet another example, the system can include a strike cap extending proximally from the handle and being operatively coupled to the outer shaft, and the strike cap can be configured to be hit by a tool and thereby cause the outer shaft to translate longitudinally and distally relative to the inner shaft. The system can include a locking mechanism configured to move from a locked position, in which the outer shaft is prevented from translating longitudinally and distally relative to the inner shaft in response to a hit on the strike cap, to an unlocked position, in which the outer shaft is allowed to translate longitudinally and distally relative to the inner shaft in response to a hit on the strike cap. The system can include a protective member configured to move from a closed position, in which the protective member covers a strike surface of the strike cap, to an open position, in which the protective member does not cover a strike surface of the strike cap. The protective member can be attached to the handle via a hinge. The hinge can be a living hinge.

For another example, the system can include the suture and a loading aid that can be configured to releasably couple to the inner shaft and can be configured to guide the suture into the notch. The loading aid can include a first channel configured to guide the suture therethrough and into the notch formed in the inner shaft with the loading aid releasably coupled to the inner shaft. The loading aid can have a second channel formed therein that is in communication with the first channel, and the inner shaft can be configured to pass through the second channel during release of the loading aid from the inner shaft. The loading aid can be configured to be released from the inner shaft after the suture has been seated in the notch and before the distal end of the inner shaft is positioned in the bone hole. The loading aid can include a V-shaped distal seating groove, and the distal seating groove can be in communication with the first channel such that the suture is configured to be seated in the distal seating groove and pass into the first channel so as to automatically seat the suture in the notch.

In another embodiment, a surgical system includes an inserter tool, a suture, and an anchor. The inserter tool includes an outer shaft, and an inner shaft. A distal end of the inner shaft has a suture retention channel formed therein, and the inner shaft is positioned in the outer shaft with the suture retention channel positioned distal to an open distal end of the outer shaft. The suture is seated in the suture retention channel. The anchor is configured to be implanted in bone and having the inner shaft seated in a cannulated interior thereof. The anchor is configured to be pushed distally by the outer shaft moving axially and distally along a longitudinal axis of the inserter tool relative to the inner shaft and the suture.

The system can have any number of variations. For example, after the axial movement of the outer shaft, the outer shaft and the inner shaft can be configured to simultaneously move axially and proximally along the longitudinal axis of the inserter tool relative to the anchor and the suture. For another example, prior to the axial movement of the outer shaft, a distal end of the outer shaft can abut a proximal end of the anchor having the inner shaft positioned therein.

For yet another example, the suture retention channel can have an open distal end and a closed proximal end. The system can include a pliable member that extends along the open distal end of the suture retention channel so as to define an enclosed passage in cooperation with the inner shaft, and the enclosed passage can be configured to seat the suture therethrough. The pliable member can be configured to bend such that the enclosed passage is opened to allow the suture to be released. The pliable member can be made from a shape memory or superelastic material.

For still another example, the suture retention channel can extend longitudinally along a longitudinal axis of the inner shaft. For another example, the suture retention channel can define a tortuous path.

For yet another example, the inner shaft can include a pair of distal arms that define the suture retention channel therebetween. The suture retention channel can have an open distal end, and the arms can each be configured to flex radially outward in response to the suture passing through the open distal end. The arms can be made from a shape memory or superelastic material.

For still another example, after the axial movement of the outer shaft, the inner shaft can be configured to move axially and proximally along the longitudinal axis of the inserter tool relative to the anchor and the suture, the suture retention channel can have an open distal end, and the suture can be configured to pass out of the suture retention channel through the open distal end in response to the axial and proximal translation of the inner shaft. For another example, the anchor can have a plurality of bone-engaging surface features configured to engage a wall of a bone hole to secure the anchor in the bone hole.

For yet another example, the inserter tool can include a handle, and the outer and inner shafts can extend distally from the handle. The system can include a suture retention member at the handle, and the suture retention member can be configured to releasably retain the suture therein.

For another example, the inserter tool can include a locking mechanism configured to move from a locked position, in which the outer shaft is prevented from moving axially and distally relative to the inner shaft, to an unlocked position, in which the outer shaft is allowed to move axially and distally relative to the inner shaft.

For yet another example, the inserter tool can include a strike cap operatively coupled to the outer shaft, and the strike cap can be configured to be hit by a tool and thereby cause the outer shaft to move axially and distally relative to the inner shaft. The inserter tool can include a locking mechanism configured to move from a locked position, in which the outer shaft is prevented from moving axially and distally relative to the inner shaft in response to a hit on the strike cap, to an unlocked position, in which the outer shaft is allowed to move axially and distally relative to the inner shaft in response to a hit on the strike cap. The inserter tool can include a protective member configured to move from a closed position, in which the protective member covers a strike surface of the strike cap, to an open position, in which the protective member does not cover a strike surface of the strike cap. The protective member can be attached to the inserter tool via a hinge. The hinge can be a living hinge.

For still another example, the system can include a loading aid configured to releasably couple to the inner shaft and configured to guide the suture into the suture retention channel. The loading aid can include a first channel configured to guide the suture therethrough and into the suture retention channel formed in the inner shaft with the loading aid releasably coupled to the inner shaft. The loading aid can be configured to be released from the inner shaft after the suture has been seated in the suture retention channel. The loading aid can have a second channel formed therein that is in communication with the first channel, and the inner shaft can be configured to pass through the second channel during the release of the loading aid from the inner shaft. The loading aid can include a V-shaped distal seating groove, and the distal seating groove can be in communication with the first channel such that the suture is configured to be seated in the distal seating groove and pass into the first channel so as to automatically seat the suture in the suture retention channel.

In another embodiment, a surgical system includes a handle, an outer shaft extending distally from the handle and including an inner lumen, and an inner shaft extending distally from the handle. The inner shaft is positioned in the inner lumen of the outer shaft, and a distal end of the inner shaft being positioned distal to an open distal end of the outer shaft. The system also includes a pliable member cooperating with the distal end of the inner shaft to define an enclosed passage that is configured to seat a suture therethrough. The system also includes an anchor configured to be implanted in bone. The anchor includes an inner lumen, and the inner shaft is positioned in the inner lumen of the anchor. The outer shaft is configured to translate relative to the inner shaft and thereby cause the anchor to translate distally into a bone hole. The pliable member is configured to bend to open the enclosed passage.

The system can vary in any number of ways. For example, the pliable member can be configured to automatically unfold in response to longitudinal and proximal translation of the inner shaft relative to the anchor and thereby cause the enclosed passage to be opened. For another example, the movement of the outer shaft can be longitudinal and distal relative to the inner shaft and can be with the distal end of the inner shaft positioned in the bone hole, and the translation of the anchor can be longitudinal and distal into the bone hole.

For another example, after the translation of the outer shaft, the outer shaft and the inner shaft can be configured to simultaneously translate longitudinally and proximally relative to the anchor in the bone hole.

For yet another example, a first end of the pliable member can be fixedly attached to the handle, and a second end of the pliable member can be freely movable relative to the handle and the inner shaft. The second end of the pliable member can be configured to automatically bend relative to the inner shaft in response to the longitudinal and proximal translation of the inner shaft relative to the anchor.

For another example, a proximal surface of the inner shaft can define a proximal side of the enclosed passage, the pliable member can define a distal side of the enclosed passage, and the inner shaft can include a pair of opposed distal arms that define left and right sides of the enclosed passage that each extend between the proximal and distal sides of the enclosed passage. For still another example, the system can include a wire operatively coupled to the pliable member, and an actuator at the handle configured to be actuated and thereby cause the wire to move proximally, and the proximal movement of the wire can cause bending of the pliable member such that the enclosed passage is opened.

For yet another example, the pliable member can include a metal wire, a braided fabric, or a textile strand. The pliable member can be made from a shape memory or superelastic material.

For another example, prior to the translation of the outer shaft, a distal end of the outer shaft can abut a proximal end of the anchor having the inner shaft positioned in the inner lumen of the anchor. For still another example, the anchor can have a plurality of bone-engaging surface features configured to engage a wall of a bone hole to secure the anchor in the bone hole. For another example, the anchor can have a plurality of independent external bone-engaging surface features that helically extend along a length of the anchor and that are each configured to engage the bone. For still another example, the anchor can have a plurality of bone-engaging surface features and a plurality of gussets.

For yet another example, the system can include the suture seated through the enclosed passage. The suture can be seated through the enclosed passage prior to the distal end of the inner shaft being positioned in the bone hole and can be seated through the enclosed passage after the translation of the outer shaft such that the anchor traps the suture between an exterior surface of the anchor and a wall of the bone hole. The system can include a suture retention member at the handle, and the suture retention member can be configured to releasably retain the suture therein.

For another example, after the translation of the outer shaft, the inner shaft can be configured to translate longitudinally and proximally relative to the anchor in the bone hole, and the translation of the inner shaft can be configured to automatically cause the bending of the pliable member, thereby allowing release of the suture from the enclosed passage.

For still another example, the system can include a locking mechanism configured to move from a locked position, in which the outer shaft is prevented from translating longitudinally and distally relative to the inner shaft, to an unlocked position, in which the outer shaft is allowed to translate longitudinally and distally relative to the inner shaft.

For another example, the system can include a strike cap extending proximally from the handle and being operatively coupled to the outer shaft, and the strike cap can be configured to be hit by a tool and thereby cause the outer shaft to translate longitudinally and distally relative to the inner shaft. The system can include a locking mechanism configured to move from a locked position, in which the outer shaft is prevented from translating longitudinally and distally relative to the inner shaft in response to a hit on the strike cap, to an unlocked position, in which the outer shaft is allowed to translate longitudinally and distally relative to the inner shaft in response to a hit on the strike cap. The system can include a protective member configured to move from a closed position, in which the protective member covers a strike surface of the strike cap, to an open position, in which the protective member does not cover a strike surface of the strike cap. The protective member can be attached to the handle via a hinge. The hinge can be a living hinge.

For another example, the system can include the suture and a loading aid that can be configured to releasably couple to the inner shaft and is configured to guide the suture through the enclosed passage. The loading aid can include a suture threader.

In another embodiment, a surgical system is provided that includes a handle, an outer shaft extending distally from the handle and including an inner lumen, and an inner shaft extending distally from the handle. The inner shaft is positioned in the inner lumen of the outer shaft, a distal end of the inner shaft is positioned distal to an open distal end of the outer shaft, and the distal end of the inner shaft includes first and second interlocked components that define an enclosed passage configured to receive a suture therethrough. The system also includes an anchor configured to be implanted in bone. The anchor includes an inner lumen, and the inner shaft is positioned in the inner lumen of the anchor. Movement of the outer shaft relative to the inner shaft is configured to cause the anchor to translate longitudinally and distally into a bone hole. The first component is configured to move relative to the second component, thereby opening the enclosed passage.

The system can vary in any number of ways. For example, the system can include the suture, and the movement of the first component can be configured to automatically open the enclosed passage, thereby allowing release of the suture.

For another example, the movement of the outer shaft relative to the inner shaft can include longitudinal and distal translation of the outer shaft relative to the inner shaft before the first component moves relative to the second component. The movement of the outer shaft can be configured to occur with the distal end of the inner shaft positioned in a bone hole, and the suture can extend through the enclosed passage after the translation of the outer shaft such that the anchor traps the suture between an exterior surface of the anchor and a wall of the bone hole. The first component can be configured to move relative to the second component after the movement of the outer shaft, and the opening of the enclosed passage can allow release of the suture.

In another embodiment, a surgical system is provided that includes a biocompatible anchor configured to be advanced distally into bone. The anchor has a plurality of independent external bone-engaging surface features that helically extend along a length of the anchor and that are each configured to engage the bone. The anchor tapers radially inward in a distal direction such that a diameter of the tapered helical anchor at a proximal end of the anchor is greater than a diameter of the anchor at a distal end of the anchor.

The system can have any number of variations. For example, each of the bone-engaging surface features can extend along an entire length of the anchor. For another example, each of the bone-engaging surface features can extend along a partial length of the anchor such that the anchor has a thread proximal portion and an unthreaded distal portion. For yet another example, the anchor can be cannulated. For still another example, the bone-engaging surface features can be threads.

For another example, the system can also include an inserter tool that includes an outer shaft and an inner shaft, the outer shaft can include an inner lumen, the inner shaft can be positioned in the inner lumen of the outer shaft, a distal end of the inner shaft can be positioned distal to an open distal end of the outer shaft, the distal end of the inner shaft can have a notch formed therein that is configured to seat a suture therein, the inner shaft can be configured to be positioned in an inner lumen of the anchor, and, with the inner shaft position in the inner lumen of the anchor, the outer shaft can be configured to translate longitudinally and distally relative to the inner shaft and thereby cause the anchor to translate longitudinally and distally into a bone hole. After the translation of the outer shaft, the outer shaft and the inner shaft can be configured to simultaneously translate longitudinally and proximally relative to the anchor in the bone hole. Prior to the translation of the outer shaft, a distal end of the outer shaft can abut the proximal end of the anchor having the inner shaft positioned in the inner lumen of the anchor. The system can include the suture, and the translation of the outer shaft can be configured to cause the anchor to trap the suture between the anchor and a wall of the bone hole. The inserter tool can also include a strike cap operatively coupled to the outer shaft and configured to be hit by a tool and thereby cause the outer shaft to translate longitudinally and distally relative to the inner shaft and the anchor to translate longitudinally and distally into the bone hole.

In another embodiment, a surgical system includes a biocompatible anchor and an inserter tool. A plurality of independent external threads each extend helically along a length of the anchor and are each configured to engage bone. An inner lumen extends through the anchor. An outer diameter of the anchor decreases in a distal direction along an entire length of the anchor. The inserter tool includes an outer shaft and an inner shaft. The outer shaft includes an inner lumen. The inner shaft is positioned in the inner lumen of the outer shaft. The distal end of the inner shaft has a notch formed therein that is configured to seat a suture therein. The inner shaft extends through the inner lumen of the anchor, and a distal end of the inner shaft is positioned distal to an open distal end of the outer shaft. The outer shaft is configured to translate longitudinally and distally relative to the inner shaft and thereby cause the anchor to translate longitudinally and distally relative to the inner shaft.

The system can vary in any number of ways. For example, after the translation of the outer shaft, the outer shaft and the inner shaft can be configured to simultaneously translate longitudinally and proximally relative to the anchor. For another example, prior to the translation of the outer shaft, a distal end of the outer shaft can abut the proximal end of the anchor. For still another example, the bone-engaging surface features can be threads. For another example, the outer diameter of the anchor can decrease continuously in the distal direction along the entire length of the anchor.

For yet another example, the system can include the suture, the longitudinal and distal translation of the anchor can be configured to advance the anchor into a bone hole, and the translation of the outer shaft can be configured to cause the anchor to trap the suture between the anchor and a wall of the bone hole. After the translation of the outer shaft, the outer shaft and the inner shaft can be configured to simultaneously translate longitudinally and proximally relative to the anchor in the bone hole.

For still another example, the inserter tool can include a strike cap operatively coupled to the outer shaft and configured to be hit by a tool and thereby cause the outer shaft to translate longitudinally and distally relative to the inner shaft and the anchor to translate longitudinally and distally into a bone hole.

In another aspect, a surgical method is provided that in one embodiment includes positioning a distal end of an inner shaft of an inserter tool in a bone hole. The distal end of the inner shaft has a notch formed therein, and a suture is seated in the notch. The method also includes moving an outer shaft of the inserter tool axially and distally relative to the inner shaft, thereby causing an anchor to slide along the inner shaft and be positioned in the bone hole such that the anchor traps the suture between an exterior surface of the anchor and a wall of the bone hole. The method also includes, after the movement of the outer shaft axially and distally, moving the outer and inner shafts axially and proximally relative to the anchor such that the inner shaft is removed from the bone hole and the anchor and the suture remain in the bone hole.

The method can vary in any number of ways. For example, the axial and proximal movement of the inner shaft can automatically cause the suture to exit the notch by passing through an open distal end of the notch.

For another example, before the movement of the outer shaft axially and distally, a pliable member can extend along a distal side of the notch so as to prevent the suture from exiting the notch distally, and the axial and proximal movement of the inner shaft can automatically cause the pliable member to bend such that the suture can exit the notch. The pliable member can be made from a shape memory or superelastic material.

For yet another example, the axial and proximal movement of the inner shaft can automatically cause the suture to exit the notch by passing through an open distal end of the notch, the notch can be defined by a pair of distal arms of the inner shaft, and the arms can each flex radially outward in response to the suture passing through the open distal end of the notch. The arms can be made from a shape memory or superelastic material to facilitate radial inward movement of the arms after the suture passes through the open distal end of the notch.

For another example, the method can include, before the movement of the outer shaft axially and distally, tensioning the suture. For yet another example, the method can include retaining the suture in a suture retention member at a handle of the inserter tool. For still another example, the method can include, before the movement of the outer shaft axially and distally, moving a locking mechanism from a locked position, in which the outer shaft is prevented from translating axially and distally relative to the inner shaft, to an unlocked position, in which the outer shaft is allowed to translate axially and distally relative to the inner shaft.

For another example, striking a strike cap of the inserter tool can cause the movement of the outer shaft axially and distally. The method can include, before striking the strike cap, moving a locking mechanism from a locked position, in which the outer shaft is prevented from translating axially and distally relative to the inner shaft, to an unlocked position, in which the outer shaft is allowed to translate axially and distally relative to the inner shaft. The method can include, before striking the strike cap, moving a protective member from a closed position, in which the protective member covers a strike surface of the strike cap, to an open position, in which the protective member does not cover a strike surface of the strike cap.

For yet another example, the method can include, before positioning the distal end of the inner shaft in the bone hole, loading the suture into the notch by hand.

For still another example, the method can include, before positioning the distal end of the inner shaft in the bone hole, loading the suture into the notch using a tool that is releasably coupled to the inner shaft. The tool can include a loading aid, and loading the suture can include guiding the suture through a first channel of the loading aid and into the notch. Loading the suture can include guiding the suture from the first channel into a second channel of the loading aid that is in communication with the notch such that passing the suture into the second channel automatically seats the suture in the notch. Loading the suture can include guiding the suture from a V-shaped distal seating groove of the loading channel and into the first channel. The method can include releasing the tool from the inner shaft after the suture has been loaded into the notch using the tool.

In another embodiment, a surgical method includes positioning a distal end of an inner shaft of an inserter tool in a bone hole with a pliable member attached to the inner shaft. The pliable member and the inner shaft cooperate to define an enclosed passage through which a suture extends. The method also includes moving an outer shaft of the inserter tool axially and distally relative to the inner shaft, thereby causing an anchor to slide along the inner shaft and be positioned in the bone hole such that the anchor traps the suture between an exterior surface of the anchor and a wall of the bone hole. The method also includes, after the movement of the outer shaft axially and distally, moving the outer and inner shafts axially and proximally relative to the anchor such that the pliable member unfolds and such that the inner shaft is removed from the bone hole and the anchor and the suture remain in the bone hole.

The method can have any number of variations. For example, a first end of the pliable member can be fixedly attached to the inner shaft and can not be movable relative to the inner shaft, a second end of the pliable member can be freely movable relative to the inner shaft, the second end of the pliable member can automatically move relative to the inner shaft in response to the axial and proximal translation of the inner shaft to unfold the pliable member, and the movement of the pliable member can cause the enclosed passage to be opened.

For another example, a first end of the pliable member can be fixedly attached to a handle of the inserter tool and not be movable relative to the inner shaft, and a second end of the pliable member can be freely movable relative to the inner shaft, the second end of the pliable member can automatically move relative to the inner shaft in response to the axial and proximal translation of the inner shaft to unfold the pliable member, and the movement of the pliable member can cause the enclosed passage to be opened.

For another example, the method can include, before the movement of the outer shaft axially and distally, tensioning the suture. For yet another example, the method can include retaining the suture in a suture retention member at a handle of the inserter tool. For still another example, the method can include, before the movement of the outer shaft axially and distally, moving a locking mechanism from a locked position, in which the outer shaft is prevented from translating axially and distally relative to the inner shaft, to an unlocked position, in which the outer shaft is allowed to translate axially and distally relative to the inner shaft. For another example, the pliable member can be made from a shape memory or superelastic material.

For yet another example, striking a strike cap of the inserter tool can cause the movement of the outer shaft axially and distally. The method can include, before striking the strike cap, moving a locking mechanism from a locked position, in which the outer shaft is prevented from translating axially and distally relative to the inner shaft, to an unlocked position, in which the outer shaft is allowed to translate axially and distally relative to the inner shaft. The method can include, before striking the strike cap, moving a protective member from a closed position, in which the protective member covers a strike surface of the strike cap, to an open position, in which the protective member does not cover a strike surface of the strike cap.

For another example, the method can include, before positioning the distal end of the inner shaft in the bone hole, loading the suture into the enclosed passage using a suture threader.

In another embodiment, a surgical method includes positioning a distal end of an inner shaft of an inserter tool in a bone hole. The distal end of the inner shaft has a notch formed therein, a suture is seated in the notch, and the inner shaft extends through a cannulated tapered anchor that has a plurality of bone-engaging surface features extending helically along a length of the anchor. The method also includes moving an outer shaft of the inserter tool axially and distally relative to the inner shaft, thereby causing the anchor to slide along the inner shaft and be positioned in the bone hole such that the anchor traps the suture between an exterior surface of the anchor and a wall of the bone hole.

The method can vary in any number of ways. For example, the anchor can taper radially inward in a distal direction such that a diameter of the tapered helical anchor at a proximal end of the anchor is greater than a diameter of the anchor at a distal end of the anchor. With the anchor positioned in the bone hole, the proximal end of the anchor can engage cortical bone and the distal end of the anchor can engage cancellous bone.

For another example, the method can include, after the movement of the outer shaft axially and distally, moving the outer and inner shafts axially and proximally relative to the anchor such that the inner shaft is removed from the bone hole and the anchor and the suture remain in the bone hole.

For yet another example, the bone-engaging surface features can be threads.

BRIEF DESCRIPTION OF DRAWINGS

The present invention is described by way of reference to the accompanying figures which are as follows:

FIG. 14 is a perspective view of another embodiment of a loading aid coupled to the inserter tool of FIG. 1;

FIG. 15 is a perspective view of the loading aid and the inserter tool of FIG. 14 with a suture seated in a distal seating groove of the loading aid;

FIG. 38 is a perspective view of a proximal portion of yet another embodiment of an inserter tool with a protective member in a closed position;

FIG. 39 is another perspective view of a proximal portion of the inserter tool of FIG. 38;

FIG. 40 is a perspective view of a proximal portion of the inserter tool of FIG. 38 with the protective member in an open position;

FIG. 41 is another perspective view of a proximal portion of the inserter tool of FIG. 40 and of one embodiment of a mallet;

FIG. 54 is a perspective view of a proximal portion of the inserter tool of FIG. 49 with a locking mechanism of the inserter tool in an unlocked position before striking of a strike cap of the inserter tool;

FIG. 55 is a perspective view of a proximal portion of the inserter tool of FIG. 49 with the locking mechanism of the inserter tool in a locked position;

FIG. 56 is a perspective view of a proximal portion of the inserter tool of FIG. 50 after striking of the strike cap;

FIG. 80 is a perspective view of one embodiment of a tapered helical anchor;

FIG. 81 is an end view of the anchor of FIG. 80;

FIG. 82 is a perspective view of another embodiment of a tapered helical anchor;

FIG. 83 is an end view of the anchor of FIG. 82;

FIG. 84 is a perspective view of yet another embodiment of a tapered helical anchor;

FIG. 85 is an end view of the anchor of FIG. 84;

FIG. 86 is a perspective view of still another embodiment of a tapered helical anchor;

FIG. 87 is an end view of the anchor of FIG. 86;

FIG. 88 is a perspective view of another embodiment of a tapered helical anchor;

FIG. 89 is an end view of the anchor of FIG. 88;

FIG. 90 is a side view of still another embodiment of a tapered helical anchor;

FIG. 91 is an end view of the anchor of FIG. 90;

FIG. 92 is a side view of yet another embodiment of a tapered helical anchor;

FIG. 93 is a perspective view of the anchor of FIG. 92 releasably coupled to the inserter tool of FIG. 1; and FIG. 94 is another perspective view of the anchor of FIG. 92 releasably coupled to the inserter tool of FIG. 1.

DETAILED DESCRIPTION

Figure 1:
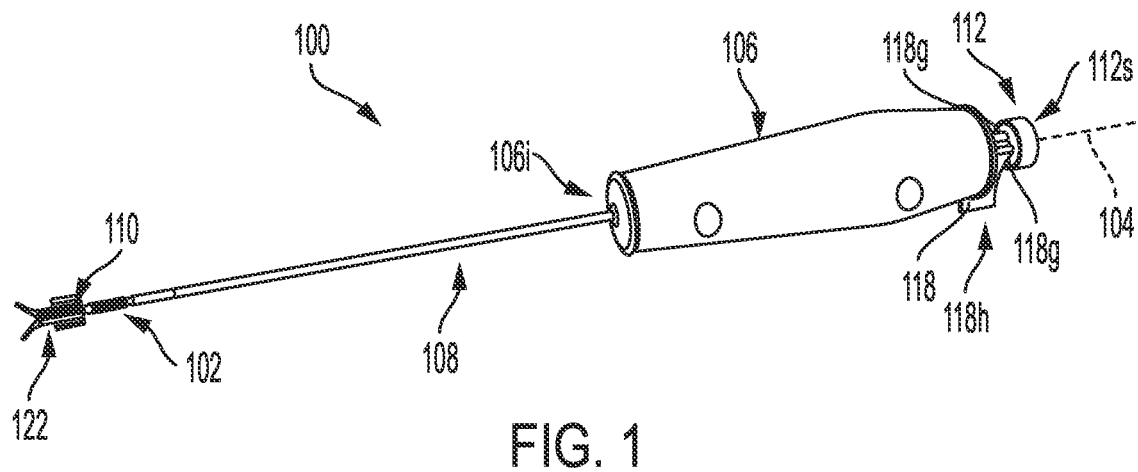
FIG. 1 is a perspective view of one embodiment of an inserter tool and one embodiment of a locking aid coupled to the inserter tool.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary systems and devices for knotless anchor insertion and methods of knotless anchor insertion are provided. In general, an inserter tool is configured for knotless anchor insertion in a soft tissue repair surgical procedure. The inserter tool is configured to insert an anchor into a bone of a patient to secure a soft tissue relative to the bone. A suture coupled to the soft tissue is secured relative to the bone by being trapped between an exterior surface of the anchor and a bone surface defining a hole in the bone in which the anchor is positioned. The anchor therefore allows the suture to be secured in position without needing to be knotted, which can be time consuming and/or difficult to perform during surgery because of small suture diameter, limited working area at a joint space, a wet surgical environment, and/or limited visualization at the surgical site due to challenging angles and the tight nature of the joint space.

The inserter tool is configured to have each of the suture and the anchor releasably coupled thereto and, with the suture and the anchor releasably coupled thereto, to insert each of the suture and the anchor into the bone hole. The inserter tool is configured to position the suture in the bone hole before the anchor is secured in the bone hole. The inserter tool is thus configured to allow the suture to be tensioned relative to the bone and the anchor after the suture has been positioned in the bone hole and before the anchor is secured in the bone hole to fix the suture in position relative to the bone, thereby allowing the soft tissue to be desirably positioned relative to the bone before being secured in position for healing. The inserter tool is configured to advance the anchor into the bone hole by longitudinally translating the anchor in a distal direction into the bone hole, such as by hitting the inserter tool with a mallet, hammer, or other tool, thereby trapping the suture between the exterior surface of the anchor and the bone surface defining the bone hole. After the anchor has been inserted into the bone, the inserter tool is configured to be longitudinally translated in a proximal direction to be removed from the patient's body with the anchor and the suture remaining in the bone. Decoupling the inserter tool from the suture and the anchor by longitudinally translating the inserter tool along its longitudinal axis may be less time consuming and/or may require less user-applied force than other methods of decoupling a tool from an implanted anchor that include rotating the tool about its longitudinal axis. Unlike longitudinally translating the inserter tool for removal, rotating the tool for removal can risk rotating the anchor and/or unintended off axis loading, which can cause the anchor to become less securely positioned in the bone and/or can cause damage to the suture and/or to the anchor.

The suture is releasably coupled to the inserter tool before the inserter tool is advanced into the patient's body. In at least some embodiments, a loading aid is configured to facilitate coupling of the suture and the inserter tool. In general, the loading aid is configured to position the suture in a suture retention channel of the inserter tool. The suture is configured to be slid into the suture retention channel and snap-fit therein using the loading aid. The suture thus need not be fed by a user through an aperture, eyelet, or other opening of the anchor or the inserter tool to be coupled to the inserter tool for insertion into the patient's body. Feeding a suture through an aperture, eyelet, or other opening can, similar to the threading of a needle, be time consuming and/or difficult to perform because of small suture diameter, small opening diameter, and/or a wet surgical environment. The loading aid is configured to properly align the suture with the suture retention channel to facilitate the sliding of the suture into the suture retention channel, which relieves a user of having to align the suture and suture retention channel by direct eye visualization or electronic visualization, which may be time consuming and/or difficult to perform because of small suture diameter, small opening diameter, and/or a wet surgical environment.

The suture retention channel is located distal to the anchor releasably coupled to the inserter tool. The suture seated in the suture retention channel can thus be positioned in the bone hole distal to the anchor, thereby allowing the anchor to be advanced distally into the bone hole with the suture already positioned in the bone hole. In an exemplary embodiment, the suture has a U-shape before and after the anchor is fixed in the bone hole. In the U-shape, each of the suture's legs extend longitudinally along opposed sides of the anchor, and an intermediate portion of the suture that connects the legs extends along the anchor's distal tip so as to loop around the anchor's distal tip. The U-shape configuration of the suture relative to the anchor may maximize a length of the suture that the anchor presses against to fix the suture in position relative to the bone, which may help ensure that the soft tissue coupled to the suture remains in a fixed position relative to the bone to facilitate healing.

The systems, devices, and methods described herein have applicability in a variety of surgical procedures for soft tissue repair, such as in a tissue repair surgical procedure at a joint such as a shoulder, a knee, or a hip.

Figure 2:
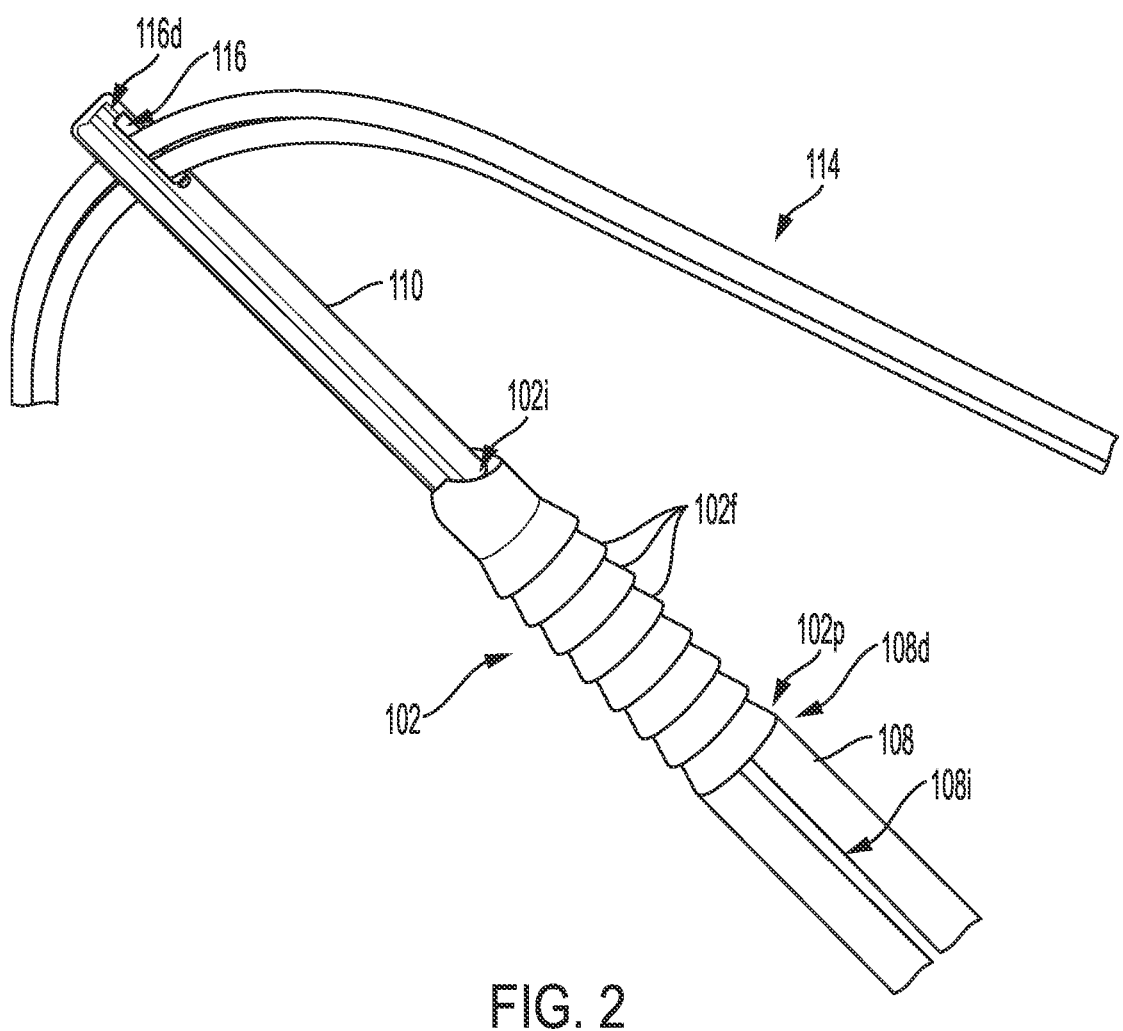
FIG. 2 is a perspective view of a distal portion of the inserter tool of FIG. 1 without the loading aid coupled thereto and with one embodiment of a suture coupled to the inserter tool.

FIG. 1 illustrates one embodiment of an inserter tool 100, also referred to herein as an "inserter," for knotless anchor insertion in a soft tissue repair surgical procedure. In general, the inserter tool 100 is configured to insert an anchor 102 into a bone of a patient to secure a soft tissue relative to the bone. As shown in FIG. 2, an inner lumen 102*i* extends through the anchor 102 such that the anchor 102 is cannulated. A plurality of bone-engaging surface features 102*f* are formed on an exterior surface of the anchor 102. The bone-engaging surface features 102*f* are configured to engage bone to retain the anchor 102 in the bone, e.g., to engage a surface of bone defining the bone hole in which the anchor 102 is positioned. The bone-engaging surface features 102*f* include a plurality of ribs each extending circumferentially around the anchor 102 at different axial positions along the anchor's longitudinal length. The bone-engaging surface features 102f can, however, have another configuration, such as a plurality of barbs or other form of protrusions formed on the anchor's exterior surface. The bone-engaging surface features 102f are also configured to engage a suture against the bone to help secure the suture relative to the bone.

The anchor 102 can be absorbable or non-absorbable. The anchor 102 can be made from any of a variety of materials, e.g., Polyether ether ketone (PEEK), Polylactic acid or polylactide (PLA), BIOCRYL®, BIOCRYL® RAPIDE®, titanium, ceramics, carbon fiber, stainless steel, etc. The anchor 102 can be formed by a variety of techniques, for example by machining, molding, metal injection molding, overmolding, or by a post-molding process such as post-molding machining. Exemplary embodiments of anchors include the Healix Advance™ anchors and the Gryphon® anchor available from DePuy Mitek, Inc. of Raynham, MA, and various exemplary embodiments of anchors and features thereof are further described in U.S. Pat. No. 8,114,128 entitled "Cannulated Suture Anchor" issued Feb. 14, 2012, U.S. Pat. No. 8,882,801 entitled "Dual Thread Cannulated Suture Anchor" issued Nov. 11, 2014, and U.S. Pat. No. 8,133,257 entitled "Bioabsorbable Suture Anchor System For Use In Small Joints" issued Mar. 13, 2012, which are hereby incorporated by reference in their entireties.

The inserter tool 100 includes a handle 106, an outer shaft 108 that extends distally from the handle 106, an inner shaft 110 that extends distally from the handle 106, and a strike cap 112 that extends proximally from the handle 106. The handle 106 is configured to be held by hand during use of the inserter 100. In robotic surgical implementations, the handle 106 can be held by a mechanical member of the robotic surgical system. The handle 106 has a generally cylindrical, distally-tapering shape in this illustrated embodiment but can have any of a variety of shapes. The handle 106 has an inner lumen 106i extending therethrough. The outer and inner shafts 108, 110 are positioned in the inner lumen 106i extend distally out of the inner lumen 106i. Proximal ends of one or both of the outer and inner shafts 108, 110 can be located within the inner lumen 106, or one or both of the outer and inner shafts 108, 110 can extend proximally beyond the handle 106 such that the respective proximal ends of the outer and inner shafts 108, 110 are located proximal to the handle 106. For example, as in this illustrated embodiment, the proximal end of the inner shaft 110 can be attached to the handle 106, and the proximal end of the outer shaft 108, also referred to herein as a "push tube," can be located within the inner lumen 106i of the handle 106. For another example, the proximal end of the inner shaft 110 can be attached to the handle 106, and the proximal end of the outer shaft 108 can be located proximal to the handle 106.

A distal end of the strike cap 112 abuts the proximal end of the push tube 108 in the inserter's initial configuration, which may maximize transmission of a distal force applied to the strike cap 112 to the push tube 108 and thereby help efficiently distally advance the push tube 108 to distally advance the anchor 102 into the bone hole. However, the strike cap's distal end can be spaced a distance proximal to the push tube's proximal end, or the strike cap 112 can be integrally formed with the push tube 108. The strike cap 112 is configured to be struck with a mallet, hammer, or other tool on a proximal surface 11s thereof. The proximal surface 112s is substantially flat in this illustrated embodiment, which may facilitate an even strike on the strike cap 112 and thus an evenly transmitted distal force from the strike cap 112 to the push tube 108. A person skilled in the art will appreciate that a surface may not be precisely flat but nevertheless considered to be substantially flat for any of one or more reasons, such as manufacturing tolerances or sensitivity of measurement equipment. The proximal surface 112s can however, have another shape, e.g., textured with ribs, raised dome protrusions, convex; etc.

An inner lumen 108i extends through the outer shaft 108 such that the outer shaft 108 is cannulated. In an initial configuration of the inserter 100, which is shown in FIGS. 1 and 2, the inner shaft 110 is seated in the inner lumen 102i of the anchor 102 and in the inner lumen 108i of the outer shaft 108. FIG. 2 shows a portion of the outer shaft 108 removed and without the inner shaft 110 therein for clarity of illustrating the outer shaft's tubular configuration in at least this portion of the outer shaft 108. The inner shaft 110 extends distally from the outer shaft 108 and from the anchor 102. A distal end 108d of the outer shaft 108 is located proximal to a proximal end 102p of the anchor 102. In an exemplary embodiment, as shown in FIGS. 1 and 2, the outer shaft's distal end 108d abuts the anchor's proximal end 102p in the inserter's initial configuration, which may maximize transmission of a distal force applied to the push tube 108 to the anchor 102 and thereby help efficiently distally advance the anchor 102 into the bone hole. However, the outer shaft's distal end 108d can be spaced a distance proximal to the anchor's proximal end 102p in the inserter's initial configuration.

As in this illustrated embodiment, a locking mechanism 118 can be configured to be releasably coupled to the inserter tool 100. The locking mechanism 118 is configured to lock the outer shaft 108 in position relative to the inner shaft 110 when the locking mechanism 118 is coupled to the inserter tool 100. The locking mechanism 118 may therefore help prevent premature distal advancement of the outer shaft 108 relative to the inner shaft 110 and thus help prevent premature distal advancement of the anchor 102 relative to the inner shaft 110. The locking mechanism 118 in this illustrated embodiment includes a clip that includes a pair of resilient legs 118g. The resilient legs 118g have a size and shape that allows the legs 118g to seat a distal extension of the strike cap 112 therebetween and to be positioned between a proximal surface of the handle 106 and a distal surface of the strike cap 112. The locking mechanism 118 coupled to the inserter tool 100 therefore prevents the strike cap 112 from moving distally relative to the handle 106 and thus also prevents a strike on the strike cap 112 from pushing the push tube 108 distally until the locking mechanism 118 is removed from the inserter tool 100. The locking mechanism 118 is configured to be removed from the inserter tool 100 by gripping a handle portion 118h of the locking mechanism 118 and pulling the locking mechanism 118 away from the inserter 100, which causes the resilient legs 118g to flex radially outward and release the strike cap 112 therefrom.

As shown in FIG. 2, with the inserter 100 in the initial configuration, a suture 114 releasably coupled to the inserter 100 has a U-shape. As discussed above, the suture 114 having the U-shape before anchor 102 insertion into the bone hole allows for the suture 114, after anchor 102 insertion into the bone hole, to have each of the suture's two legs 114g extending longitudinally along opposed sides of the anchor 102, and an intermediate portion 114i of the suture 114 that connects the legs 114g extending along the anchor's distal tip 102t so as to loop around the anchor's distal tip 102t. As also shown in FIG. 3, the suture 114 includes two suture strands in this illustrated embodiment but can include another number of suture strands, e.g., one, three, four, etc.

Figure 3:
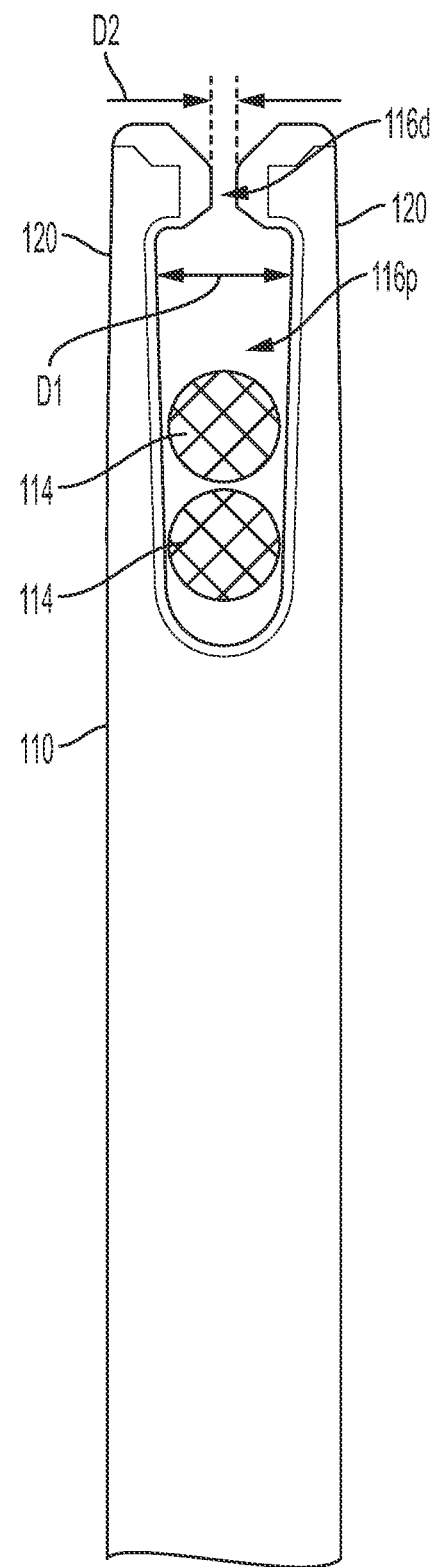
FIG. 3 is a side, partial cross-sectional view of the suture and a distal portion of the inserter tool of FIG. 2.

As shown in FIGS. 2 and 3, the inner shaft 110 includes a notch formed therein that defines a suture retention channel 116. The notch is formed in a distal end of the inner shaft 110 and is defined by opposed distal arms 120 of the inner shaft 110. A proximal portion 116p of the suture retention channel 116 is configured to seat the suture 114 therein. The proximal portion 116p of the suture retention channel 116 has an open distal end and a closed proximal end that defines the suture retention channel's proximal end. A distal portion 116d of the suture retention channel 116 extends distally from the proximal portion 116p of the suture retention channel 116. The distal portion 116d of the suture retention channel 116 has an open proximal end and has an open distal end that defines the suture retention channel's distal end. The suture retention channel 116 thus has a closed proximal end and an open distal end. The suture retention channel 116 is configured to receive the suture 114 therein through the suture retention channel's open distal end. The suture 114 can then move through the distal portion 116d of the suture retention channel 116 to be positioned in the proximal portion 116p of the suture retention channel 116. The proximal portion 116p of the suture retention channel 116 has a diameter D1 that is greater than a diameter D2 of the distal portion 116d of the suture retention channel 116, which may help retain the suture 114 in the suture retention channel 116 by discouraging, if not preventing, the suture 114 from moving distally out of the suture retention channel 116 before a desired time of suture 114 decoupling from the inserter tool 100.

The distal arms 120 of the inner shaft 110 are configured to spring back and forth relative to one another, similar to tweezer arms. The movement of the distal arms 120 relative to one another is configured to change the diameter D2 of the distal portion 116d of the suture retention channel 116 to facilitate seating of the suture 114 in the suture retention channel 116 and removal of the suture 114 from the suture retention channel 116. FIGS. 2 and 3 show the arms 120 in a resting configuration in which the diameter D2 of the distal portion 116d of the suture retention channel 116 is at a minimum. The arms 120 are configured to move from the resting configuration to an expanded configuration in which the arms 120 are moved radially outward such that the suture retention channel 116 becomes larger with the diameter D2 of the distal portion 116d of the suture retention channel 116 increasing from the diameter D1 in a least a distal portion of the suture retention channel's distal portion 116d. The expanded diameter D2 of the distal portion 116d provides more space for the suture 114 to enter into the suture retention channel 116. The arms 120 are biased to the resting configuration such that the arms 120 are configured to dynamically move from the resting configuration to the expanded configuration in response to the suture 114 being advanced proximally into the suture retention channel 116, such that the arms 120 are configured to dynamically move from the expanded configuration to the resting configuration in response to the suture 114 being advanced proximally out of the distal portion 116d and into the proximal portion 116p of the suture retention channel 116, and such that arms 120 are configured to dynamically move from the resting configuration to the expanded configuration in response to the suture 114 being advanced distally out of the proximal portion 116p into the distal portion 116d and then out of the suture retention channel 116.

The suture retention channel 116 may allow for more sutures and/or larger diameter suture(s) to be coupled to the inserter 100 than with other types of inserter tools since the suture(s) do not need to be folded over to be inserted into an aperture, eyelet, or other opening to be coupled to the inserter tool or to the anchor.

As shown in FIGS. 1 and 2, the suture retention channel 116 is located distal to the anchor 102 releasably coupled to the inserter tool 100. The suture 114 seated in the suture retention channel 116 can thus be positioned in the bone hole distal to the anchor 102, thereby allowing the anchor 102 to be advanced distally into the bone hole with the suture already positioned in the bone hole.

The suture 114 is positioned in the suture retention channel 116 by a user of the inserter tool 100, which may provide a user of the inserter 100 flexibility in deciding on a size and type of suture 114 to use that is appropriate for a particular patient and a particular surgical procedure. The suture 114 can be positioned in the suture retention channel 116 by the user by hand, similar to the threading of a needle. Alternatively to hand positioning, the suture 114 can be positioned in the suture retention channel 116 using a tool such as a pusher tube or a loading aid. One embodiment of a loading aid 122 is illustrated in FIGS. 1 and 4.

A distal portion of the inner shaft 110 including the arms 120 can be made from a shape memory or superelastic material, such as Nitinol or other material, which may facilitate movement of the arms 120 between the resting configuration and the expanded configuration. The resting configuration can be the default shape of the arms 120. In some embodiments, the only portion of the inner shaft 110 made from a shape memory or superelastic material can include the arms 120. In other embodiments, only a distal portion of the inner shaft 110 that extends distally from the outer shaft 108 can be made from a shape memory or superelastic material. In other embodiments, only a distal portion of the inner shaft 110 that extends distally to the anchor 102 an be made from a shape memory or superelastic material.

Figure 4:
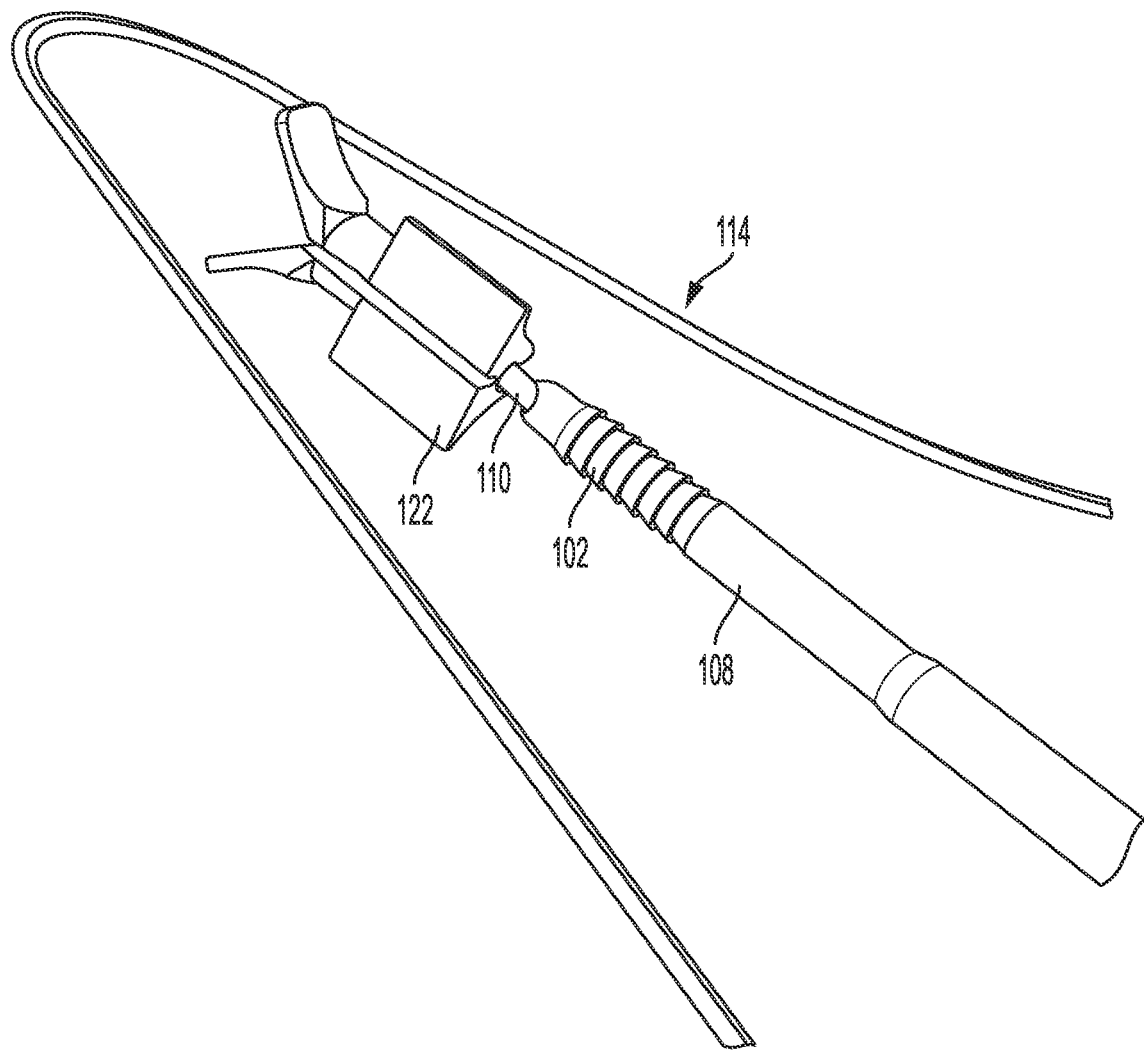
FIG. 4 is a perspective view of a distal portion of the inserter tool of FIG. 1 with the suture of FIG. 2 not yet coupled to the inserter tool.

FIGS. 1 and 4 illustrate the loading aid 122 positioned relative to the inserter tool 100 before the suture 114 is positioned in the suture retention channel 116. The loading aid 122 is positioned over a distal end of the inserter tool 100 and in particular over a distal end of the inner shaft 110. The loading aid 122 is directly coupled to the inner shaft 110 in this illustrated embodiment but can be indirectly coupled to the inner shaft 110, such as by being directly coupled to another part of the inserter 100 such as the outer shaft 108 or directly coupled to the anchor 102 that has the inner shaft 110 seated in the inner lumen 102i of the anchor 102. In an exemplary embodiment, the loading aid 122 is pre-loaded on the inserter tool 100 during manufacturing, which may help ensure that the loading aid 122 is positioned correctly on the inserter 100 and/or may provide a reminder to a user of the inserter 100 that the suture 114 should be coupled to the inserter 100 before the inserter 100 is advanced into a patient's body. Alternatively, the loading aid 122 can be loaded onto the inserter tool 100 by a user, which may allow for the inserter 100 to be sold without the loading aid 122 and thus at a lower cost than the inserter 100 sold with the loading aid 122.

Figure 5:
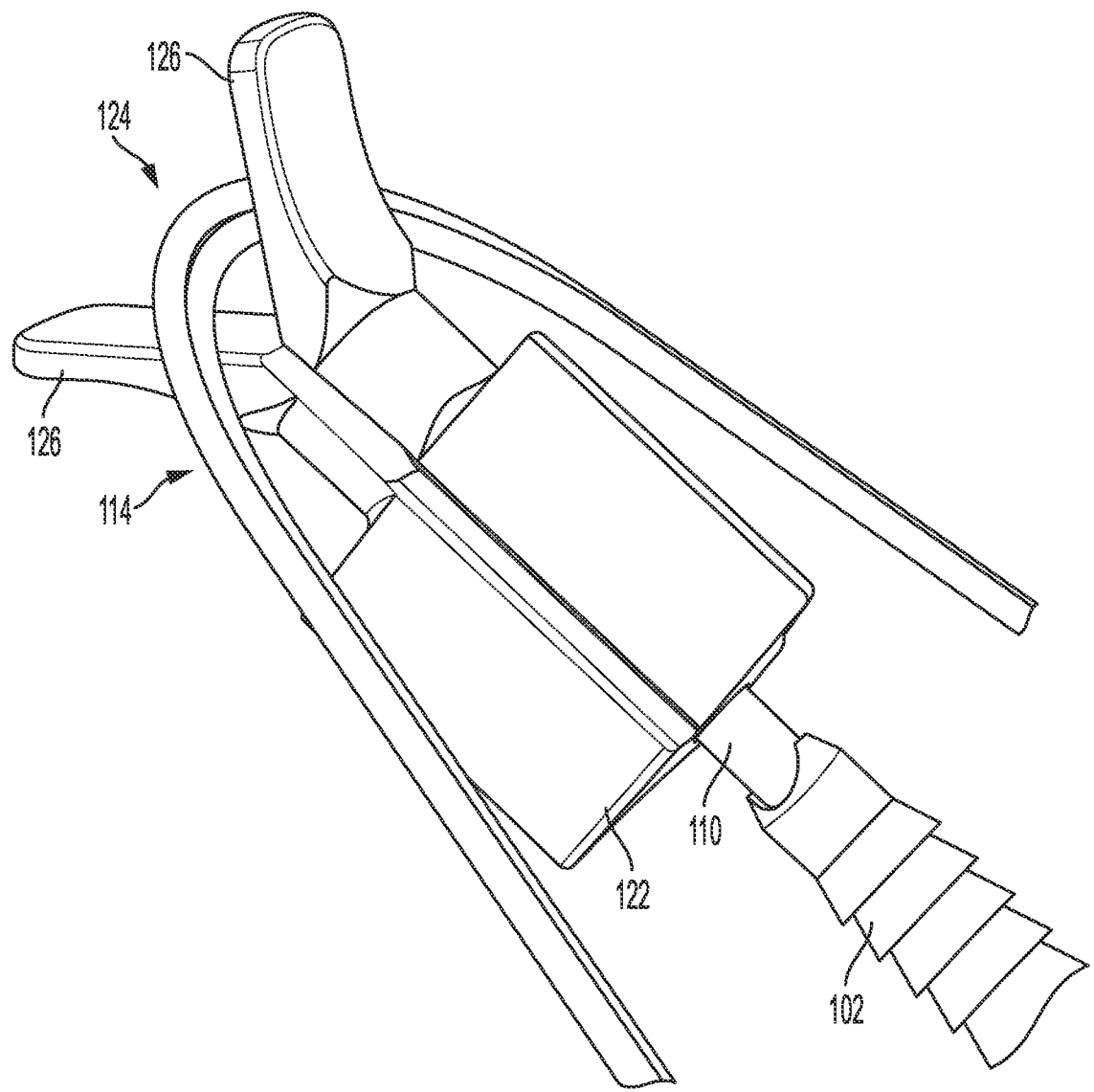
FIG. 5 is a perspective view of a distal portion of the inserter tool of FIG. 4 with the suture positioned in a distal seating groove of the loading aid.
Figure 6:
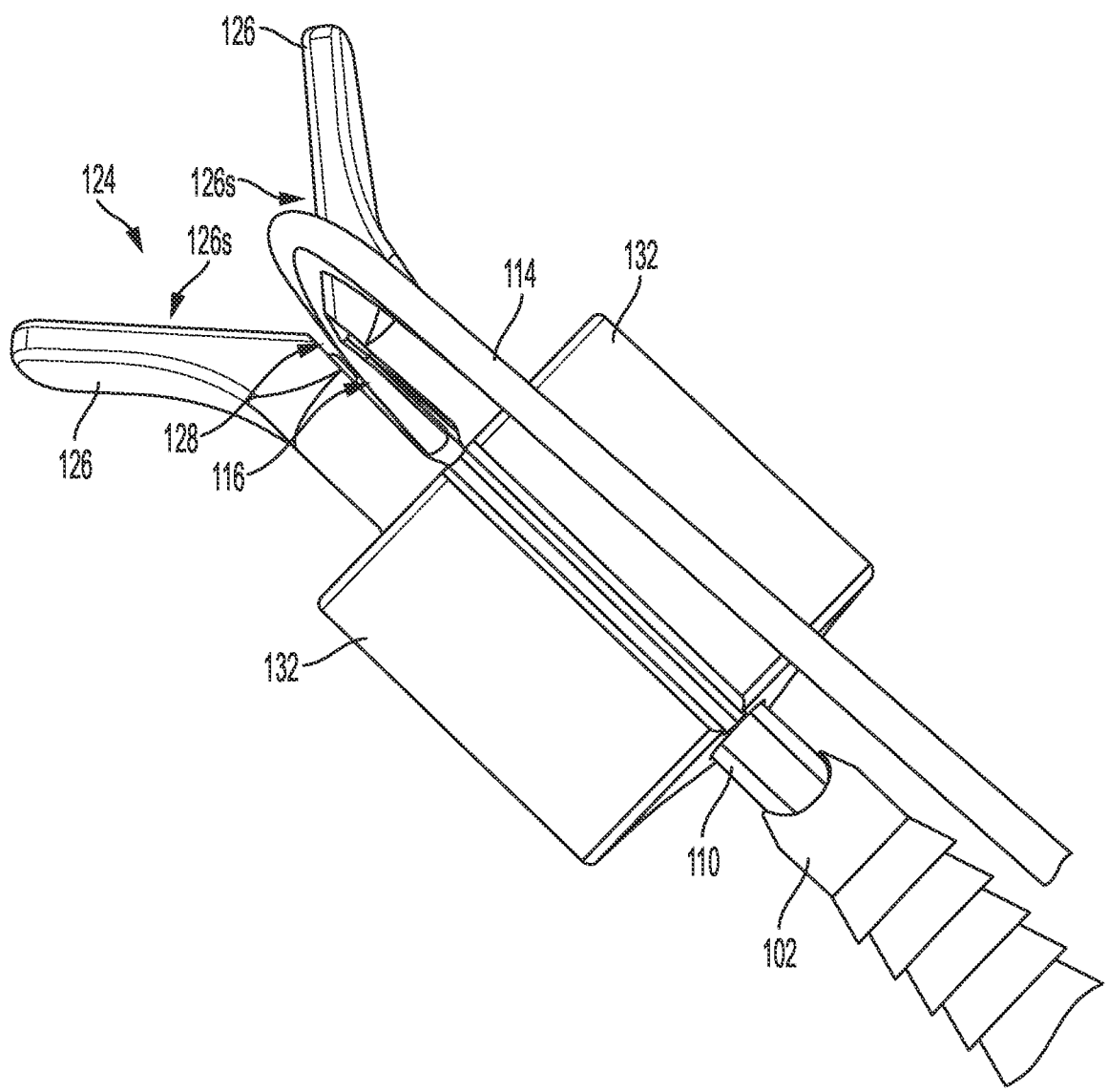
FIG. 6 is another perspective view of the inserter tool, the loading aid, and the suture of FIG. 5.
Figure 7:
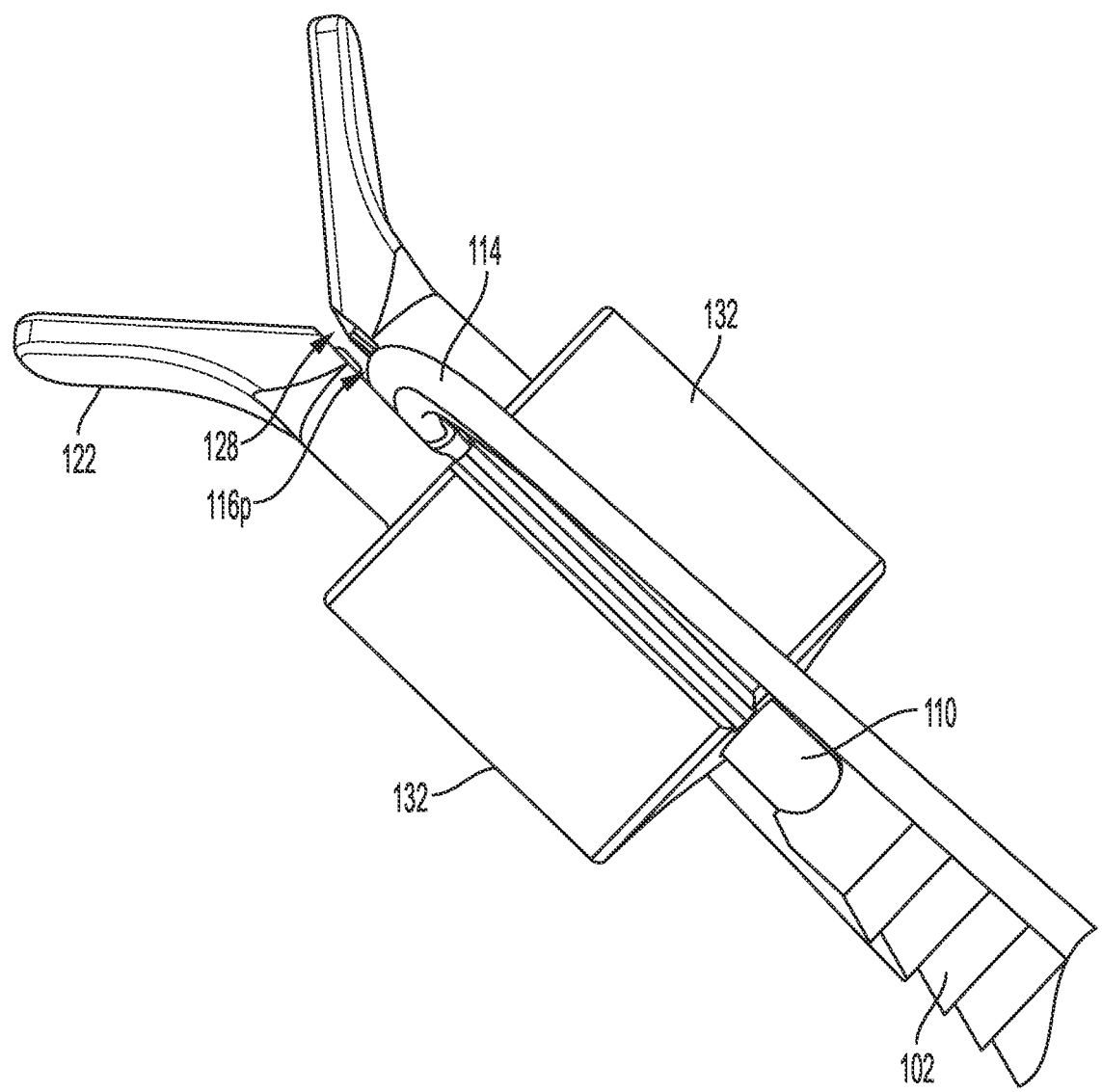
FIG. 7 is a perspective view of a distal portion of the inserter tool of FIGS. 5 and 6 with the suture positioned in a loading channel of the loading aid.
Figure 8:
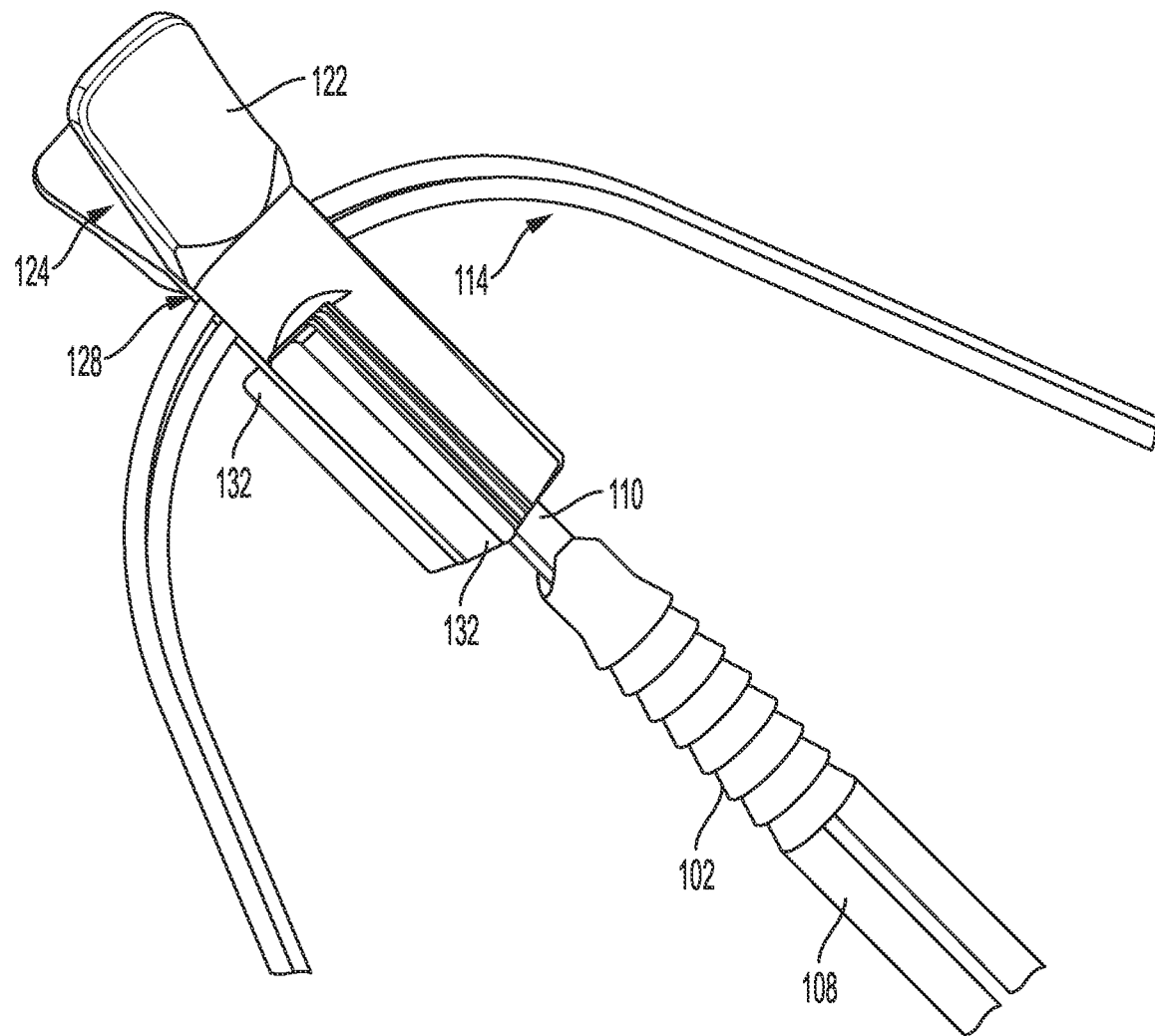
FIG. 8 is another perspective view of the inserter tool, the loading aid, and the suture of FIG. 7.
Figure 9:
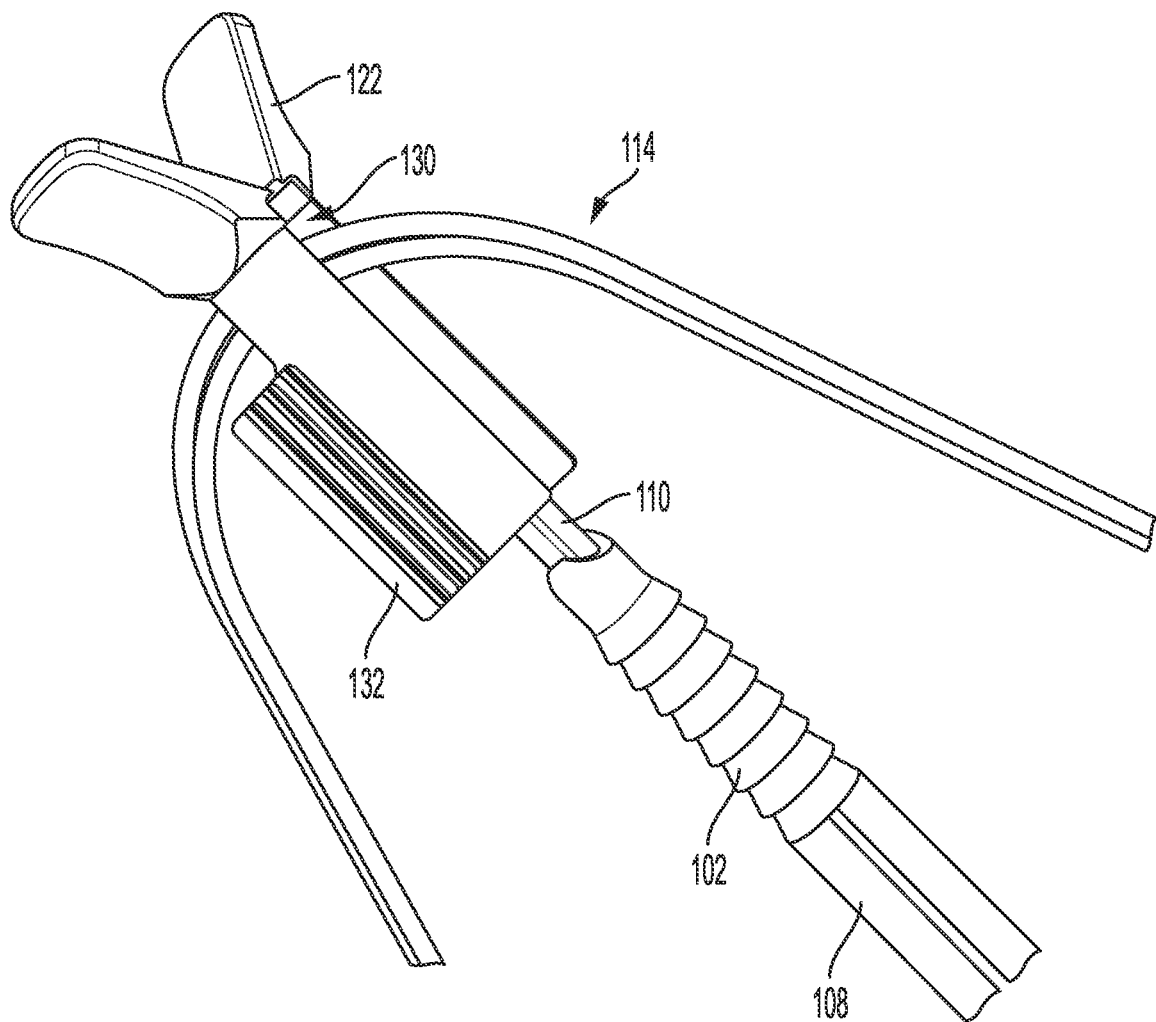
FIG. 9 is a perspective view of a distal portion of the inserter tool of FIGS. 7 and 8 with the suture positioned in a release channel of the loading aid and in a suture retention channel of the inserter tool.

As shown in FIG. 5, the suture 114 is positioned within a distal seating groove 124 of the loading aid 122. The distal seating groove 124 is defined by opposed distal wings 126 of the loading aid 122. The distal wings 126 each extend radially outward so as to define a V-shape. The distal seating groove 124 is thus V-shaped. The distal seating groove 124 is located distal to the inner shaft's suture retention channel 116. The suture 114 is then, as shown in FIG. 6, positioned on an inner surface 126s of one of the distal wings 126 and slid proximally along the distal wing's inner surface 126s to guide the suture 114 to an apex of the distal seating groove 124, e.g., to the point of the V-shape. The suture 114 can be slid along either of the distal wing's inner surface 126s. The suture 114 continues to be slid proximally to enter a longitudinal loading channel 128 of the loading aid 122. The loading channel 128 is aligned with the suture retention channel 116. Thus, sliding of the suture 114 within the loading channel 128 in a proximal direction causes the suture 114 to enter the suture retention channel 116 and, in particular, the distal portion 116d thereof. Continued movement of the suture 114 in a proximal direction within the loading channel 128 and the suture retention channel 116 causes the suture 114 to be seated in the proximal portion 116p of the suture retention channel 116, as shown in FIGS. 7-9. The closed proximal end of the suture retention channel 116 acts as a stop surface for the suture 114 in the suture retention channel 116, although in some embodiments the suture 114 may be positioned in the proximal portion 116p but not abut the stop surface. As discussed above, the distal arms 118 of the inner shaft 110 can be splayed radially outward as the suture 114 passes into and through the distal portion 116d and can splay radially inward to their resting position after the suture 114 exits the distal portion 116d and enters the proximal portion 116p.

Figure 10:
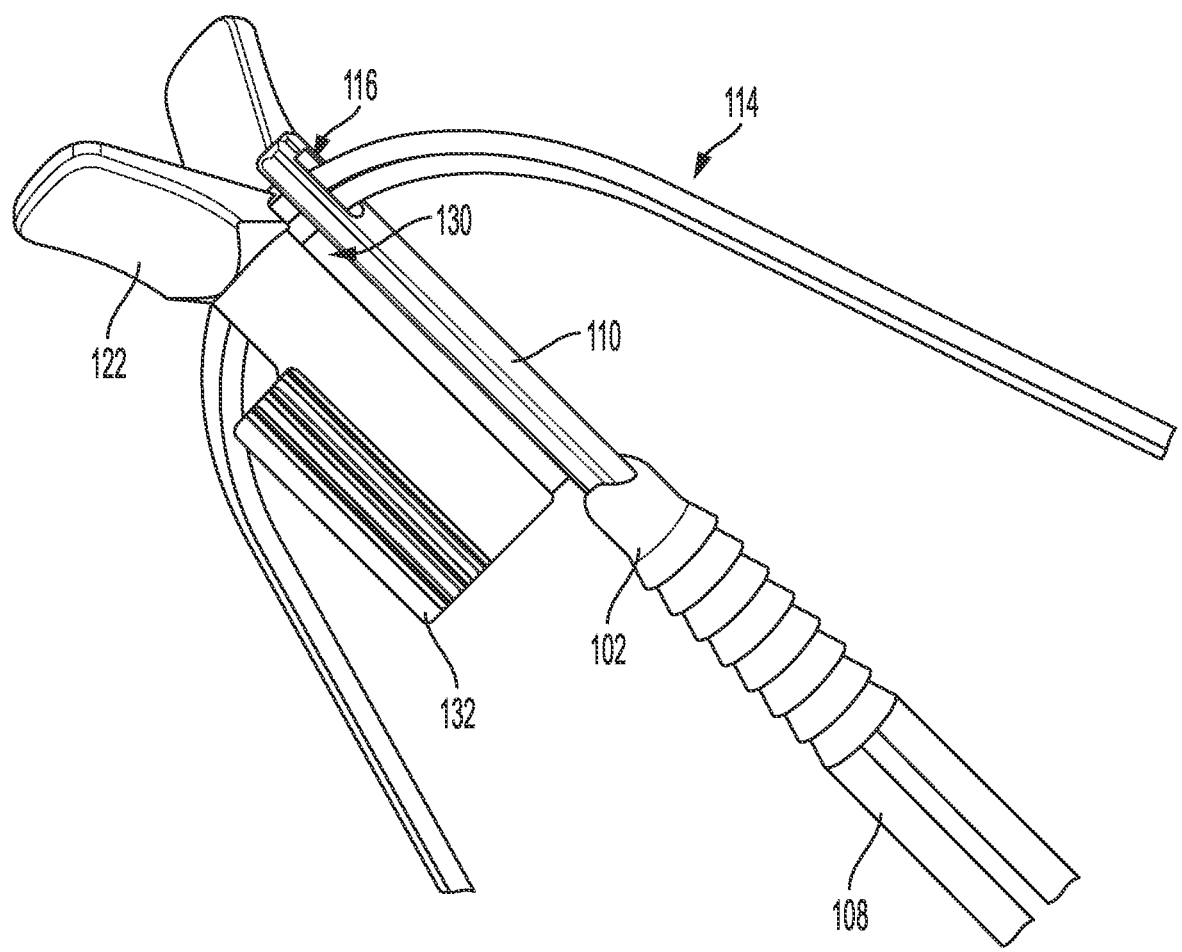
FIG. 10 is a perspective view of a distal portion of the inserter tool of FIG. 9 with the loading aid being removed from the inserter tool and the suture.

As shown in FIG. 9, the loading aid 122 includes a longitudinal release channel 130 located on an opposite side of the loading aid 122 from the longitudinal loading channel 128. The suture 114 also enters the release channel 130 when the suture 114 is slid proximally to enter the loading channel 128. The suture 114 also moves proximally in the release channel 130 when the suture 114 is slid further proximally in the loading channel 128 to enter the proximal portion 116p of the suture retention channel 116. The release channel 130 is configured to facilitate release of the loading aid 122 from the inserter tool 100. As shown in FIG. 10, lateral movement of the loading aid 122 relative to the inserter 100 (or vice versa) causes the inserter 100, e.g., the inner shaft 110 thereof, to move through the release channel 130 so as to release the loading aid 122 from the inserter 100. The suture 114 also moves through the release channel 130 during the loading aid's removal from the inserter 100. FIGS. 2 and 3 illustrate the inserter 100 with the loading aid 122 removed from the inserter 100 and with the suture 114 positioned in the suture retention channel 116.

Sliding the suture 114 along the distal wing's inner surface 126s toward the loading channel 128 may help ensure that the suture 114 properly enters the loading channel 128 and thus that the suture 114 properly enters the suture retention channel 116, but the suture 114 need not slide along either distal wing's inner surface 126s before entering the loading channel 128.

Instead of the suture 114 sliding relative to the loading aid 122 with the loading aid 122 held in position by hand, the suture 114 can be held by hand with the loading aid 122 being moved relative thereto to cause the suture 114 to be positioned as described above. In an exemplary embodiment, the loading aid 122 is held in position by hand and the suture 114 moved relative thereto. The loading aid 122 includes opposed finger holds 132 configured to provide a surface easily held by hand during use of the loading aid 122. By including finger holds 132 on opposed sides of the loading aid 122, the loading aid 122 may be conveniently held by a left hand or a right hand and be in an easily held position regardless of the loading aid's rotational position relative to the user. One of both of the finger holds 132 may be held at a time.

With the suture 114 coupled to the inserter 100, and with the loading aid 122 removed from the inserter 100 if the loading aid 122 was coupled to the inserter 100 to facilitate suture coupling thereto, the inserter 100 can be used to insert the suture 114 and the anchor 102 into a bone hole. In an exemplary embodiment of using the inserter 100 to insert the suture 114 and the anchor 102 into a bone hole, a drill or other bone removal tool is inserted into a patient's body to form the bone hole, as will be appreciated by a person skilled in the art. The drill or other bone removal tool can be advanced into the patient's body, and then removed from the patient's body, through a cannula positioned within an opening, e.g., an incision, formed in the patient's skin, as will also be appreciated by a person skilled in the art. The cannula can then serve as a guide for the inserter's distal advancement toward the bone hole.

The inserter 100 is advanced distally into the body of the patient and positioned with the distal end of the inner shaft 110 within the bone hole. The suture 114 is thus positioned in the bone hole before the anchor 102 is secured in the bone hole. A bottom surface of the bone hole can act as a stop surface that stops distal movement of the inserter 100 relative to the bone. An interior of the bone hole cannot be visualized with the inserter 100 positioned in the bone hole, so the bottom surface of the bone hole acting as a stop can help ensure that the inserter 100 has been advanced as far as distally possible within the bone hole, which may help ensure that the anchor 102 is secured in the bone hole with the anchor's proximal end flush or sub-flush with a proximal end of the bone hole. Alternatively, the inserter 100 can be inserted into the bone hole only a specified distance prior to a distal end of the anchor 102 engaging an open proximal end of the bone hole. As the anchor 102 is not readily advanced into the bone hole without impacting the strike cap 112, the distance the inserter 100 protrudes from the anchor 102 controls the distance that the inserter 100 will advance into the bone hole.

With the distal end of the inner shaft 110 positioned in the bone hole, and prior to distal advancement of the anchor 102 relative to the inner shaft 110, the suture 114 can be tensioned as desired. Alternatively, the suture 114 tension can be approximated prior to placement of the inserter 100 into the bone hole, with the advancement of the inserter 100 into the bone hole adding tension approximately equal to a length of the inserter's distance protruding from the distal end of the anchor 102. A person skilled in the art will appreciate that values may not be precisely equal but nevertheless considered to be approximately equal for any of one or more reasons, such as manufacturing tolerances or sensitivity of measurement equipment.

With the distal end of the inner shaft 110 positioned in the bone hole, the locking mechanism 118 is removed from the inserter 100. The outer shaft 108 is now free to move relative to the inner shaft 110 in response to a strike on the strike cap 112.

With the distal end of the inner shaft 110 positioned in the bone hole, the anchor 102 is advanced distally into the bone hole by longitudinally translating the anchor 102 relative to the inner shaft 110 in a distal direction. In other words, the anchor 102 is pushed axially along the longitudinal axis 104 of the inserter 100. The strike cap 112 is hit with a mallet, hammer, or other tool to cause the outer tube 108 to move distally relative to the inner shaft 110, which causes the anchor 102 to move distally relative to the inner shaft 110 and advance distally into the bone hole. The strike cap 112 may be hit one or more times to fully advance the anchor 102 into the bone hole. The anchor 102 in the bone hole traps the suture 114, e.g., the legs 114g thereof, between the exterior surface of the anchor 102 and the bone surface defining the bone hole.

After the anchor 102 has been inserted into the bone hole, the inserter 100, including the outer and inner shafts 108, 110, is longitudinally translated in a proximal direction, e.g., pulled axially along the longitudinal axis 104 of the inserter 100, to be removed from the patient's body with the anchor 102 and the suture 114 remaining in the bone. The suture 114 automatically exits the inner shaft's suture retention channel 116 in response to the proximal pulling of the inner shaft 110 out of the bone hole. Tails of the suture 114 can be trimmed as desired.

Figure 11:
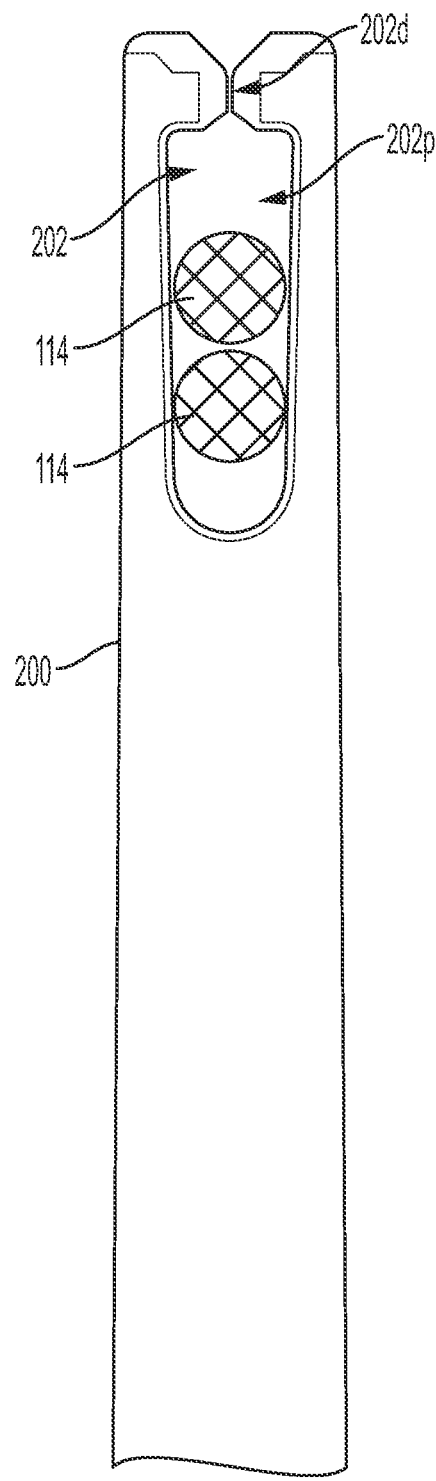
FIG. 11 is a side, partial cross-sectional view of the suture of FIG. 2 and a distal portion of another embodiment of an inserter tool.

FIG. 11 illustrates another embodiment of an inner shaft 200 of an inserter tool. The inner shaft 200 is configured and used similar to the inner shaft 110 of the inserter tool 100 of FIG. 1 except that the inner shaft's suture retention channel 202 has a narrower distal portion 202d defined by the inner shaft's distal arms 204 as compared to the distal portion 116p of the suture retention channel 116. In general, the narrower a distal portion of a suture retention channel, the less likely that a suture positioned in the suture retention channel will prematurely exit the suture retention channel through the distal portion, e.g., through the open distal end thereof. FIG. 11 shows the suture 114 positioned in a proximal portion 202p of the suture retention channel 202.

Figure 12:
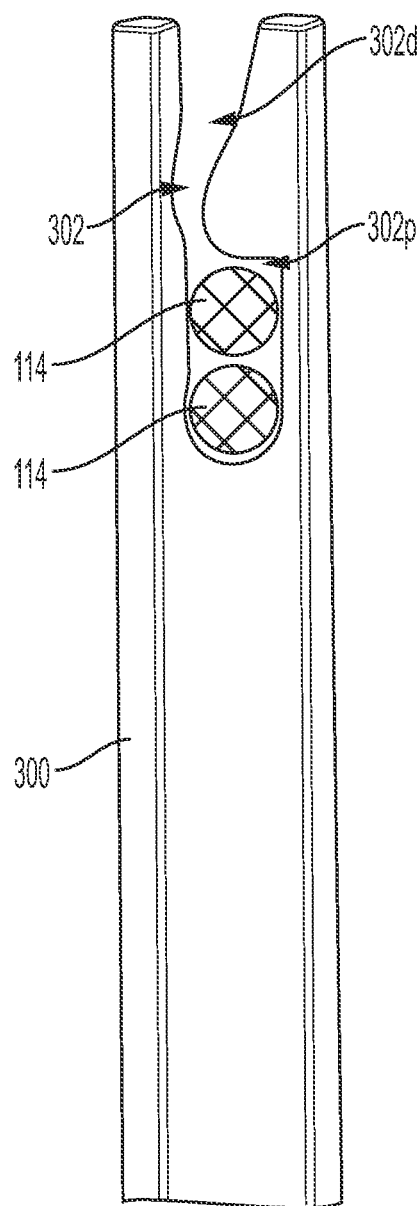
FIG. 12 is a side, partial cross-sectional view of the suture of FIG. 2 and a distal portion of yet another embodiment of an inserter tool.
Figure 13:
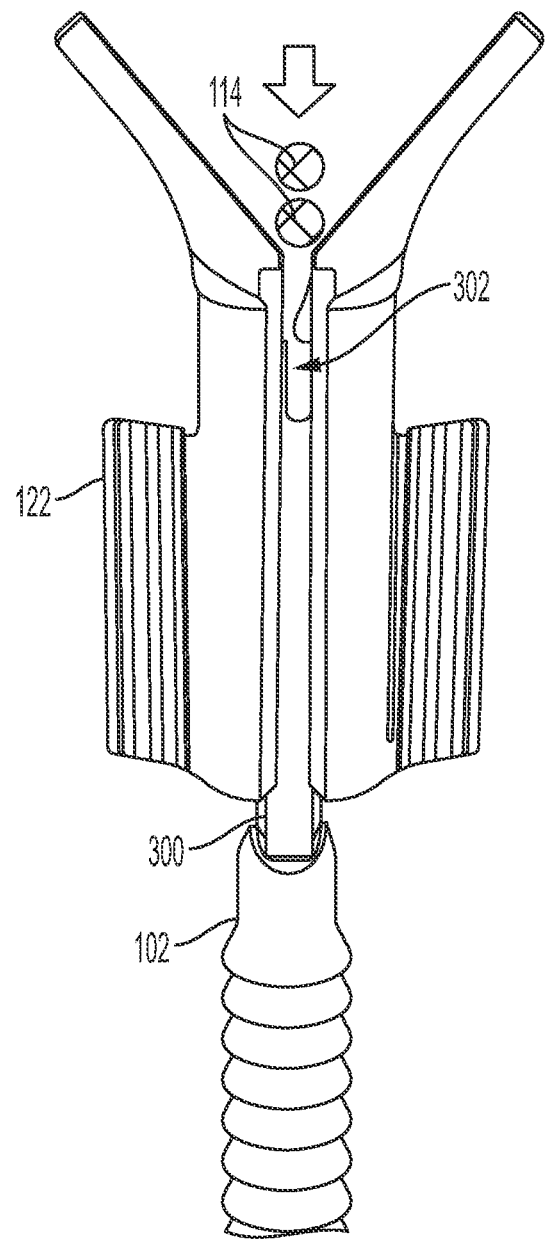
FIG. 13 is a side, partial cross-sectional view of the suture of FIG. 12 and a distal portion the inserter tool of FIG. 12 with the loading aid of FIG. 1 coupled thereto.

FIGS. 12 and 13 illustrates another embodiment of an inner shaft 300 of an inserter tool. In this illustrated embodiment, the inner shaft 300 is configured and used similar to the inner shaft 110 of the inserter tool 100 of FIG. 1 except that the inner shaft's suture retention channel 302 does not have a longitudinal distal portion like the distal portion 116p of the suture retention channel 116. Instead, the suture retention channel's distal portion 302d is a tortuous channel that follows a tortuous path. The tortuous path makes it less likely that a suture positioned in the suture retention channel 302 will prematurely exit the suture retention channel 302 through the distal portion 302d, e.g., through the open distal end thereof. FIG. 12 shows the suture 114 positioned in a proximal portion 302p of the suture retention channel 302. FIG. 13 shows the loading aid 122 coupled to the inner shaft 300 to aid seating of the suture 114 in the suture retention channel 302.

Figure 16:
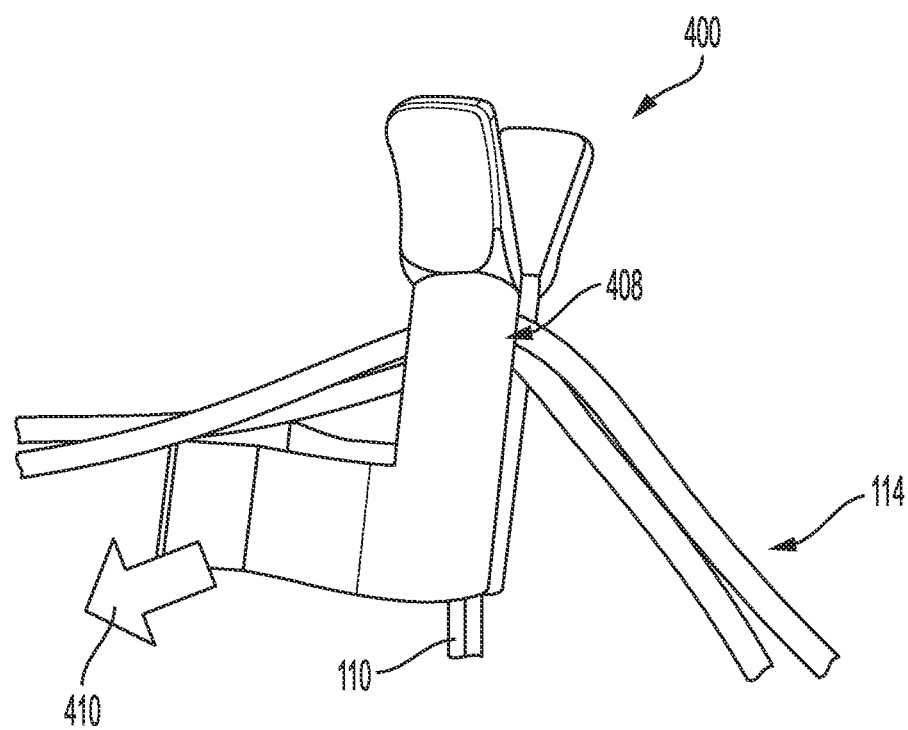
FIG. 16 is a perspective view of the loading aid and the inserter tool of FIG. 15 with the suture positioned in a release channel of the loading aid and in the suture retention channel of the inserter tool.

FIGS. 14-16 illustrate another embodiment of a loading aid 400. The loading aid 400 is shown in FIGS. 14-16 in use with the outer and inner shafts 108, 110 of FIG. 1, with the suture 114 of FIG. 2, and with another embodiment of an anchor 402 but can be similarly used with other outer and inner shafts and other anchors. In this illustrated embodiment, the loading aid 400 is configured and used similar to the loading aid 122 of FIG. 1 except that opposed finger holds 404 of the loading aid 400 extend farther laterally outward than the opposed finger holds 132 of the loading aid 122. FIG. 14 shows the loading aid 400 positioned relative to the inner shaft 110 before the suture 114 is positioned in the suture retention channel 116. FIG. 15 shows the suture 114 positioned in a V-shaped distal seating groove 404 of the loading aid 400. An arrow 406 in FIG. 15 illustrates a proximal direction of movement for the suture 114 to move into the suture retention channel 116. FIG. 16 shows the suture 114 seated in the suture retention channel 116 and in a longitudinal loading channel 408 of the loading aid 400. An arrow 410 in FIG. 16 indicates a direction in which the loading aid 400 can be moved relative to the inner shaft 116 to remove the loading aid 400 therefrom.

Figure 17:
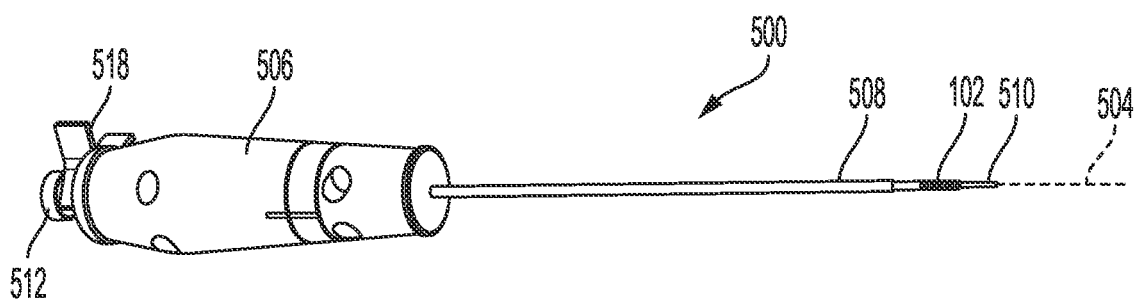
FIG. 17 is a perspective view of still another embodiment of an inserter tool.
Figure 18:
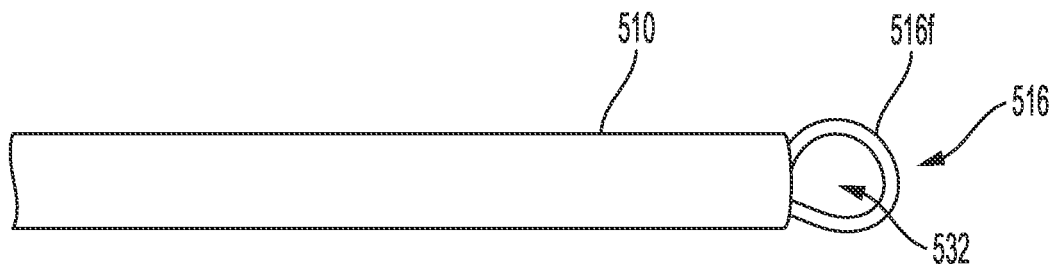
FIG. 18 is a side view of a distal portion of the inserter tool of FIG. 17.

FIG. 17 illustrates another embodiment of an inserter tool 500 for knotless anchor insertion in a soft tissue repair surgical procedure. The inserter tool 500 is generally configured and used similar to the inserter tool 100 of FIG. 1, e.g., is configured to insert an anchor into a bone of a patient to secure a soft tissue relative to the bone and includes a handle 506, an outer shaft 508 that extends distally from the handle 506, an inner shaft 510 that extends distally from the handle 506, and a strike cap 512 that extends proximally from the handle 506. However, in this illustrated embodiment, the inner shaft 510 does not include a notch or suture retention channel. Instead, the inserter tool 510 includes a snare configured to seat a suture therein. As shown in FIG. 18, the snare is defined by a loop 516 of a flexible member 516f. A "flexible member" is also referred to herein as a "pliable member." The flexible member 516f is configured to fold or bend without breaking, cracking, or otherwise losing structural integrity. The flexible member 516f is a metal single filament wire in this illustrated embodiment but can have other configurations, e.g., a metal multi-filament wire, a braided fabric, a textile strand, a monofilament fiber, etc. In some embodiments, the flexible member 516f can be made from a shape memory or superelastic material, such as Nitinol or other material.

The loop 516 is located distal to the inner shaft 510 and is thus located distal to the anchor 102 that has the inner shaft 510 positioned in the inner lumen 102i thereof. The loop 516 has a horseshoe shape and has one end fixedly attached to the inserter 500 and has one end that is free so as to not be fixedly attached to the inserter 500. The end of the flexible member 516f fixedly attached to the inserter 500 is fixedly attached to an outer shaft 508 of the inserter 500 in this illustrated embodiment but can be attached to another portion of the inserter 500. The loop 516 defines an enclosed passage 532 in cooperation with the distal end of the inner shaft 510. A suture is configured to be seated in the loop 516, e.g., extend through the passage 532, during use of the inserter tool 500, similar to that discussed above regarding the suture retention channel 116 and as discussed further below. The free end of the loop 516 can extend through the inner shaft 510 and out of the handle 506 to allow a user to tension the flexible member 516f and thereby adjust a size of the passage 532. The handle 506 can include a suture retention member, e.g., a slot formed in the handle 506 and configured to releasably retain the suture by seating the suture therein in a cinch or pinch, a protrusion around which the suture can be tied or wrapped, etc., to allow the tension on the flexible member 516f to be maintained and thus for the loop 516 size to be maintained. Embodiments of suture retention members are discussed further below.

The anchor 102 shown in FIG. 17 is the same anchor 102 as shown in FIG. 1, but other anchors can be similarly used with the inserter tool 500.

As in this illustrated embodiment, a locking mechanism 518 can be configured to be releasably coupled to the inserter tool 500 to lock the outer shaft 508 in position relative to the inner shaft 510 when the locking mechanism 518 is coupled to the inserter tool 500. The locking mechanism 518 is generally configured and used similar to the locking mechanism 118 of FIG. 1.

The suture is positioned in the loop 516 by a user of the inserter tool 500, which may provide a user of the inserter 500 flexibility in deciding on a size and type of suture to use that is appropriate for a particular patient and a particular surgical procedure. The suture can be positioned in the loop 516 by the user by hand, similar to the threading of a needle. Alternatively to hand positioning, the suture can be positioned in the loop 516 using a loading aid 522, illustrated in FIG. 19. In embodiments in which the suture is positioned in the loop 516 by a user of the inserter tool 500, the user can manually adjust a size of the loop 516 as desired to help position the suture in the loop 516 by pulling on the flexible member 516f, e.g., to move a length of the flexible member 516f out of the inner shaft 510 to increase a size of the loop 516, or pushing on the flexible member 516f, e.g., to move a length of the flexible member 516f into the inner shaft 510 to decrease a size of the loop 516.

Figure 19:
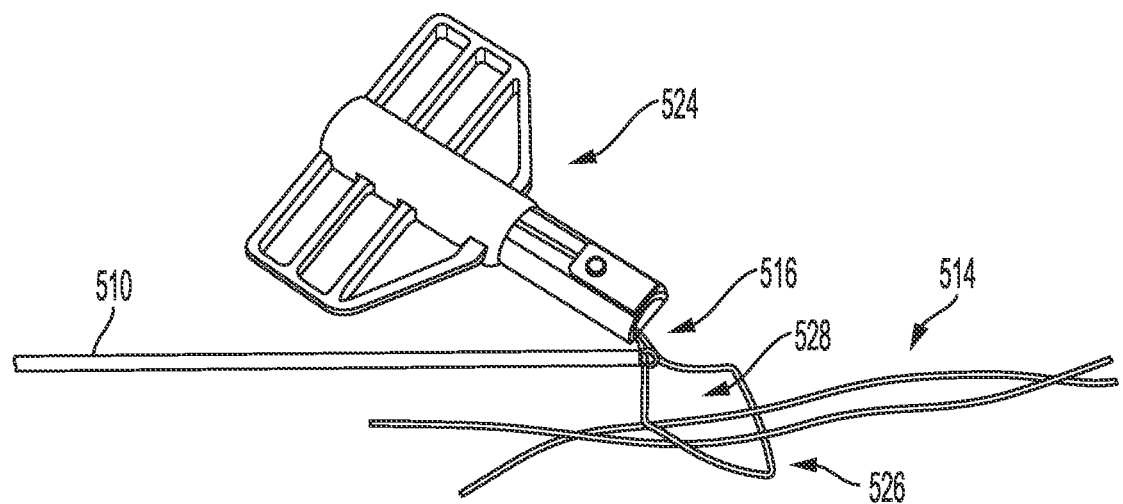
FIG. 19 is a side view of a distal portion of the inserter tool of FIG. 17, another embodiment of a suture, and another embodiment of a loading aid.

The loading aid 522 in this illustrated embodiment includes a suture threader. A suture threader can have a variety of configurations, as will be appreciated by a person skilled in the art. In this illustrated embodiment, the loading aid 522 includes a base 524 and a wire loop 526 that is attached to the base 524, that extends distally from the base 524, and that defines an enclosed passage 528. The wire loop 526 is formed by a metal single filament wire in this illustrated embodiment but can have other configurations, similar to the loop 516 discussed above. A suture 514 is configured to be seated in the passage 528 defined by the loop 526, as shown in FIG. 19. The suture 514 is generally configured and used similar to the suture 114 of FIG. 2 and, similar to that discussed above regarding the suture 114, includes two strands in this illustrated embodiment but can include another number of strands. The suture 514 can be coupled to the loading aid 522 by a user, which may provide a user of the inserter 500 flexibility in deciding on a size and type of suture to use that is appropriate for a particular patient and a particular surgical procedure and/or may allow for the inserter 500 to be sold without the loading aid 522 and thus at a lower cost than the inserter 500 sold with the loading aid 522.

Figure 20:
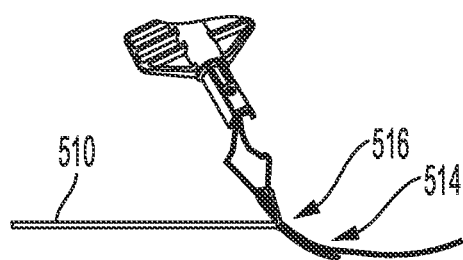
FIG. 20 is a side view of a distal portion of the inserter tool, the loading aid, and the suture of FIG. 19 with the suture positioned in a loop of the inserter tool and in an enclosed passage of the loading aid.
Figure 21:
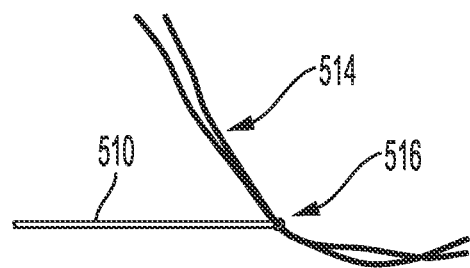
FIG. 21 is a side view of a distal portion of the inserter tool and the suture of FIG. 20 with the suture positioned in a loop of the inserter tool and with the loading aid removed.

With the suture 514 extending through the loop 526 of the loading aid 522, the loading aid 522 can be pulled by the base 524 to pull the suture 514 through the snare, e.g., through the loop 516 defined by the flexible member 516f, as shown in FIG. 20, so as to thread the suture 514 through the snare. The suture 514 can then be released from the loading aid 522 by being removed from the passage 528 defined by the loop 526. FIG. 21 illustrates the suture 514 released from the loading aid 522 and extending through the loop 516 defined by the flexible member 516f. The suture 514 extending through the loop 516 can thus be releasably coupled to the inserter 500 and have a U-shape with the inserter 500 in its initial configuration, similar to that discussed above regarding the suture 114 and the inserter 100 of FIG. 2.

With the suture 514 coupled to the inserter 500, and with the loading aid 522 removed from the suture 514 if the loading aid 522 was used to facilitate suture coupling to the inserter 500, the inserter 500 can be used to insert the suture 514 and the anchor 102 into a bone hole. In an exemplary embodiment of using the inserter 500 to insert the suture 514 and the anchor 102 into a bone hole, a drill or other bone removal tool is inserted into a patient's body to form the bone hole, similar to that discussed above regarding the inserter 100 of FIG. 1.

The inserter 500 is advanced distally into the body of the patient and positioned with the distal end of the inner shaft 510 within the bone hole and thus with the loop 516 within the bone hole. The suture 514 that extends through the loop 516 is thus positioned in the bone hole before the anchor 102 is secured in the bone hole. A bottom surface of the bone hole can act as a stop surface that stops distal movement of the inserter 500 relative to the bone, similar to that discussed above regarding the inserter 100 of FIG. 1.

With the distal end of the inner shaft 510 positioned in the bone hole, and prior to distal advancement of the anchor 102 relative to the inner shaft 510, the suture 514 can be tensioned as desired.

With the distal end of the inner shaft 510 positioned in the bone hole, the locking mechanism 518 is removed from the inserter 500. The outer shaft 508 is now free to move relative to the inner shaft 510 in response to a strike on the strike cap 512.

With the distal end of the inner shaft 510 positioned in the bone hole, the anchor 102 is advanced distally into the bone hole by longitudinally translating the anchor 102 relative to the inner shaft 510 in a distal direction by striking the strike cap 512 to distally advance the push tube 508, similar to that discussed above regarding the inserter 100 of FIG. 1. The anchor 102 in the bone hole traps the suture 514 between the exterior surface of the anchor 102 and the bone surface defining the bone hole.

Figure 22:
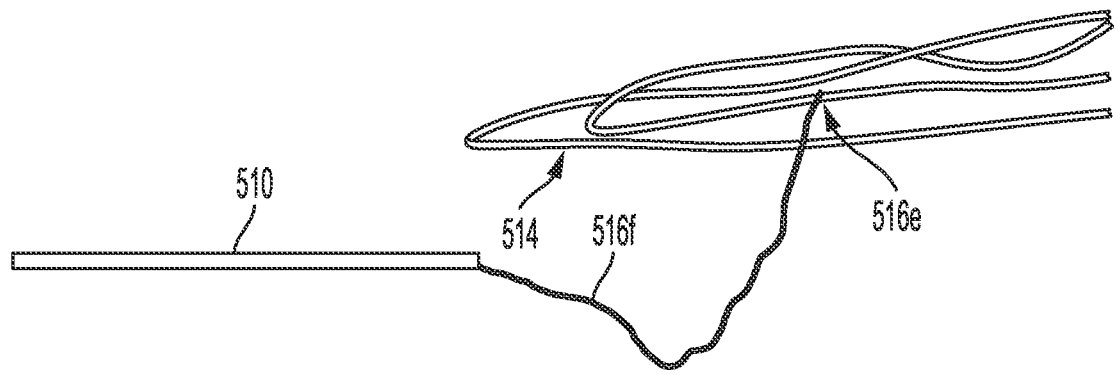
FIG. 22 is a side view of a distal portion of the inserter tool and the suture of FIG. 21 with the loop opened.

After the anchor 102 has been inserted into the bone hole, the inserter 500 is longitudinally translated in a proximal direction, e.g., pulled axially along a longitudinal axis 504 of the inserter 500, to be removed from the patient's body with the anchor 102 and the suture 514 remaining in the bone. The proximal movement of the inserter 500 causes the snare to unfold itself due to one of the flexible member's ends being free and the other of the flexible member's ends being fixedly attached to the inserter 500. The end of the flexible member 516f attached to the inserter 500 moves proximally with the inserter 500 while the free end of the flexible member 516f slides within the inserter 500 until the free end of the flexible member 516f exits the open distal end of the inner shaft 510 such that the loop 516 is open and no longer exists as a loop. Continued proximal movement of the inserter 500 causes the entire flexible member 516f to exit the patient's body along with the inserter 500. With the loop 516 being open and no longer being present, the suture 514 is freed from the flexible member 516f and can thus stay fixed in position in the bone hole. Tails of the suture 514 can be trimmed as desired. Although not showing the suture 514 positioned in a bone hole, FIG. 22 illustrates the snare in its unfolded configuration and also shows the free end 516e of the flexible member 516f.

The snare in the illustrated embodiment of FIG. 17 is a passive snare in which the suture 514 extends through the loop 516 of the flexible member 516f and is freely slidable through the loop 516 until the anchor 502 fixes the suture 514 in position relative to the bone. In other embodiments, the snare can be an active snare in which the snare securely engages the suture in a loop of a flexible member such that the suture extending through the loop is not freely slidable through the loop before or after the anchor fixes the suture in position relative to the bone.

Figure 23:
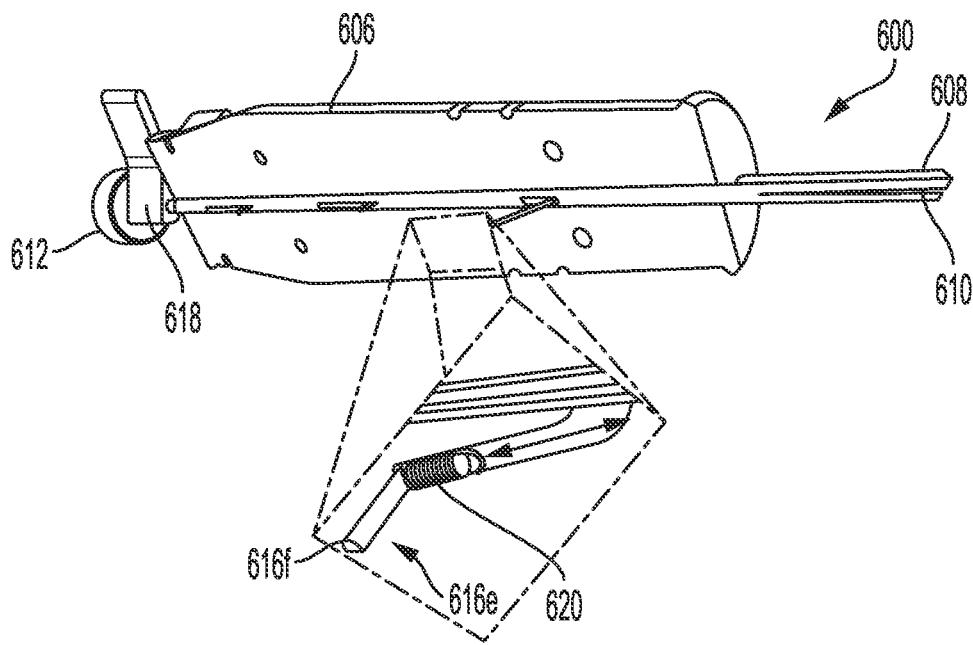
FIG. 23 is a side cross-sectional view of a proximal portion of another embodiment of an inserter tool.

FIG. 23 illustrates another embodiment of an inserter tool 600 for knotless anchor insertion in a soft tissue repair surgical procedure. The inserter tool 600 is generally configured and used similar to the inserter tool 500 of FIG. 17, e.g., is configured to insert an anchor into a bone of a patient to secure a soft tissue relative to the bone and includes a handle 606, an outer shaft 608 that extends distally from the handle 606, an inner shaft 610 that extends distally from the handle 606, a strike cap 612 that extends proximally from the handle 606, and a snare defined by a loop of a flexible member 616f. However, in this illustrated embodiment, the snare is an active snare. The flexible member 616f is a textile strand in this illustrated embodiment but can have other configurations, e.g., a metal multi-filament wire, a braided fabric, a metal single filament wire, etc.

The loop defined by the flexible member 616f is generally configured and used similar to the loop 516 defined by the flexible member 516f, e.g., is located distal to the inner shaft 610 and is thus located distal to the anchor that has the inner shaft 610 positioned in an inner lumen thereof, has a horseshoe shape, and has one end 616e fixedly attached to the inserter 600 and has one end that is free so as to not be fixedly attached to the inserter 600. However, in this illustrated embodiment, the end 616e of the flexible member 616f fixedly attached to the inserter 600 is spring-loaded. The fixed end 616e of the flexible member 616f is operatively coupled to a spring 620 that is fixedly attached to the handle 606. The spring 620 is a coil spring in this illustrated embodiment but can be another type of spring or bias member. The spring 620 is configured to bias the flexible member 616f in a proximal direction, e.g., in a direction toward the handle 606. The spring 620 is thus configured to self-tension the loop on a suture passed through the loop. The suture may therefore be held in a known, fixed position relative to the inner shaft 610, which may help ensure the anchor engages an adequate length of each suture leg trapped between the anchor and bone. The user can manually increase a size of the loop as desired to help position the suture in the loop by pulling on the flexible member 616f, e.g., to move a length of the flexible member 616f out of the inner shaft 610 to increase a size of the loop before the user releases the flexible member 616f to allow the spring 620 to tension the flexible member 616f on the suture extending through the loop. The suture can be positioned in the loop defined by the flexible member 616f by the user by hand, or the suture can be positioned in the loop defined by the flexible member 616f using a loading aid, e.g., the loading aid 522 of FIG. 19.

Similar to that discussed above, the free end of the loop defined by the flexible member 616f can extend through the inner shaft 610 and out of the handle 606 to allow a user to tension the flexible member 616f and thereby adjust a size of the loop. The handle 606 can include a suture retention member, e.g., a slot formed in the handle 606 and configured to releasably seat the suture therein in a cinch or pinch, a protrusion around which the suture can be tied or wrapped, etc., to allow the tension on the flexible member 616f to be maintained and thus for the loop size to be maintained.

As in this illustrated embodiment, a locking mechanism 618 can be configured to be releasably coupled to the inserter tool 600 to lock the outer shaft 608 in position relative to the inner shaft 610 when the locking mechanism 618 is coupled to the inserter tool 600. The locking mechanism 618 is generally configured and used similar to the locking mechanism 118 of FIG. 1.

Figure 24:
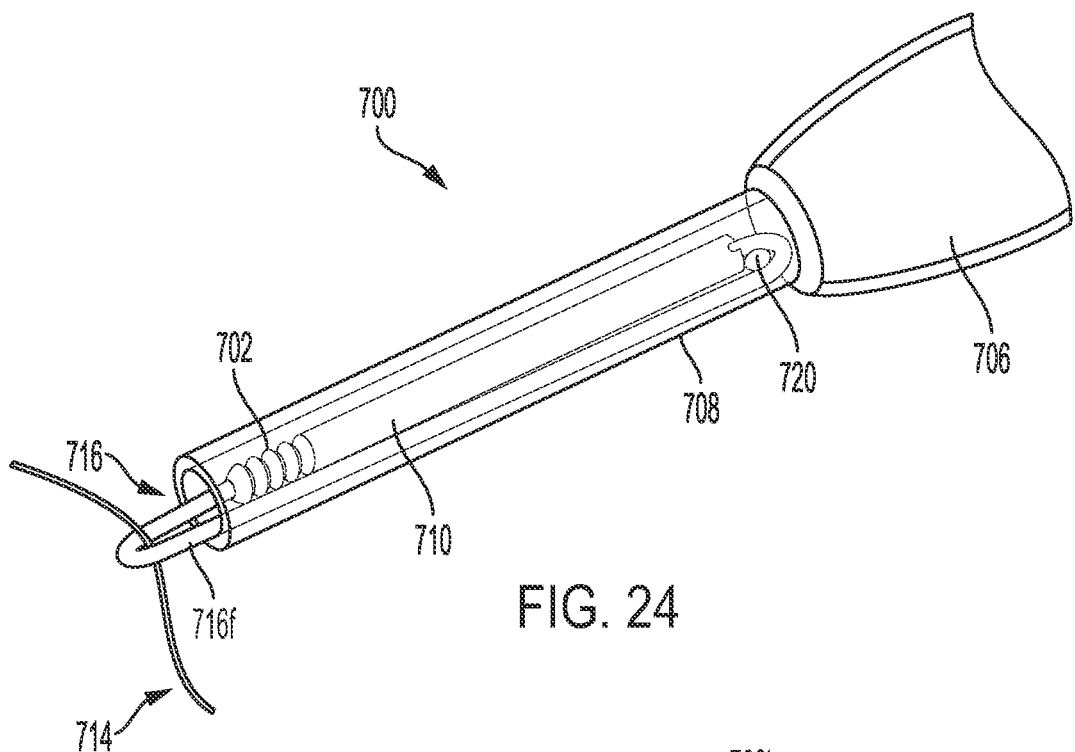
FIG. 24 is a perspective, partially transparent view of a distal portion of yet another embodiment of an inserter tool.

FIG. 24 illustrates another embodiment of an inserter tool 700 for knotless anchor insertion in a soft tissue repair surgical procedure. The inserter tool 700 is generally configured and used similar to the inserter tool 600 of FIG. 23, e.g., is configured to insert an anchor 702 into a bone of a patient to secure a soft tissue relative to the bone and includes a handle 706, an outer shaft 708 that extends distally from the handle 706, an inner shaft 710 positioned inside the outer shaft 708, a strike cap that extends proximally from the handle 706, and a snare that is active and that is defined by a loop 716 of a flexible member 716f. A locking mechanism may be used. The loop 716 defined by the flexible member 716f is generally configured and used similar to the loop defined by the flexible member 616f, e.g., is located distal to the inner shaft 710 and is thus located distal to the anchor 702, has a horseshoe shape, and has one end 716e fixedly attached to the inserter 700 and has one end 716r that is free so as to not be fixedly attached to the inserter 700. However, in this illustrated embodiment, the fixed end 716e of the flexible member 716f is fixedly attached to the inner shaft 710 and loops around a pulley 720 located proximal to the inner shaft 710. The pulley 720 in this illustrated embodiment is fixedly attached to an inner wall of the outer shaft 708 but can be in another location, such as in the handle 706. The fixed end 716e of the flexible member 716f is fixedly attached to the inner shaft 710 at a proximal surface thereof, e.g., by crimping, welding, tying, etc., but can be attached to another portion of the inner shaft 710. The flexible member 716f is a metal single filament wire in this illustrated embodiment but can have other configurations, e.g., a metal multi-filament wire, a braided fabric, a textile strand, etc.

Figure 25:
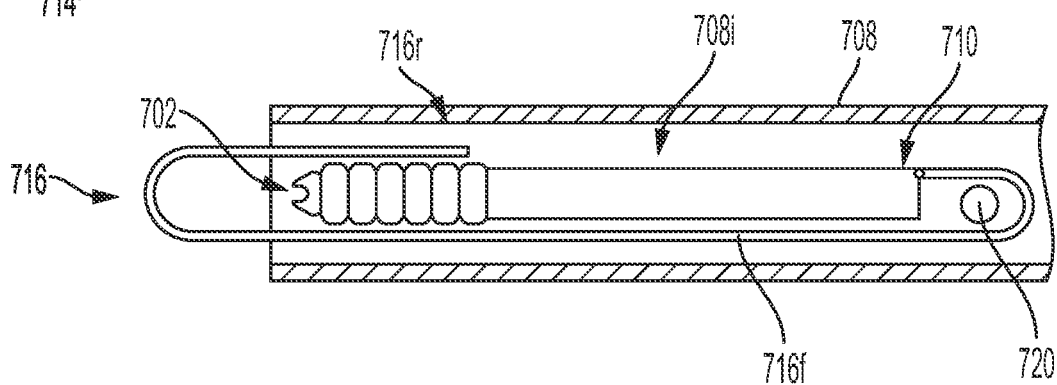
FIG. 25 is a side, partially cross-sectional view of a distal portion of the inserter tool of FIG. 24.
Figure 26:
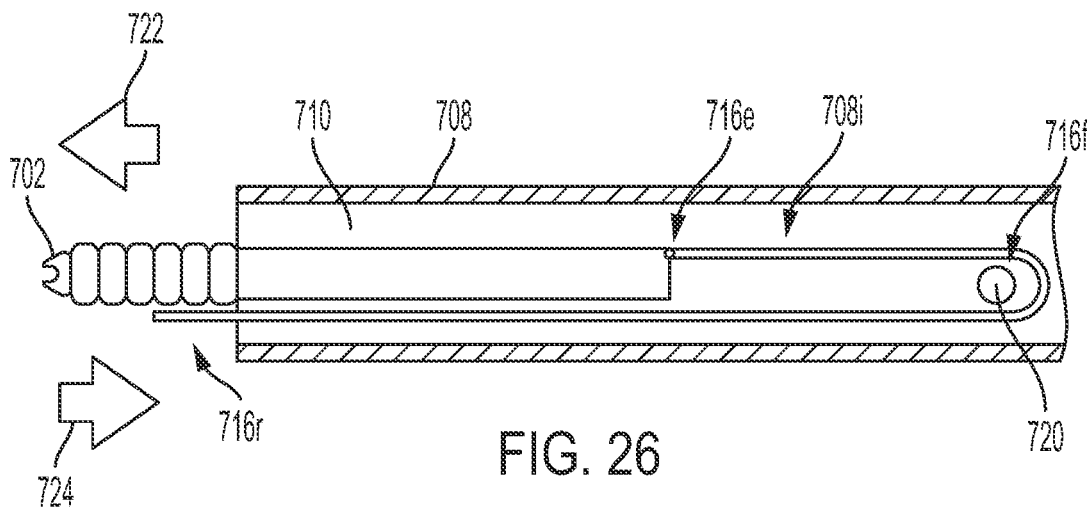
FIG. 26 is a side, partially cross-sectional view of a distal portion of the inserter tool of FIG. 25 with an anchor distally advanced therefrom.

With the inserter 700 in an initial configuration, which is shown in FIGS. 24 and 25, the anchor 702 is disposed in an inner lumen 708i of the outer shaft 708. The inner shaft's distal end 708d abuts the anchor's proximal end 702p in the inserter's initial configuration. The inner shaft 710 in this illustrated embodiment is thus configured to be pushed distally relative to the outer shaft 708, e.g., by striking the strike cap, to cause the anchor 702 to advance distally out of the outer shaft 708 to be implanted in bone. The distal advancement of the inner shaft 710 relative to the outer shaft 708 causes the flexible member 716f to move around the pulley 720 and for the snare to unfold until the free end 716r of the flexible member 716f exits an open distal end of the outer shaft 708 such that the loop 716 no longer exists, as shown in FIG. 26. A first arrow 722 in FIG. 26 illustrates the distal movement of the anchor 702 and the inner shaft 710, and a second arrow 724 in FIG. 26 illustrates the simultaneous proximal movement of the flexible member 716f into the outer shaft's inner lumen 708i as the flexible member 716f moves around the pulley 720.

The embodiments of the inserter tools 100, 500, 600, 700 discussed above with respect to FIGS. 1, 11, 12, 17, 23, and 24 are each configured to insert an anchor and a suture into a bone of a patient that remain in the bone after the inserter tool has been removed from the patient's body. In other embodiments, an inserter tool can be configured to insert an anchor, a suture, and a distal cap into a bone of a patient that remain in the bone after the inserter tool has been removed from the patient's body. In such embodiments, a flexible member need not be used to define a loop for a suture to pass through because a suture can instead pass through an enclosed passage defined by the distal cap and the inserter tool's inner shaft.

Figure 27:
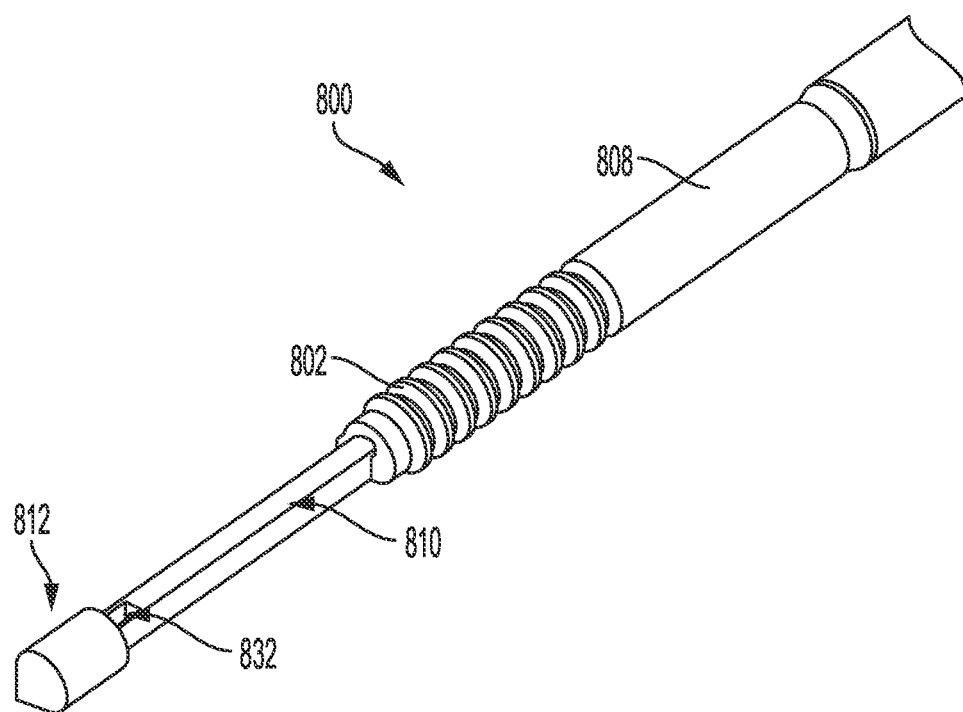
FIG. 27 is a perspective view of a distal portion of still another embodiment of an inserter tool.

FIG. 27 illustrates another embodiment of an inserter tool 800 for knotless anchor insertion in a soft tissue repair surgical procedure. The inserter tool 800 is generally configured and used similar to the inserter tool 100 of FIG. 1, e.g., is configured to insert an anchor 802 into a bone of a patient to secure a soft tissue relative to the bone and includes a handle, an outer shaft 808 that extends distally from the handle, an inner shaft 810 that extends distally from the handle, and a strike cap that extends proximally from the handle. A locking mechanism may be used. The anchor 802 is generally configured and used similar to the anchor 102 of FIG. 1.

Figure 28:
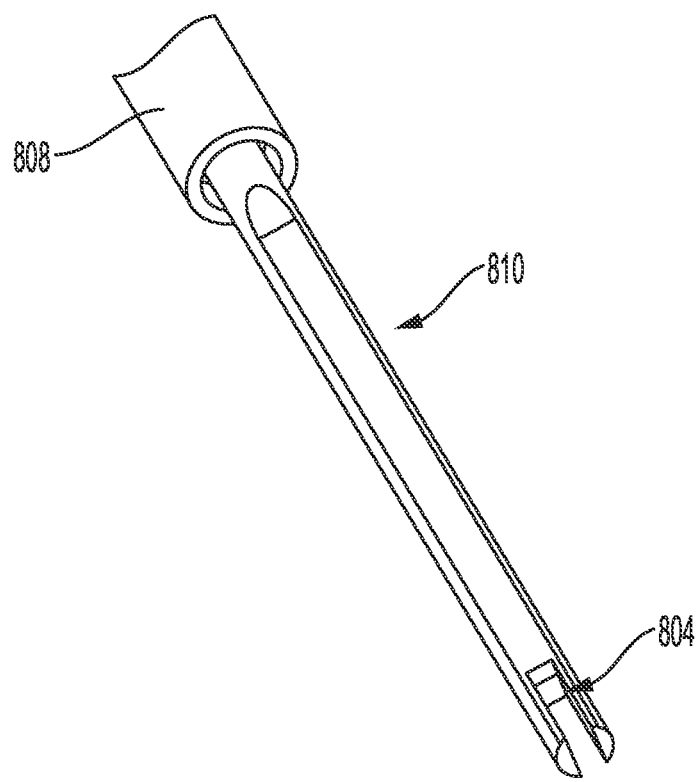
FIG. 28 is a perspective view of distal portion of inner and outer shafts of the inserter tool of FIG. 27.
Figure 29:
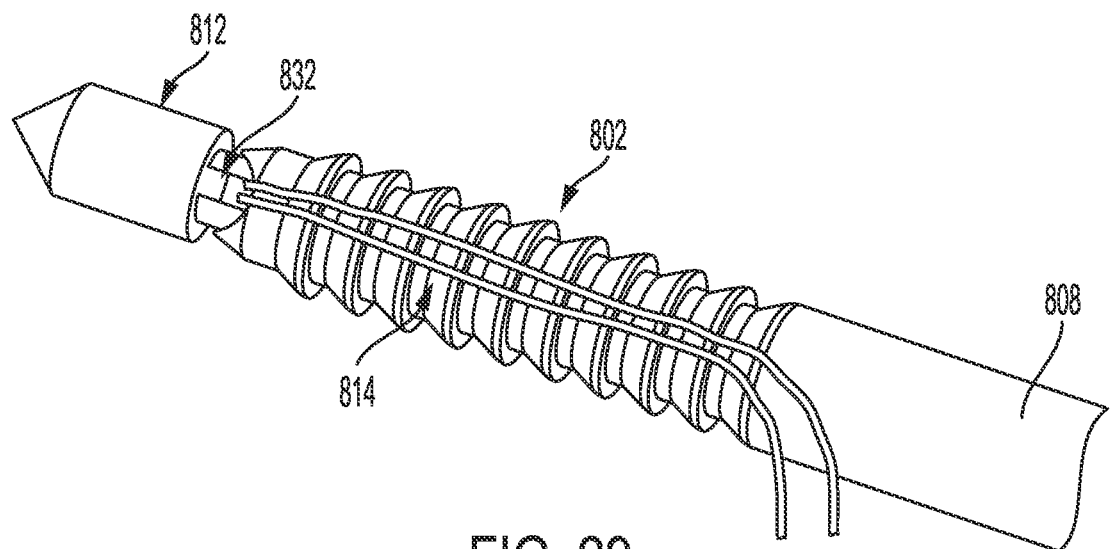
FIG. 29 is a perspective view of distal portion of the inserter tool of FIG. 27 with another embodiment of a suture coupled thereto.

However, in this illustrated embodiment, a notch 804 formed in a distal end of the inner shaft 810 does not fully define a suture retention channel. Instead, the notch 804 cooperates with a distal cap 812 to define an enclosed passage 832 similar to the enclosed passage 532 of the loop 516 discussed above with respect to the inserter tool 500 of FIG. 17. FIG. 28 illustrates the outer shaft 808 and the inner shaft 810 without a remainder of the inserter 800. FIG. 29 illustrates a suture 814 extending through the enclosed passage 832. The distal cap 812 is configured to prevent the suture 814 from moving distally out of the enclosed passage 832 before a desired time of suture 814 decoupling from the inserter tool 800.

The anchor 802 has a distal groove 802g formed therein configured to seat the suture 814 therein prior to advancement of the anchor 802 into bone, as shown in FIG. 29. The distal groove 802g is defined by opposed arcs formed in the anchor's distal end in this illustrated embodiment, but the distal groove 802g can have another shape, e.g., a scalloped shape defined by a plurality of arcs formed in the anchor's distal end, opposed longitudinal slots, opposed rectangular notches, etc.

The distal cap 812 is located distal to the anchor 802 and is releasably coupled to the inner shaft 810. The distal cap 812 is a solid member. The distal cap 812 can be absorbable or non-absorbable. The distal cap 812 in this illustrated embodiment has a cylindrical body with a pointed distally tapering tip, but the distal cap 812 can have another shape, e.g., cylindrical with no pointed distally tapering tip, cylindrical body with a blunt distally tapering tip, square pyramidal, etc.

Figure 30:
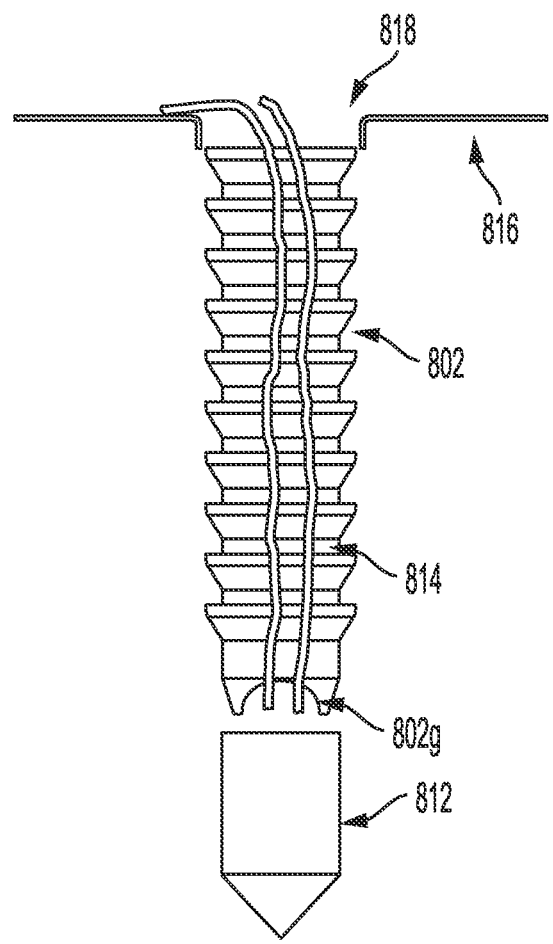
FIG. 30 is a side view of an anchor and a distal cap implanted in bone using the inserter tool of FIG. 27.

The inner shaft 810 is configured to decouple from the distal cap 812 in response to the inner shaft 810 being moved proximally to remove the inner shaft 810, and a remainder of the inserter tool 800, from a patient's body after the outer shaft 808 has been pushed distally, e.g., via strike on the strike cap, to secure the anchor 802 and the suture 814 in bone. The distal cap 812 can thus remain implanted in the patient's body along with the anchor 802 and the suture 814. The decoupling of the inner shaft 810 from the distal cap 802 also eliminates the enclosed passage 832. FIG. 30 illustrates relative positions of the distal cap 812, the anchor 802, and the suture 814 after implantation in a bone hole 818 formed in bone 816. The distal groove 802g of the anchor 802 is also configured to seat the suture 814 therein after advancement of the anchor 802 into the bone hole 818, as shown in FIG. 30. However, depending one or more factors such as a size of the bone hole, a size of the suture, a size of the anchor 802, and the tensioning applied to the suture 814, the suture 814 may not be seated in the groove 802g after implantation but instead be located distal to the groove 802g within the bone hole.

The suture 814 can be positioned in the enclosed passage 832 by a user by hand, or the suture 814 can be positioned in the enclosed passage 832 using a loading aid. For example, the loading aid 522 of FIG. 19 can be used to load the suture 814 in the enclosed passage 832 similar to that discussed above regarding the loading aid 522 being used to thread the suture 514 through the loop 516. For another example, another embodiment of a loading aid 822 illustrated in FIG. 31 can be used to load the suture 814 in the enclosed passage 832.

Figure 31:
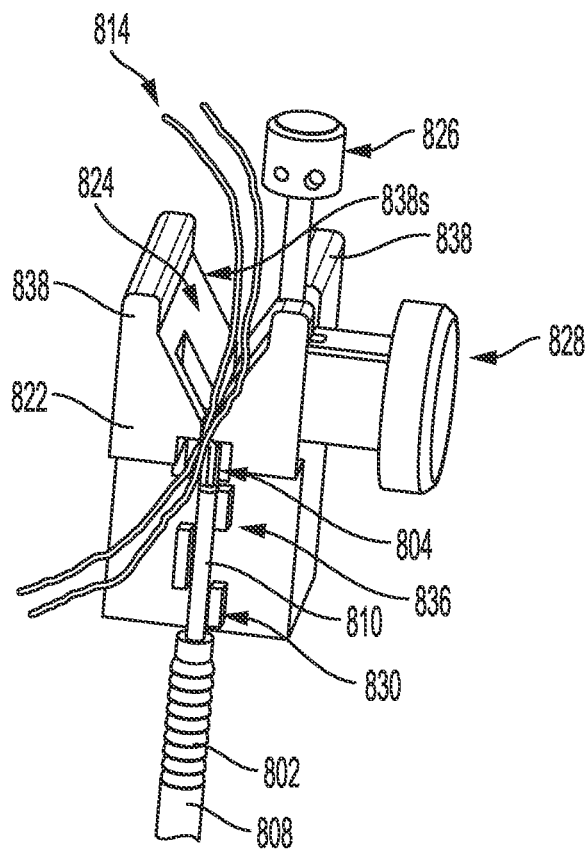
FIG. 31 is a perspective view of a distal portion of the inserter tool of FIG. 27 coupled to another embodiment of a loading aid and another embodiment of a suture seated in a distal seating groove of the loading aid.

FIG. 31 illustrates the loading aid 822 positioned relative to the inserter tool 800 before the suture 814 is positioned in the enclosed passage 832. In an exemplary embodiment, the loading aid 822 is pre-loaded on the inserter tool 800 during manufacturing, which may help ensure that the loading aid 822 is positioned correctly relative to the inner shaft 810 and the distal cap 812 and/or may provide a reminder to a user of the inserter 800 that the suture 814 should be coupled to the inserter 800 before the inserter 800 is advanced into a patient's body. Alternatively, the loading aid 822 can be loaded onto the inserter tool 800 by a user, which may allow for the inserter 800 to be sold without the loading aid 822 and thus at a lower cost than the inserter 800 sold with the loading aid 822.

Figure 32:
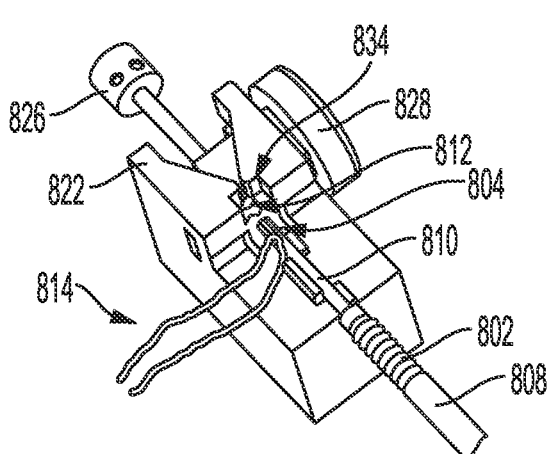
FIG. 32 is a perspective view of the loading aid, the suture, and a distal portion of the inserter tool of FIG. 31 with the suture seated in a notch of the inserter tool.

As shown in FIGS. 31 and 32, the loading aid 822 includes a distal seating groove 824, a plunger 826, a sliding loader 828, a plurality of guide members 830, and a cavity 834 formed therein.

The plurality of guide members 830 are configured as a seating guide for the inner shaft 810 to position the inner shaft 810, and hence the notch 804 thereof, at an optimal position relative to the distal cap 812 for suture loading. The guide members 830 define a seating channel 836 therebetween that is configured to seat the inner shaft 810 therein. The guide members 830 are sized and shaped such that the seating channel 836 has a size and shape that allows the inner shaft 810 to be releasably snapped into and out of the seating channel 836. The guide members 830 are alternately positioned on either side of the seating channel 836 along a length of the seating channel 836. The loading aid 822 includes three guide members 820 in this illustrated embodiment but can include another number of guide members. For example, the loading aid 822 can include two guide members 830 that each extend along an entire length of the seating channel 836 defined therebetween. For another example, the loading aid can include four or more guide members 830 alternately positioned on either side of the seating channel 836 along a length of the seating channel 836. The guide members 830 each include elongate rectangular blocks in this illustrated embodiment but can have another shape, e.g., half-domes, square blocks, etc.

The distal seating groove 824 is defined by opposed distal wings 838 of the loading aid 822. The distal wings 826 each extend radially outward so as to define a V-shape. The distal seating groove 824 is thus V-shaped.

The cavity 834 is located at an apex of the V-shaped distal seating groove 824 and is located distal to the seating channel 836. The notch 804 of the inner shaft 810 is thus positioned proximal to the cavity 834 with the inner shaft 810 and the distal cap 812 coupled to the loading aid 822, as shown in FIG. 32. The enclosed passage 832 does not yet exist in FIGS. 31 and 32.

As shown in FIG. 31, the suture 814 is positioned within the distal seating groove 824 of the loading aid 822. The suture 814 is then, as shown in FIG. 6, positioned on an inner surface 838s of one of the distal wings 838 and slid proximally along the distal wing's inner surface 838s to guide the suture 814 to the apex of the distal seating groove 824, e.g., to the point of the V-shape. The suture 814 can be slid along either of the distal wing's inner surface 838s. The suture 114 continues to be slid proximally to enter the notch 804 of the inner shaft 810. A proximal surface of the notch 804 acts as a stop surface for the suture 814 in the notch 804, although in some embodiments the suture 814 may be positioned in the notch 804 but not abut the stop surface.

With the suture 814 positioned in the notch 804, the sliding loader 828 is actuated to cause the distal cap 812 to move into the cavity 834. The sliding loader 828 is configured to be actuated by sliding the loader 828 radially inward, e.g., by a user pressing on a head of the loader 828, which causes the distal cap 812 previously seated in the loading aid 822 to move radially inward and into the cavity 834. FIG. 32 illustrates the loading aid 822 after the actuation of the sliding loader 828. The distal cap 812 not being seated in the cavity 834 before the suture 814 is positioned in the notch 804 allows the suture 814 to slide into the notch 804 from the distal seating cavity 824.

Figure 33:
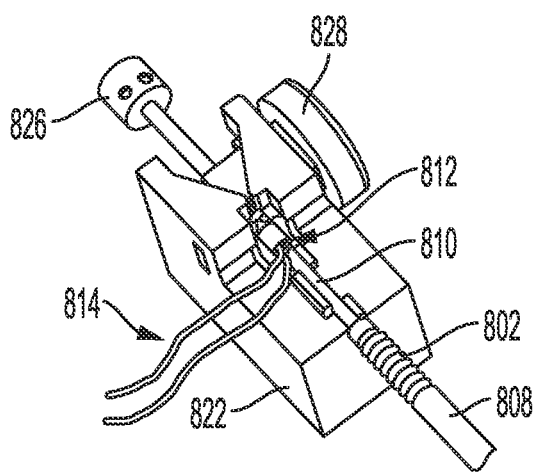
FIG. 33 is a perspective view of the loading aid, the suture, and a distal portion of the inserter tool of FIG. 32 with a distal cap coupled to the inserter tool.

With the distal cap 812 seated in the cavity 834, the plunger 826 is actuated to cause the distal cap 812 to be pushed proximally toward the inner shaft 810 and thereby form the enclosed passage 832 with the suture 814 extending through the enclosed passage 832. The plunger 826 is configured to be actuated by sliding the plunger 826 proximally, e.g., by a user pressing on a head of the plunger 826, which causes the distal cap 812 to move out of the cavity 834 and be seated on a distal end of the inner shaft 810. FIG. 33 illustrates the loading aid 822 after the actuation of the plunger 826. The inserter tool 800 can then be removed from the loading aid 822, with the suture 814 extending through the enclosed passage 834, by releasing the inner shaft 810 from the guide members 830, e.g., by snapping the inner shaft 810 out of the seating channel 836.

As mentioned above with respect to the inserter tool 500 of FIG. 17, the inserter tool 500 can include a suture retention member configured to releasably retain a suture to hold the suture in a desired position at a desired tension. Any of the inserter tools described herein can include a suture retention member. A suture is traditionally retained using a hemostat. The inserter tool including a suture retention member may eliminate the need to use any hemostats for the suture.

Figure 34:
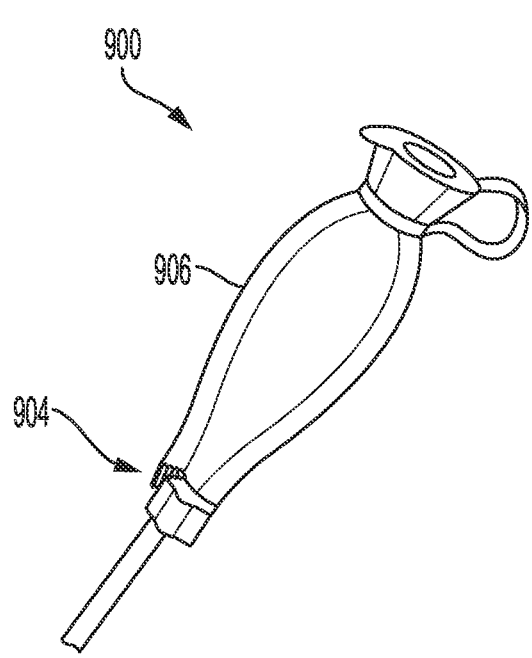
FIG. 34 is a perspective view of a proximal portion of another embodiment of an inserter tool.

FIG. 34 illustrates another embodiment of an inserter tool 900 for knotless anchor insertion in a soft tissue repair surgical procedure. A handle 906 of the inserter tool 900 can be similarly used as the handle for any of the inserter tool handles described herein.

As shown in FIGS. 34-37, the handle 906 includes a suture retention member 904 configured to releasably retain a suture to hold the suture in a desired position at a desired tension. The suture retention member 904 is located at a distal end of the handle 906, which may help avoid interference with a user's holding of the handle 906. The suture retention member 904 can, however, be located elsewhere on the handle 906. The suture retention member 904 in this illustrated embodiment includes a groove 904g formed in the handle 906 configured to seat a suture therein. The groove 904g can have any of a variety of shapes, e.g., U-shaped, V-shaped, a half-dome shape, W-shaped, rectangular-shaped, etc. The suture retention member 904 also includes a rocker switch 904r configured to be selectively moved in and out of alignment with the groove 904g. In some embodiments, the rocker switch 904r can be spring-biased to be in alignment with the groove 904g, which may help retain the suture in a fixed position in the groove 904g.

One or more surfaces of the handle 906 that define the groove 904g can include a gripping feature 904f thereon that is configured to facilitate grip of the suture within the groove 904g. The gripping surface 904f is configured to provide friction with the suture to help retain the suture in a fixed position in the groove 904g when the rocker switch 904r is in alignment with the groove 904g. In an exemplary embodiment, at least a surface 906s of the handle 906 that faces the rocker switch 904r includes the gripping feature 904f, as in this illustrated embodiment, since the rocker switch 904r urges the suture against that surface 906s when in alignment with the groove 904g. The gripping feature 904f includes a ribbed textured surface in this illustrated embodiment but can have other configurations, such as another type of textured surface, surface projections, etc.

Figure 35:
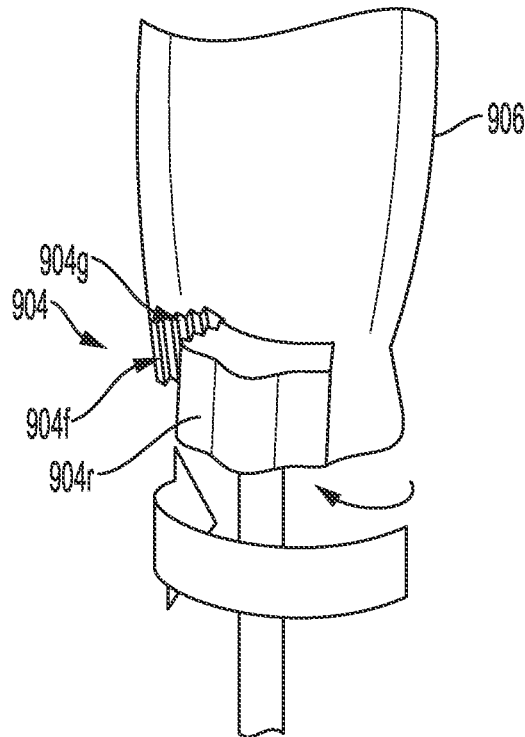
FIG. 35 is a perspective view of an intermediate portion of the inserter tool of FIG. 34.
Figure 36:
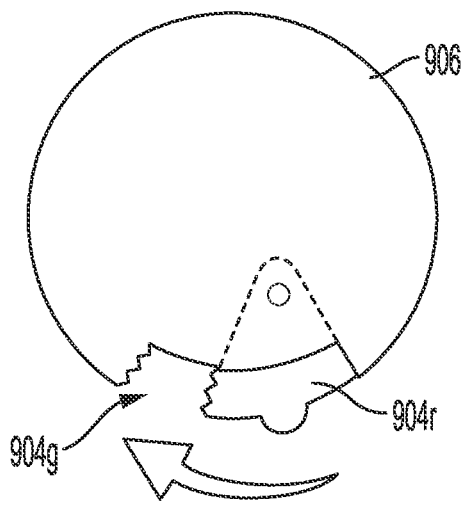
FIG. 36 is a cross-sectional view of the inserter tool of FIG. 34.
Figure 37:
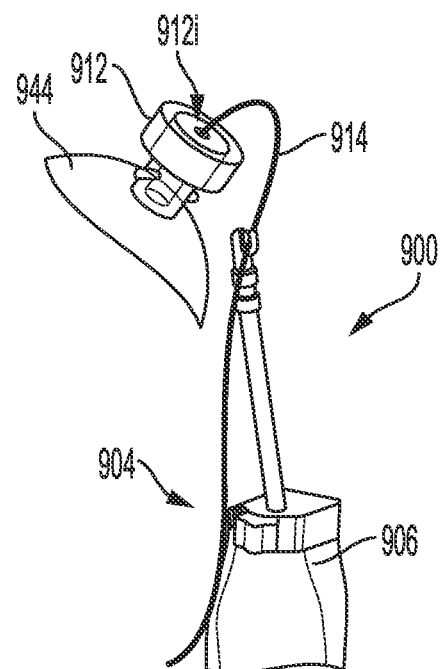
FIG. 37 is a perspective view of a distal portion of the inserter tool of FIG. 34 with a suture coupled thereto and with the suture extending through one embodiment of a cannula positioned in a patient.
Figure 42:
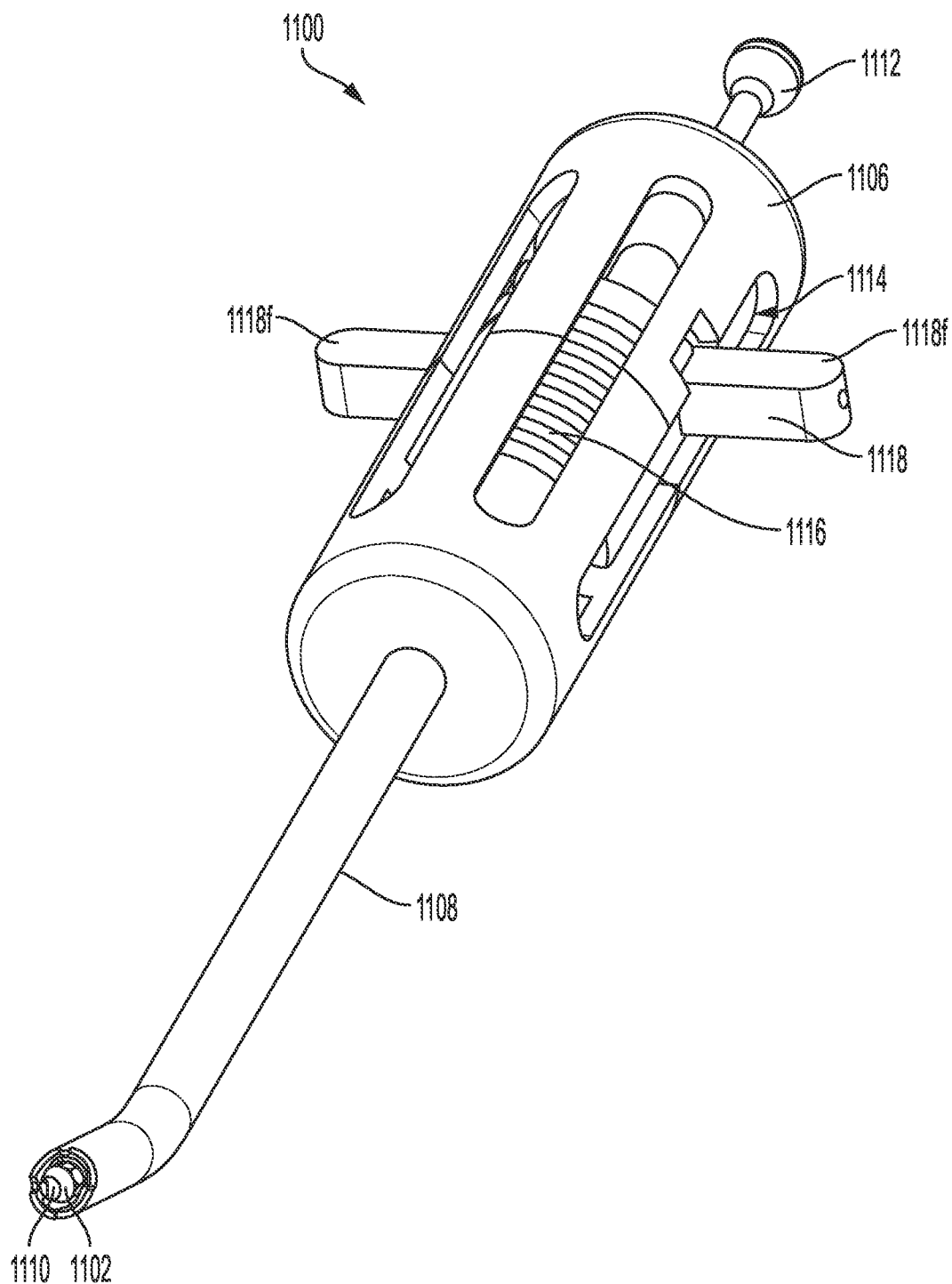
FIG. 42 is a perspective view of a still another embodiment of an inserter tool.

FIGS. 34-36 show the rocker switch 904r out of alignment with the groove 904g. FIG. 37 shows the rocker switch 904r in alignment with the groove 904g and with a suture 914 seated in the groove 904g and retained by the suture retention member 904. FIG. 37 also shows one embodiment of a method of using the inserter tool 900 that includes the suture retention member 904 in a surgical procedure. The surgical procedure is at a shoulder joint in this illustrated embodiment, but as mentioned above, the inserter tool 900 and other embodiments of inserter tools described herein can be used in a variety of other surgical procedures. As shown in FIG. 37, a cannula 912 can be positioned in skin 944 of a patient. The suture 914 can extend through an inner lumen 912i of the cannula 912 into the patient's body, e.g., to a soft tissue therein to be secured in position relative to bone. With the suture 914 extending into the patient's body, a drill or other bone removal tool can be advanced through the inner lumen 912i of the cannula 912 into the patient's body to form a bone hole. The drill or other bone removal tool can then be removed from the cannula 912. The inserter tool 900 can then be "zipped" down the suture 914 and through the inner lumen 912i of the cannula 912 to position a distal end of the inserter tool 900 within the bone hole. The suture 914 can be released from the suture retention feature 904 at any time and repositioned therein any number of times as desired.

The strike surface of each of the strike caps 112, 512, 612 illustrated in FIGS. 1, 17, and 23 is exposed for striking by a mallet, hammer, or other tool. In other embodiments, an inserter tool can include a strike cap and a protective member configured to cover or hide at least the strike surface of the strike cap. The protective member may help prevent premature striking of the strike cap and/or any unintentional distal movement of the strike cap and thus any unintentional distal advancement of an anchor coupled to the inserter tool. In some embodiments the protective member can completely cover or hide the strike cap.

FIGS. 38-41 illustrate another embodiment of an inserter tool 1000 for knotless anchor insertion in a soft tissue repair surgical procedure. The inserter tool 1000 in this illustrated embodiment includes a protective member 1004 configured to cover or hide a strike cap 1012 of the inserter tool 1000. The protective member 1004 can be used with any of the inserter tools described herein.

The protective member 1004 is configured to move between a closed position, which is shown in FIGS. 38 and 39, and an open position, which is shown in FIGS. 40 and 41. FIG. 41 also illustrates one embodiment of a mallet 1016 configured to strike the strike cap 1012. In the closed position, the protective member 1004 covers or hides at least a strike surface 1012s of the strike cap 1012. The entire strike cap 1012s is covered or hidden by the strike cap 1012 with the strike cap 1012 in the closed position in this illustrated embodiment. In the open position, at least the strike surface 1012s of the strike cap 1012 is exposed. The entire strike cap 1012s is exposed with the strike cap 1012 in the open position in this illustrated embodiment.

The protective member 1004 is configured to move from the closed position to the open position, and vice versa, in flip-top fashion. The protective member 1004 is attached to a handle 1006 of the inserter tool 1000 with a living hinge 1014. The protective member 1004 can instead be attached to the handle 1006 of the inserter tool 1000 with another type hinge. The hinge 1014 is configured to keep the protective member 1004 to the handle 1006 regardless of whether the protective member 1004 is in the closed position or the open position. The protective member 1004 can be flipped open and closed with one hand, which may ease usability by allowing a user to open or close the protective member 1004 without changing hand grip of the handle 1006.

FIGS. 42-48 illustrate another embodiment of an inserter tool 1100 for knotless anchor insertion in a soft tissue repair surgical procedure. The inserter tool 1100 is generally configured and used similar to the inserter tool 100 of FIG. 1, e.g., is configured to insert an anchor 1102 into a bone of a patient to secure a soft tissue relative to the bone and includes a handle 1106, an outer shaft 1108 that extends distally from the handle 1106, an inner shaft 1110 that extends distally from the handle 1106, and a strike cap 1112 that extends proximally from the handle 1106. The anchor 1102 is generally configured and used similar to the anchor 102 of FIG. 1.

However, unlike the inserter tools discussed above, the outer and inner shafts 1108, 1110 in this illustrated embodiment are not linear. Instead, the outer and inner shafts 1008, 1110 curve in a distal portion thereof, as shown in FIGS. 42, 44, 45, and 47. Although the outer and inner shafts 1108, 1110 are curved in this illustrated embodiment, the outer and inner shafts 1108, 1110 can instead be linear. Similarly, the above-discussed inserter tools can have curved inner and outer shafts instead of linear inner and outer shafts. The outer and inner shafts 1008, 1110 being curved in distal portion thereof may facilitate approach of the inserter tool's distal end to a target site for implantation of the anchor 1102 since the tight constraints of patient anatomy at joints can make it difficult to approach a target site. The curvature of the outer and inner shafts 1008, 1110 is fixed in this illustrated embodiment.

Additionally, in this illustrated embodiment, an opening 1104 is formed in a distal end of the inner shaft 1110, as shown in FIGS. 44, 45, 47, and 48, is configured to seat a suture therein. The opening 1104 defines an enclosed passage in which the suture is configured to extend, similar to the enclosed passages discussed above. The opening 1104 has an ovular cross-sectional shape in this illustrated embodiment but can have another cross-sectional shape, e.g., circular, rectangular, etc. The distal end of the inner shaft 1110 in this illustrated embodiment is closed distal end. The closed distal end is rounded in this illustrated embodiment.

Figure 44:
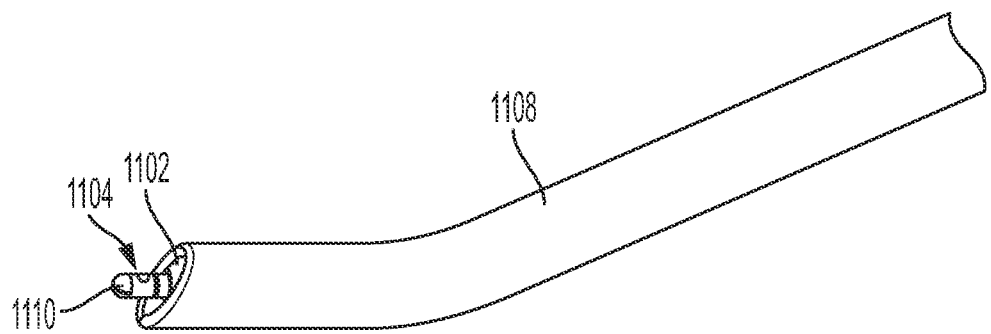
FIG. 44 is a perspective view of a distal portion of the inserter tool of FIG. 42.

FIG. 44 illustrates the inner shaft 1110 in a loading position in which the opening 1104 is located distal of the anchor 1102 and distal to an open distal end of the outer shaft 1108. The opening 1104 is therefore accessible for suture loading therethrough. In some embodiments, the suture is positioned in the opening 1104 during manufacturing. A user of the inserter tool 1100 thus receives the inserter tool 1100 with the suture pre-loaded in the inserter tool 1100. In other embodiments, the suture is positioned in the opening 1104 by a user of the inserter tool 1100, which may provide a user of the inserter 1100 flexibility in deciding on a size and type of suture to use that is appropriate for a particular patient and a particular surgical procedure. The suture can be positioned in the opening 1104 by the user by hand, similar to the threading of a needle. Alternatively to hand positioning, the suture can be positioned in the opening 1104 using a loading aid, e.g., the loading aid 522 of FIG. 19.

Figure 43:
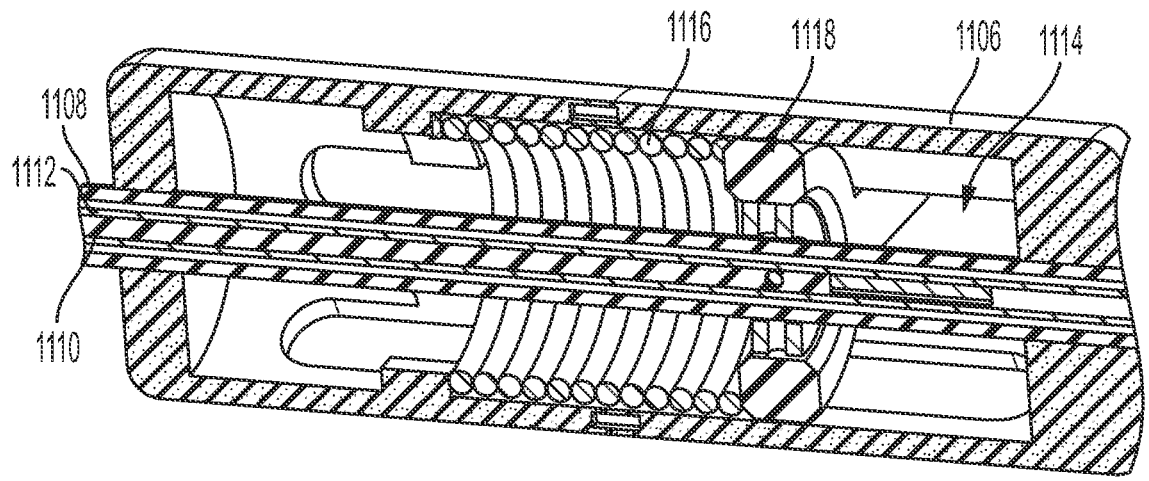
FIG. 43 is a cross-sectional view of a portion of the inserter tool of FIG. 42.
Figure 45:
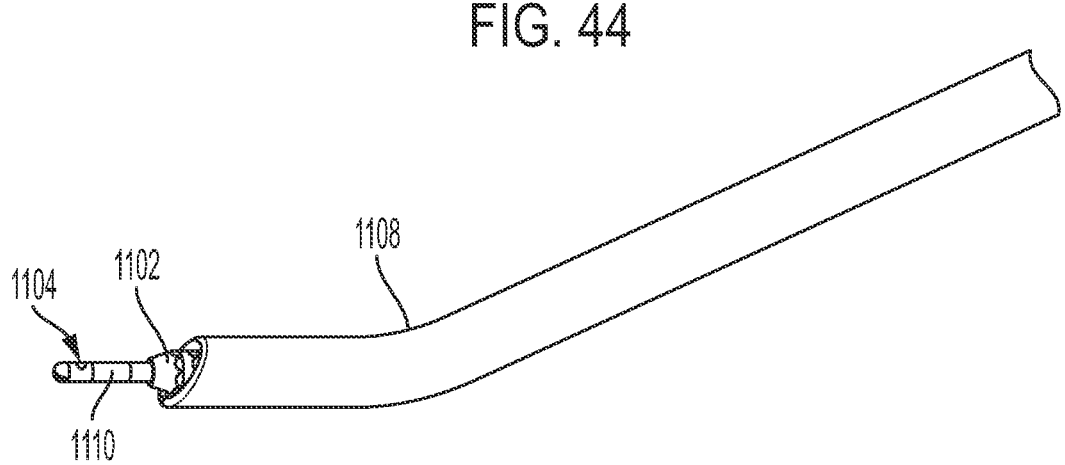
FIG. 45 is a perspective view of a distal portion of the inserter tool of FIG. 44 with an inner shaft of the inserter tool advanced farther distally relative to an outer shaft of the inserter tool.
Figure 46:
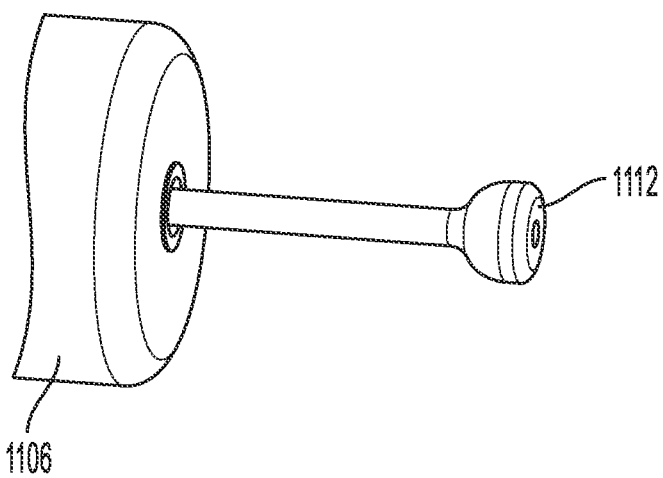
FIG. 46 is a perspective view of a proximal portion of the inserter tool of FIG. 42.

With the suture extending through the opening 1104, the distal end of the inner shaft 1110 is advanced distally into a bone hole. The inserter 1100 includes a collar 1118 that is operatively coupled to the inner shaft 1110, as shown in FIG. 43. Sliding the collar 1118 relative to the handle 1106 causes the inner shaft 1110 to move distally relative to the anchor 1102 and the outer shaft 1108 so as to extend a distance distally beyond the outer shaft 1108 and the anchor 1102, as shown in FIG. 45. The opening 1104 is this located a distance distally beyond the outer shaft 1108 and the anchor 1102 and is positioned in the bone hole. The distance that the inner shaft 1110 is advanced distally beyond the outer shaft 1108 and the anchor 1102 will vary based on a depth of the bone hole into which the inner shaft 1110 is being advanced.

The collar 1118 includes opposed finger holds 1118*f* that extend radially through slots 1114 formed in the handle 1106. The finger holds 1118*f* are configured to provide a surface easily held by hand during movement of the collar 1118. By including finger holds 1118*f* on opposed sides of the collar 1118, the collar 1118 may be conveniently held by a left hand or a right hand and be in an easily held position regardless of the loading aid's rotational position relative to the user. One of both of the finger holds 1118*f* may be held at a time. The finger holds 1118*f* move distally in the slots 1114 as the collar 1118 moves distally relative to the handle 1106.

The inserter tool 1100 includes a spring 1116 disposed in the handle 1106 and operatively coupled to the collar 1118. The spring 1116 is a coil spring in this illustrated embodiment but can be another type of spring or bias member. The spring 1116 biases the collar 1118 proximally. The inner shaft 1110 is thus biased proximally. The distal advancement of the collar 1118 relative to the handle 1106 causes the spring 1116 to compress. The collar 1118 can be locked in position relative to the collar 1118 in a distally advanced position so as to lock the inner shaft 1110 in a distally advanced position relative to the outer shaft 1108 and the anchor 1102. The inner shaft 1110 is coupled to the collar 1118, so when the collar 1118 is locked in the distal position the collar 1118 also locks the inner shaft 1110 distally.

Figure 47:
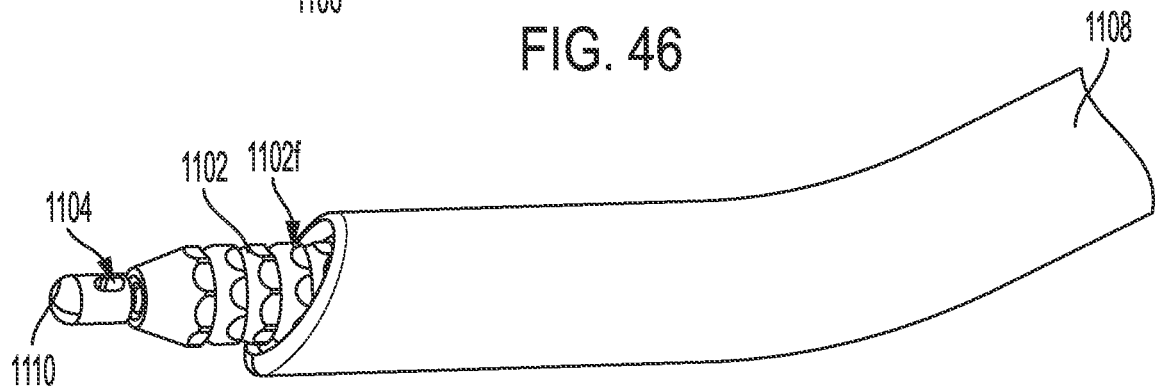
FIG. 47 is another perspective view of a distal portion of the inserter tool of FIG. 45 with an anchor advanced distally relative to the inner and outer shafts.
Figure 48:
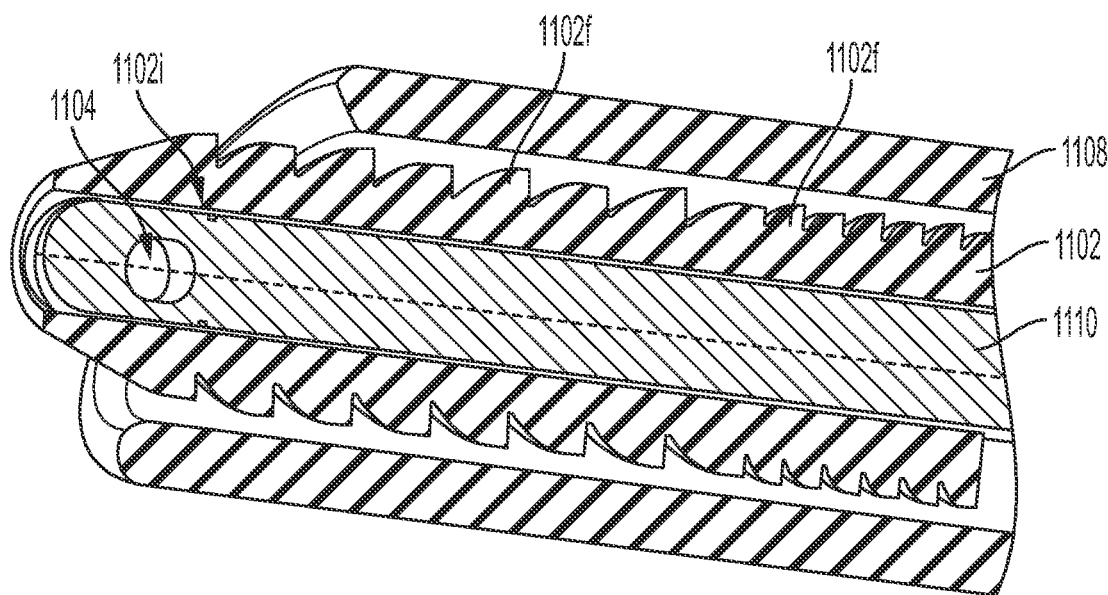
FIG. 48 is a cross-sectional view of the anchor and the inner and outer shafts of the inserter tool of FIG. 42.

With the inner shaft 1110 and the opening 1104 with the suture extending therethrough positioned in the bone hole, the anchor 1102 is advanced distally by striking the strike cap 1112 with a mallet, hammer, or other tool. Striking the strike cap 1112 does not cause the outer shaft 1108 to move distally to push the anchor 1102 distally in this illustrated embodiment. Instead, a distal extension of the strike cap 1112 extends distally through the outer shaft 1108, as shown in FIG. 43, such that a distal surface of the strike cap 1112 abuts a proximal surface of the anchor 1102. The striking of the strike cap 1112 thus causes the strike cap 1112 to move distally and push the anchor 1102 distally relative to the outer and inner shafts 1108, 1110. FIGS. 45, 47, and 48 show the anchor 1102 partially distally advanced out of the outer shaft 1108.

As discussed above, the advancement of the anchor 1102 into the bone hole causes bone-engaging surface features 1102*f* of the anchor 1102 to engage a wall of the bone hole to secure the anchor 1102 therein and secure the suture relative to the bone. The bone-engaging surface features 1102*f* in this illustrated embodiment include a plurality of ribs each extending circumferentially around the anchor 1102 at different axial positions along the anchor's longitudinal length. Each of the ribs has a scalloped proximal edge, which may further facilitate the anchor's engagement with bone. As shown in FIG. 48, the ribs are narrower in a proximal portion of the anchor 1102 than in a distal portion of the anchor 1102. The narrower ribs may facilitate anchor engagement with cortical bone, and the wider ribs may facilitate anchor engagement with cancellous bone that underlies the cortical bone.

With the anchor 1102 positioned in the bone hole, and trapping the suture therein as discussed above, the inserter tool 1100 can be removed from the patient's body. The collar 1118 can be moved proximally relative to the handle 1106 to cause the inner shaft 1110 to move proximally so as to retract relative to the anchor 1102, the outer shaft 1108, and the handle 1106. The inner shaft 1110 can thereby be removed from the cannulated anchor's inner lumen 1102*i*. The inserter tool 1110 can then be removed from the patient's body by moving the outer and inner shafts 1108, 1110 proximally by pulling the inserter 1100 proximally by the handle 1106. Tails of the suture can be trimmed as desired.

FIGS. 49-54 illustrate another embodiment of an inserter tool 1200 for knotless anchor insertion in a soft tissue repair surgical procedure. The inserter tool 1200 is generally configured and used similar to the inserter tool 100 of FIG. 1, e.g., is configured to insert an anchor 1202 into a bone of a patient to secure a soft tissue relative to the bone and includes a handle 1206, an outer shaft 1208 that extends distally from the handle 1206, an inner shaft 1210 that extends distally from the handle 1206 and includes a notch formed therein that defines a suture retention channel 1204, and a strike cap 1212 that extends proximally from the handle 1206.

Figure 51:
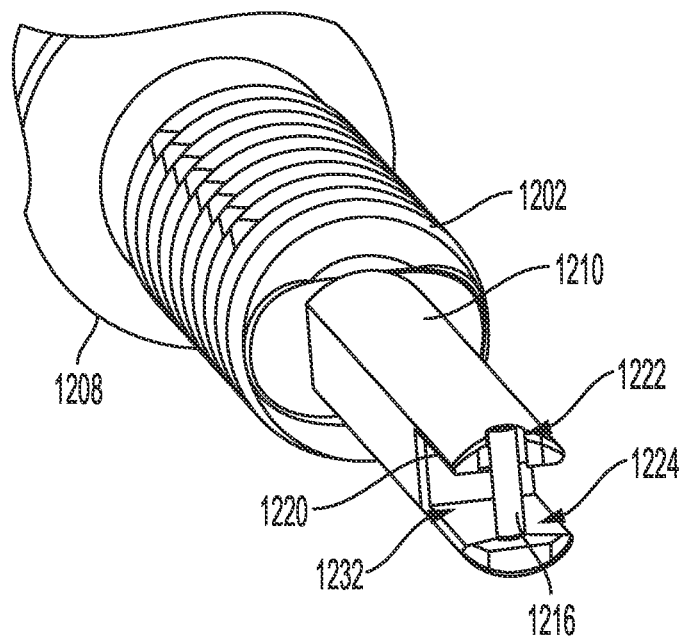
FIG. 51 is another perspective view of a distal portion of the inserter tool of FIG. 49.
Figure 51A:
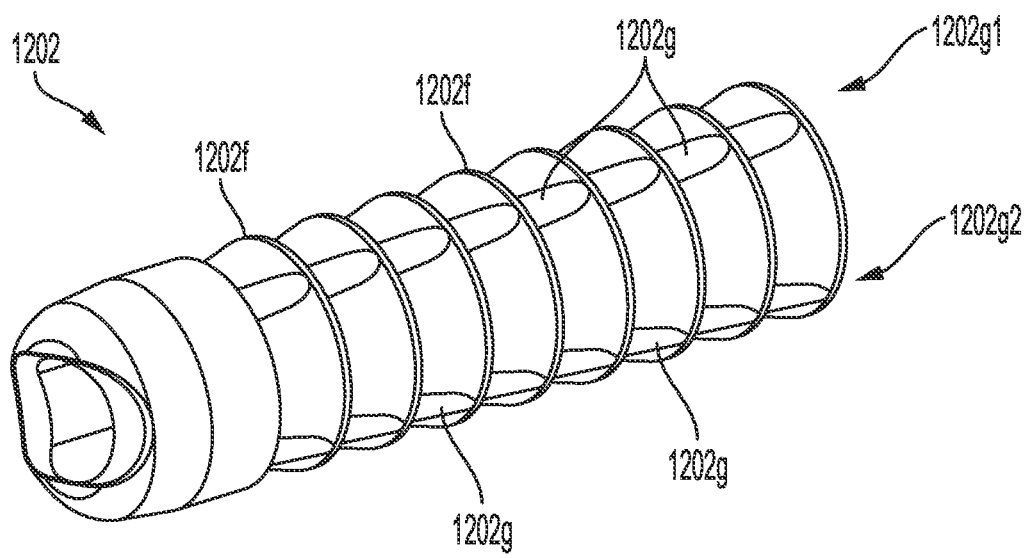
FIG. 51A is a perspective view of an embodiment of an anchor.

The anchor 1202 is generally configured and used similar to the anchor 102 of FIG. 1. FIG. 51A illustrates the anchor as a standalone element. A plurality of bone-engaging surface features 1202f are formed on an exterior surface of the anchor 1202. The bone-engaging surface features 1202f in this illustrated embodiment include a plurality of ribs each extending circumferentially around the anchor 1202 at different axial positions along the anchor's longitudinal length. The anchor 1202 in this illustrated embodiment includes a plurality of gussets 1202g that are configured to reinforce the anchor 1202. The gussets 1202g each extend longitudinally along the anchor 1202. A first set of the gussets 1202g1 are aligned with one another along the anchor's length, a second set of the gussets 1202g2 are aligned with one another along the anchor's length, a third set of the gussets 1202g are aligned with one another along the anchor's length, and a fourth set of the gussets 1202g are aligned with one another along the anchor's length. The third and fourth sets of gussets 1202g are obscured in FIG. 51A. The first, second, third, and fourth sets of gussets 1202g are arranged equidistantly around the circumference of the anchor 1202, which may help reinforce the anchor 1202 around the entire circumference thereof. In other embodiments, and anchor can include a different number of sets of gussets and/or the sets of gussets can be non-equidistantly arranged around the anchor's circumference.

The notch and the suture retention channel 1204 in this illustrated embodiment are generally configured and used similar to the notch and the suture retention channel 116 of FIG. 1, e.g., the notch is formed in a distal end of the inner shaft 1210 and is defined by opposed distal arms 1220 of the inner shaft 1210, the suture retention channel 1204 has an open distal end and a closed proximal end, and the suture retention channel 1204 extends longitudinally. The suture retention channel 1204 has a substantially constant diameter in this illustrated embodiment but can have different diameters in different portions, e.g., a proximal portion of the suture retention channel 1204 having a greater diameter than a distal portion of the suture retention channel, a distal portion of the suture retention channel 1204 having a greater diameter than a proximal portion of the suture retention channel, or other different diameters. A person skilled in the art will appreciate that values, such as diameter values, may not be precisely the same but nevertheless considered to be substantially the same for any of one or more reasons, such as manufacturing tolerances or sensitivity of measurement equipment.

The handle 1206 in this illustrated embodiment includes facets 1206f on opposed sides, e.g., left and right sides, thereof. The facets 1206f are configured to help a user with grip and fine motor movements.

In this illustrated embodiment, the inserter tool 1200 includes a pliable member 1216. As mentioned above, a "pliable member" is also referred to herein as a "flexible member." The pliable member 1216 is configured to fold or bend without breaking, cracking, or otherwise losing structural integrity. The pliable member 1216 is a metal single filament wire in this illustrated embodiment but can have other configurations, e.g., a metal multi-filament wire, a braided fabric, a textile strand, a monofilament fiber, etc.

The pliable member 1216 is located distal to the anchor 1202 that has the inner shaft 1210 positioned in an inner lumen thereof. The pliable member 1216 has a first end 1216a fixedly attached to the inner shaft 1210 and has a second end 1216b that is free so as to not be fixedly attached to the inner shaft 1210.

Figure 52:
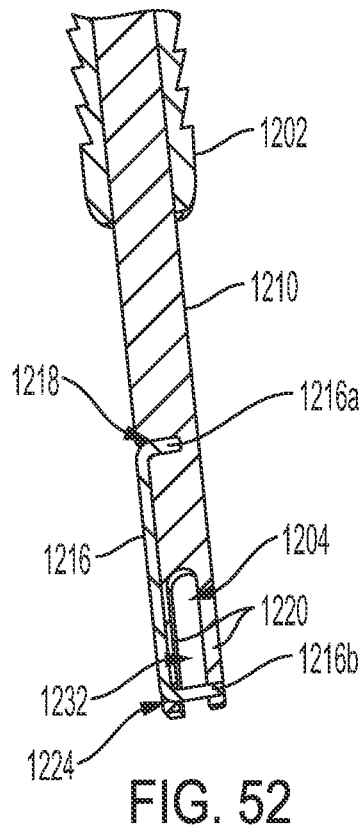
FIG. 52 is a cross-sectional view of a distal portion of the inserter tool of FIG. 49.
Figure 53:
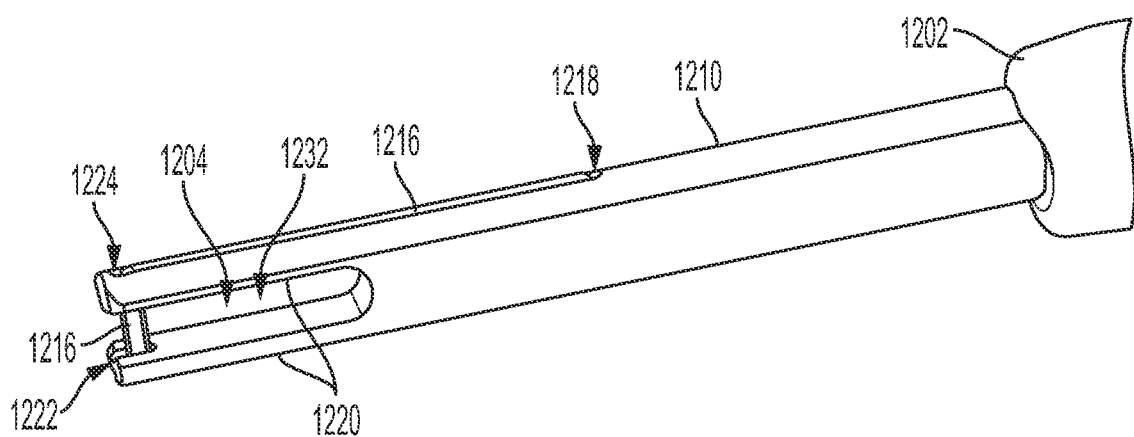
FIG. 53 is yet another perspective view of a distal portion of the inserter tool of FIG. 49.

The first end 1216a of the pliable member 1216 can be fixedly attached to the inner shaft 1210 in any of one or more ways, such as by being crimped to the inner shaft 1210, adhered to the inner shaft 1210 using adhesive, welded to the inner shaft 1210, or attached using another attachment mechanism. In this illustrated embodiment, the inner shaft 1210 includes a cavity 1218 formed therein that is configured to fixedly seat the first end 1216a of the pliable member 1216 therein. The first end 1216a of the pliable member 1216 is fixedly attached to the inner shaft 1210 in the cavity 1218. The cavity 1218 is formed in a sidewall of the inner shaft 1210 and extends substantially perpendicular to a longitudinal axis of the inner shaft 1210, and thus substantially perpendicular to a longitudinal axis of the outer shaft 1208 that is coaxial with the longitudinal axis of the inner shaft 1210. A person skilled in the art will appreciate that axes may not be precisely perpendicular but nevertheless considered to be substantially perpendicular for any of one or more reasons, such as manufacturing tolerances or sensitivity of measurement equipment. The cavity 1218 extending substantially perpendicular to the longitudinal axis of the inner shaft 1210 may help prevent the first end 1216a of the pliable member 1216 from being detached from the inner shaft 1210 during movement of the pliable member 1216, as discussed further below. The cavity 1218 is formed in the inner shaft 1210 proximal to the arms 1220 and distal to the anchor 1202, as shown in FIGS. 52 and 53.

The inner shaft 1210 includes a groove 1222 configured to releasably seat the second end 1216b of the pliable member 1216 therein. The groove 1222 is formed in a first one of the inner shaft's distal arms 1220 and extends into the distal arm 1220 and through a distal tip of the distal arm 1220. The groove 1222 is formed on an opposite side, e.g., right side opposed to the left side, of the inner shaft 1210 than the cavity 1218. Release of the second end 1216b of the pliable member 1216 from the groove 1222, e.g., movement of the second end 1216b distally out of the groove 1222, will thus urge the pliable member 1216 toward the side of the inner shaft 1210 in which the cavity 1218 is formed.

The inner shaft 1210 also includes a hole 1224 formed therein configured to seat the pliable member 1216 therein. The hole 1224 is located between the cavity 1218 and the groove 1222 such that an intermediate portion of the pliable member 1216 that is located between the first and second ends 1216a, 1216b of the pliable member 1216 extends through the hole 1224. The hole 1224 is formed in the one of the inner shaft's distal arms 1220 that does not have the groove 1222 formed therein and is formed on a same side of the inner shaft 1210 as the cavity 1218. The hole 1224 is configured to help constrain bending movement of the pliable member 1216 to a distal portion of the pliable member 1216 that extends from the hole 1224 to the groove 1222, which may help prevent the pliable member 1216 from tangling with or otherwise interfering with any matter during surgical use.

The pliable member 1216 defines an enclosed passage 1232 in cooperation with the distal end of the inner shaft 1210. The inner shaft 1210 defines three sides of the enclosed passage 1232, with a distal surface of the inner shaft 1210 defining a proximal side of the enclosed passage 1232 and the distal arms 1220 defining opposed sides (e.g., left and right sides) of the enclosed passage 1232. The pliable member 1216 defines a fourth and final side of the enclosed passage 1232. In particular, the distal portion of the pliable member 1215 that extends between the hole 1224 and the groove 1222 defines the fourth and final side of the enclosed passage 1232, A suture is configured to extend through the suture retention channel 1216 and the enclosed passage 1232 during use of the inserter tool 1200, similar to that discussed above regarding the suture retention channel 116 and as discussed further below. The pliable member 1216 is configured to move to open the enclosed passage 1232 and thereby allow release of the suture from the suture retention channel 1216, as also discussed further below. In general, the pliable member 1216 is configured to move out of the groove 1222 and bend to open the enclosed passage 1232 by no longer providing the fourth side of the enclosed passage 1232.

In an exemplary embodiment, the pliable member 1216 is made from a superelastic material, such as Nitinol or other material. The pliable member 1216 can have a default bent shape that corresponds to a shape of the pliable member 1216 with the pliable member 1216 seated in the groove 1222 and cooperating with the inner shaft 1210 to form the enclosed passage 1232, which may help ensure that the second end 1216b of the pliable member 1216 remains seated in the groove 1222 until desired.

The handle 1206 in this illustrated embodiment includes a suture retention member 1234 configured to releasably retain a suture to hold the suture in a desired position at a desired tension. The suture retention member 1234 is located at a distal end of the handle 1206 but as mentioned above can be located elsewhere. The suture retention member 1234 in this illustrated embodiment includes a pair of grooves on opposed sides, e.g., left and right sides, of the handle 1206. Providing the suture retention member 1234 on opposed sides of the handle 1206 may help accommodate use of the inserter tool 1200 by left-handed and right-handed users and/or may facilitate engaging the suture with one of the suture retention members 1234 regardless of an orientation at which the inserter tool 1200 is being held and an angle of the suture's approach to the handle 1206.

A first one of the suture retention grooves is defined between the handle 1206 and a first elastomeric cleat 1236a fixedly attached to the handle 1206. A second one of the suture retention grooves is defined between the handle 1206 and a second elastomeric cleat 1236b fixedly attached to the handle 1206. The first and second elastomeric cleats 1236a, 1236b are each made from an elastomeric material, such as rubber or other polymer. The handle 1206 is made from a rigid, non-elastomeric material, such as a plastic such as polycarbonate or other plastic; metal (e.g., stainless steel, titanium, etc.); polytetrafluoroethylene (PTFE); or other biocompatible material. The grooves are thus each located at a junction between an elastomeric material and a rigid material. The elastomeric material of the first and second elastomeric cleats 1236a, 1236b allows a width of the groove associated therewith to dynamically increase to adjust to a size and shape of the suture being seated therein to securely hold the suture in the groove, gripped between the elastomeric material and the rigid material. The suture retention member 1234 is thus self-adjusting. Different sutures have different sizes and shapes, and the first and second elastomeric cleats 1236a, 1236b are each configured to dynamically adjust to the particular size and shape of a suture being seated therein. The suture being securely held in the groove may help the suture's tension be maintained, e.g., without being lessened, while the suture is retained by the suture retention member 1234. When the suture is released from the groove, the elastomeric cleat 1236a, 1236b is no longer gripping the suture and is thus allowed to return to its original, smaller width as the elastomeric material elastically returns to its original configuration.

The suture retention member 1234 is located at a hammerhead shaped portion of the inserter tool 1200 defined by the handle 1206 and the elastomeric cleats 1236a, 1236b. A proximal surface of the hammerhead shaped portion defined by a proximal surface of the handle 1206 and a proximal of each of the elastomeric cleats 1236a, 1236b, extends radially outward and tapers distally. The tapering is configured to urge a suture along the proximal surface of the handle 1206 toward one of the elastomeric cleats 1236a, 1236b for seating the groove associated therewith. Each of the elastomeric cleats 1236a, 1236b has a beveled edge facing its associated groove, which may also help urge the suture into the groove.

Figure 49:
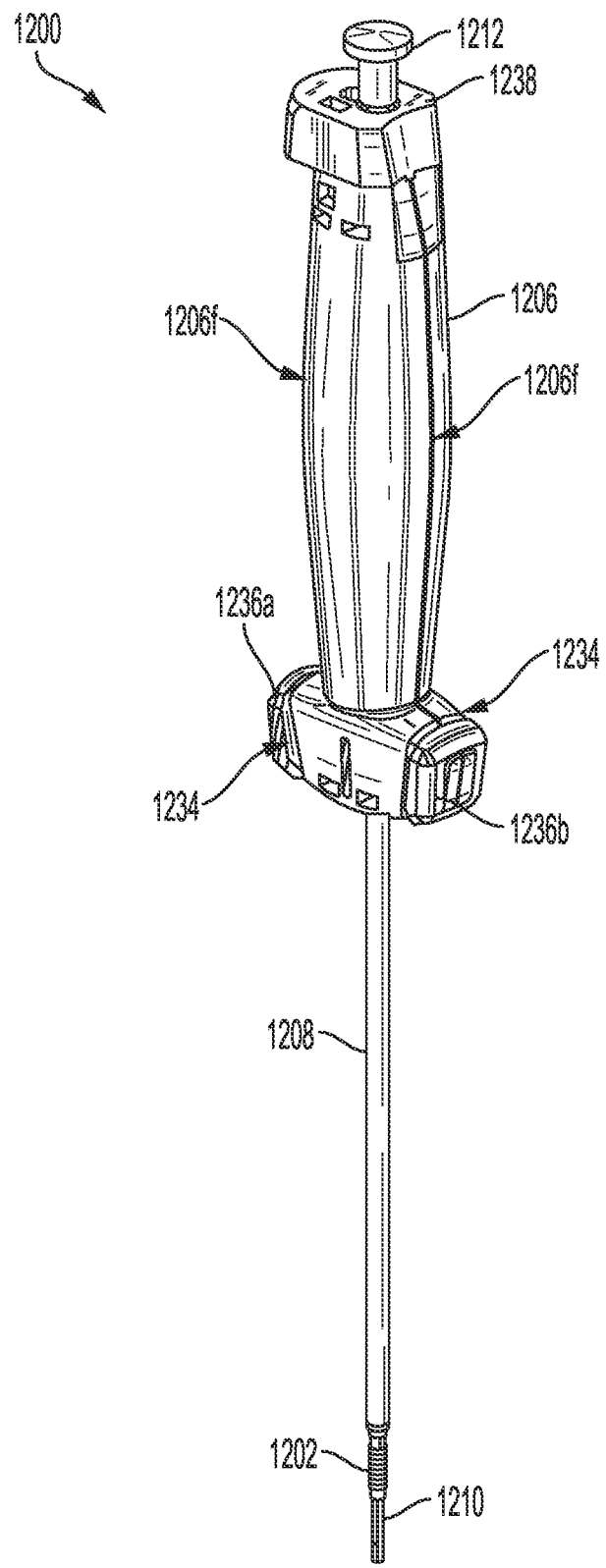
FIG. 49 is a perspective view of a still another embodiment of an inserter tool.
Figure 50:
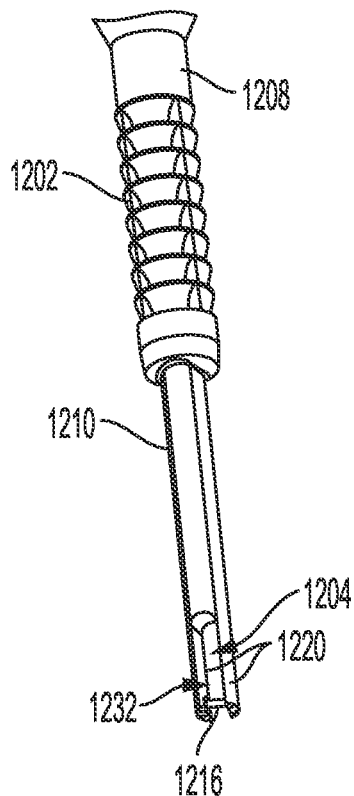
FIG. 50 is a perspective view of a distal portion of the inserter tool of FIG. 49.
Figure 57:
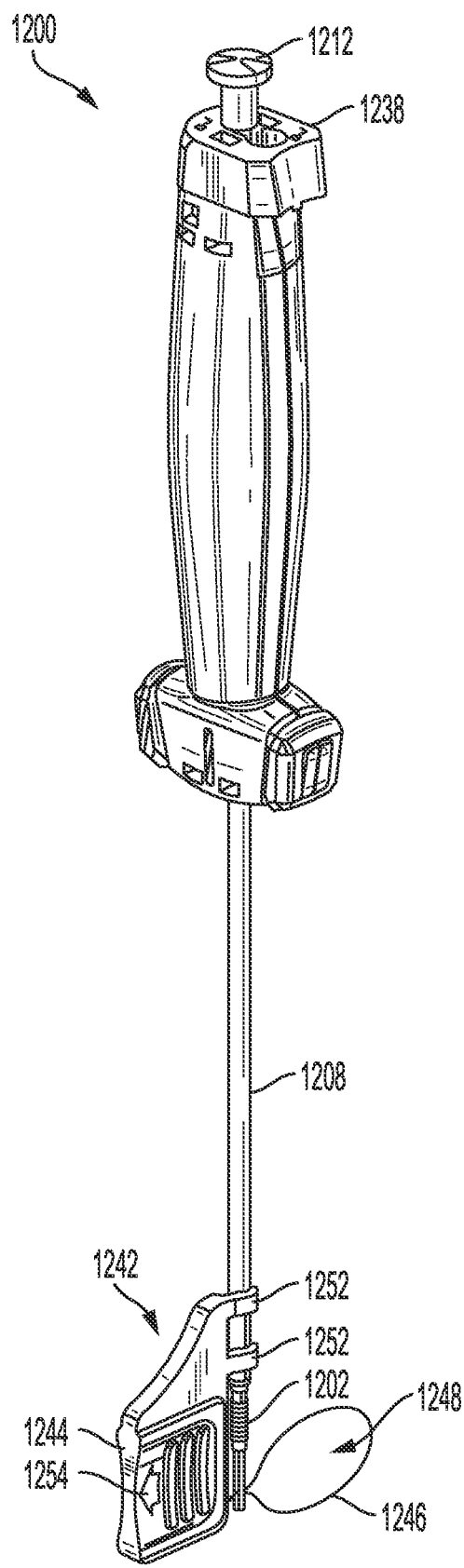
FIG. 57 is another perspective view of the inserter tool of FIG. 49 with the locking mechanism of the inserter tool in a locked position and with another embodiment of a loading aid coupled to the inserter tool.
Figure 58:
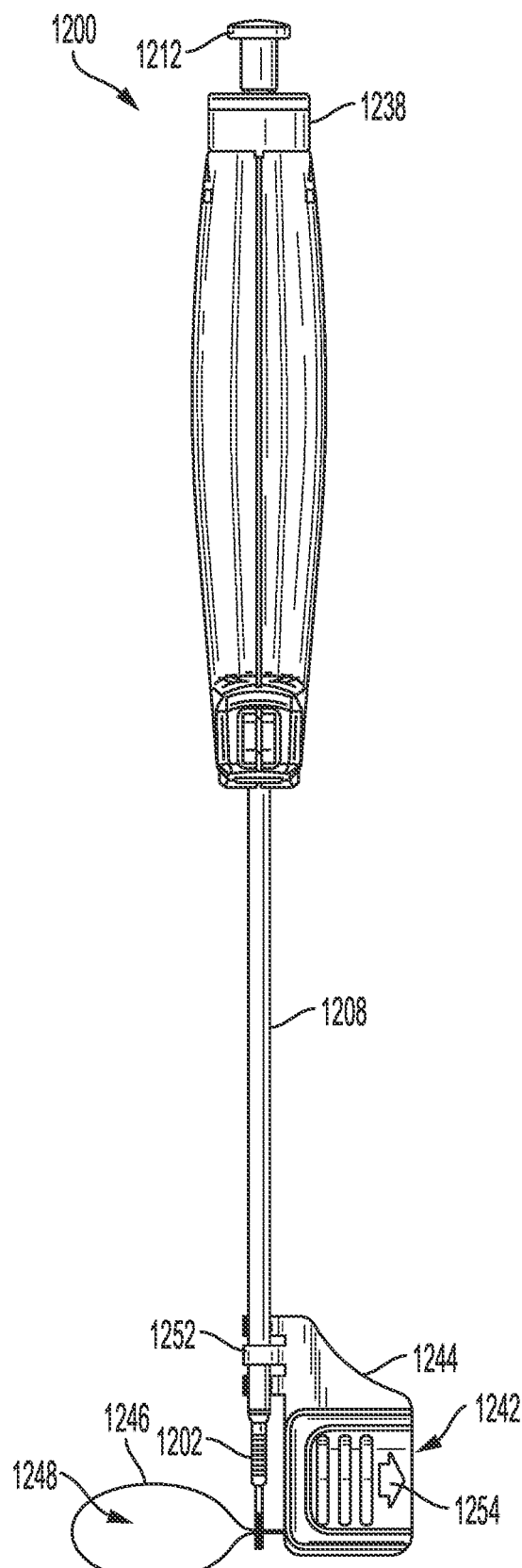
FIG. 58 is another perspective view of the inserter tool and the loading aid of FIG. 57.

As in this illustrated embodiment, a locking mechanism 1238 can be configured to lock the outer shaft 1208 in position relative to the inner shaft 1210 when the locking mechanism 1238 is in a locked position. FIGS. 55, 57, and 58 show the locking mechanism 1238 in the locked position. FIGS. 49 and 54 show the locking mechanism 1238 in an unlocked position, in which the outer shaft 1208 is not locked in position relative to the inner shaft 1210. The locking mechanism 1238 is configured to move from the locked position to the unlocked position by sliding relative to the outer shaft 1208, the inner shaft 1210, the strike cap 1212, and the handle 1206. The sliding movement of the locking mechanism 1238 is lateral movement substantially perpendicular to the longitudinal axes of the outer and inner shafts 1208, 1210. The initial position of the locking mechanism 1238 is the locked position, to help prevent premature distal translation of the outer shaft 1208 relative to the inner shaft 1210.

The locking mechanism 1238 includes a depression 1238d on a side thereof. The depression 1238d is configured to communicate where a finger should be placed on the locking mechanism 1238. The depression's surface is configured as a push surface on which a finger can be placed to push the locking mechanism 1238 from the locked position to the unlocked position. A curvature of the depression 1238 matches a curvature of the handle 1206 adjacent to the locking mechanism 1238 in the unlocked position. The matching curvature of the depression 1238 and the handle 1206 is configured to indicate to a user that the locking mechanism 1238 has fully moved to the unlocked position.

The locking mechanism 1238 includes a keyhole 1240 formed therein in which the outer shaft 1208 and the strike cap 1212 are each configured to move. The keyhole 1240 includes a reduced diameter portion 1240a and an enlarged diameter portion 1240b. With the locking mechanism 1238 in the locked position, the outer shaft 1208 extends through the reduced diameter portion 1240a and the strike cap 1212 is located proximal to the keyhole 1240. The diameter of the reduced diameter portion 1240a is less than a diameter of the strike cap 1212 at least at the distal end of the end cap 1212.

The strike cap 1212 thus cannot move distally into the keyhole 1240, thereby preventing the outer shaft 1208 from moving distally by the strike cap 1212 being struck on its proximal surface 1212s. The proximal surface 1212s in this illustrated embodiment is convex curved, which may provide more feedback (compared to a flat surface) to a user striking the strike cap 1212. With the locking mechanism 1238 in the unlocked position, the outer shaft 1208 extends through the enlarged diameter portion 1240b and the strike cap 1212 is located proximal to the keyhole 1240. The diameter of the enlarged diameter portion 1240b is greater than the diameter of the strike cap 1212 at least at the distal end of the strike cap 1212. The strike cap 1212 thus can move distally into the keyhole 1240, thereby allowing the outer shaft 1208 to move distally by the strike cap 1212 being struck on its proximal surface 1212s. The diameter of the enlarged diameter portion 1240b is less than a diameter of a head of the strike cap 1212 that includes the proximal surface 1212s, thereby preventing the strike cap 1212 from fully passing into the keyhole 1240 because a distal surface of the strike cap 1212 will abut the locking mechanism 1328 around the keyhole 1240. FIG. 56 shows the locking mechanism 1238 in the unlocked position after the strike cap 1212 has been struck with the distal surface of the strike cap 1212 abutting the locking mechanism 1238 around the keyhole 1240.

The locking mechanism 1238 in this illustrated embodiment is not releasable from the inserter tool 1200.

The suture is positioned in the enclosed passage 1232 by a user of the inserter tool 1200, which may provide a user of the inserter tool 1200 flexibility in deciding on a size and type of suture to use that is appropriate for a particular patient and a particular surgical procedure. The suture can be positioned in the enclosed passage 1232 by the user by hand, similar to the threading of a needle. Alternatively to hand positioning, the suture can be positioned in the enclosed passage 1232 using a loading aid such as the loading aid 1242 illustrated in FIGS. 57 and 58.

The loading aid 1242 in this illustrated embodiment includes a suture threader. A suture threader can have a variety of configurations, as will be appreciated by a person skilled in the art. In this illustrated embodiment, the loading aid 1242 is generally configured and used similar to the loading aid 522, e.g., includes a base 1244 and a wire loop 1246 that is attached to the base 1244 and that defines an enclosed passage 1248. The wire loop 1246 is formed by a metal single filament wire in this illustrated embodiment but can have other configurations, similar to the loop 516 discussed above. A suture is configured to be seated in the passage 1248 defined by the loop 1246. The suture can be coupled to the loading aid 1242 by a user, which may provide a user of the inserter tool 1200 flexibility in deciding on a size and type of suture to use that is appropriate for a particular patient and a particular surgical procedure and/or may allow for the inserter tool 1200 to be sold without the loading aid 1242 and thus at a lower cost than the inserter tool 1200 sold with the loading aid 1242.

The loading aid 1242 in this illustrated embodiment is configured to be releasably attached to the inserter tool 1200. FIGS. 57 and 58 show the loading aid 1242 releasably attached to the inserter tool 1200. The base 1244 of the loading aid 1242 includes a plurality of clips 1252 configured to releasably clip to the outer shaft 1208 to releasably attach the loading aid 1242 to the inserter tool 1200. The loading aid 1242 includes three clips 1252 in this illustrated embodiment, with two of the clips 1252 clipping to one side of the outer shaft 1208 and a third one of the clips 1252 located between the other two clips 1252 clipped to the other side of the outer shaft 1208, but the loading aid 1242 can include another number of clips 1252.

Figure 59:
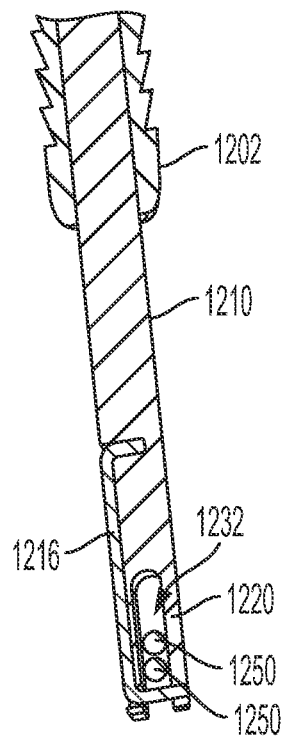
FIG. 59 is a cross-sectional view of the inserter tool of FIG. 52 and a suture extending through an enclosed passage of the inserter tool.

With the suture 1250 extending through the loop 1246 of the loading aid 1242, the loading aid 1242 can be pulled by the base 1244 in the direction of arrow 1254 on the base 1244, e.g., printed thereon, etched therein, adhered thereon as a sticker, etc., to release the clips 1252 from the outer shaft 1208 and to pull the suture 1250 through the enclosed passage 1232 defined by the inner shaft 1210 and the pliable member 1216 so as to thread the suture 1250 through the enclosed passage 1232. A location of the arrow 1254 on the base 1244 indicates to a user where to hold the loading aid 1242 during removal of the loading aid 1242 from the inserter tool to which the loading aid 1242 is coupled. The suture 1250 can then be released from the loading aid 1242 by being removed from the loading aid's passage 1248 defined by the loop 1246. FIG. 59 illustrates a suture 1250 released from the loading aid 1242 and extending through the enclosed passage 1232. The suture 1250 extending through the enclosed passage 1232 can thus be releasably coupled to the inserter tool 1200 and have a U-shape with the inserter tool 1200 in its initial configuration, similar to that discussed above regarding the suture 114 and the inserter 100 of FIG. 2. The suture 1250 is generally configured and used similar to the suture 114 of FIG. 2 and, similar to that discussed above regarding the suture 114, includes two strands in this illustrated embodiment but can include another number of strands.

With the suture 1250 coupled to the inserter tool 1200, and with the loading aid 1242 removed if the loading aid 1242 was used to facilitate suture coupling to the inserter tool 1200, the inserter tool 1200 can be used to insert the suture 1250 and the anchor 1202 into a bone hole. In an exemplary embodiment of using the inserter tool 1200 to insert the suture 1250 and the anchor 1202 into a bone hole, a drill or other bone removal tool is inserted into a patient's body to form the bone hole, similar to that discussed above regarding the inserter 100 of FIG. 1.

The inserter tool 1200 is advanced distally into the body of the patient and positioned with the distal end of the inner shaft 1210 within the bone hole and thus with the enclosed passage 1232 within the bone hole. The suture 1250 that extends through the enclosed passage 1232 is thus positioned in the bone hole before the anchor 1202 is secured in the bone hole. A bottom surface of the bone hole can act as a stop surface that stops distal movement of the inserter tool 1200 relative to the bone, similar to that discussed above regarding the inserter 100 of FIG. 1.

With the distal end of the inner shaft 1210 positioned in the bone hole, and prior to distal advancement of the anchor 1250 relative to the inner shaft 1210, the suture 1250 can be tensioned as desired and can be retained by the suture retention member 1234.

Figure 60:
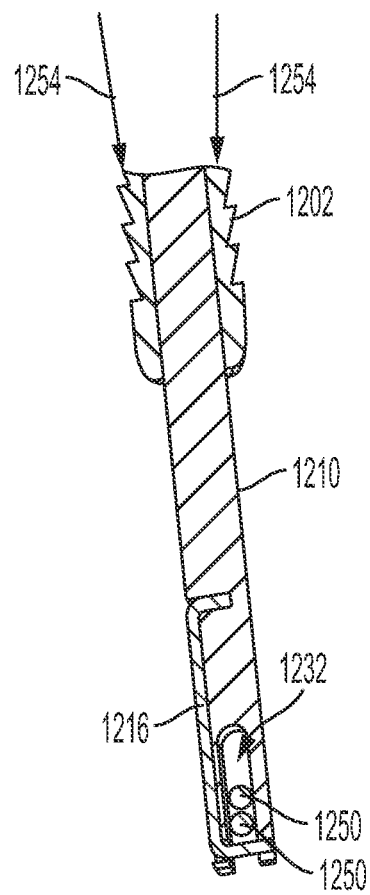
FIG. 60 is a cross-sectional view of the inserter tool of FIG. 59 showing a distal force being applied to an anchor of the inserter tool.
Figure 61:
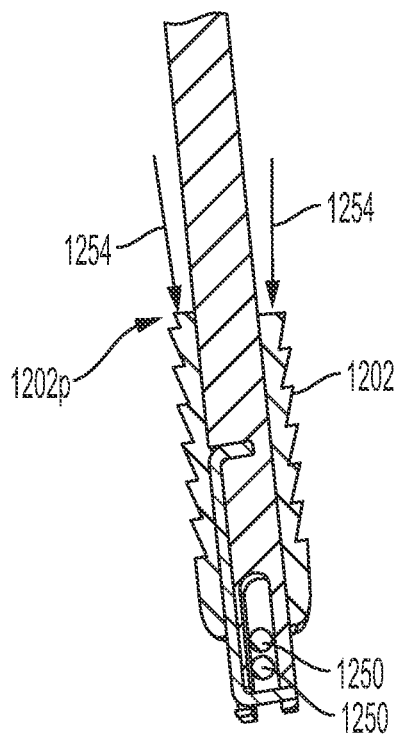
FIG. 61 is a cross-sectional view of the inserter tool of FIG. 60 showing the distal force continued to be applied to the anchor.
Figure 62:
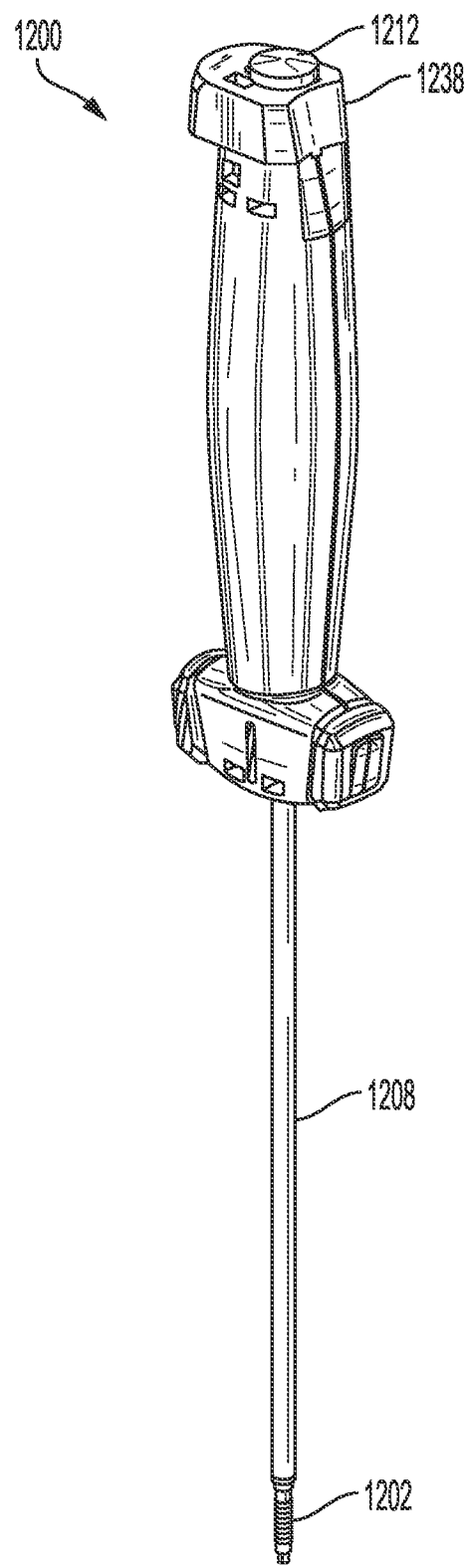
FIG. 62 is a perspective view of the inserter tool of FIG. 61 showing the anchor fully distally advanced after striking of the strike cap of the inserter tool.

With the distal end of the inner shaft 1210 positioned in the bone hole, the locking mechanism 1238 is moved from the locked position to the unlocked position, as discussed above. The outer shaft 1208 is now free to move relative to the inner shaft 1210 in response to a strike on the strike cap 1212. With the distal end of the inner shaft 1210 positioned in the bone hole, the anchor 1202 is advanced distally into the bone hole by longitudinally translating the anchor 1202 relative to the inner shaft 1210 in a distal direction by striking the strike cap 1212 to distally advance the outer shaft 1208, similar to that discussed above regarding the inserter 100 of FIG. 1. The anchor 1202 in the bone hole traps the suture 1250 between the exterior surface of the anchor 1202 and the bone surface defining the bone hole. FIG. 60 shows a distal force (represented by arrows 1254) being applied to the anchor 1202 from the distal movement of the outer shaft 1208 caused by the strike on the strike cap 1212. FIG. 61 shows continued application of the distal force being applied to the anchor 1202 with the anchor 1202 having moved distally from its position in FIG. 60. The outer shaft 1208 abuts a proximal end 1202p of the anchor 1202 in FIG. 61 (and in FIG. 60) but is not shown for clarity of illustration. FIG. 62 shows the anchor 1202 fully advanced distally as caused by the distal, axial translation of the outer shaft 1208, e.g., with the strike cap's distal surface abutting the locking mechanism 1238 as discussed above.

Figure 63:
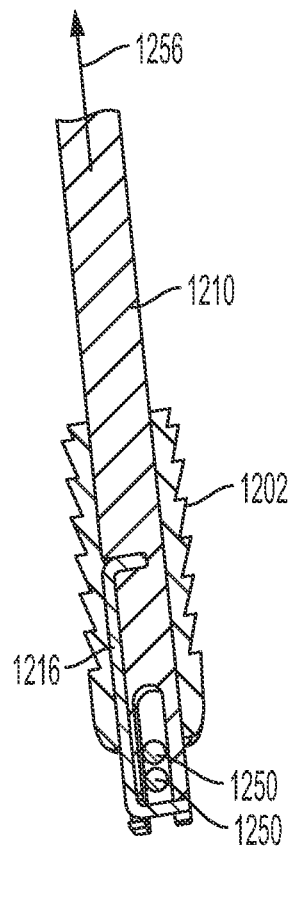
FIG. 63 is a cross-sectional view of the inserter tool of FIG. 62 showing a proximal force being applied to the inserter tool.
Figure 64:
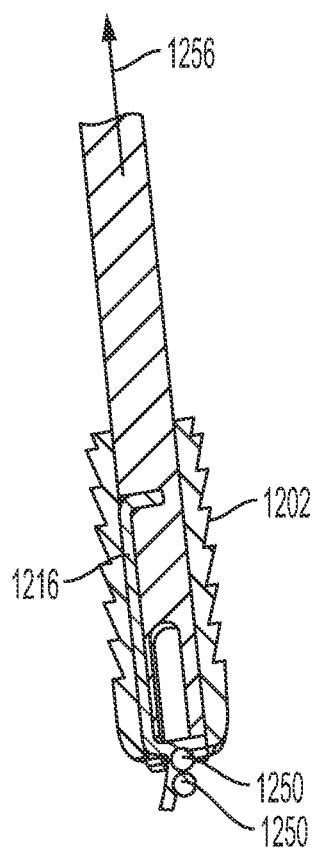
FIG. 64 is a cross-sectional view of the inserter tool of FIG. 63 showing the proximal force continued to be applied to the inserter tool.
Figure 65:
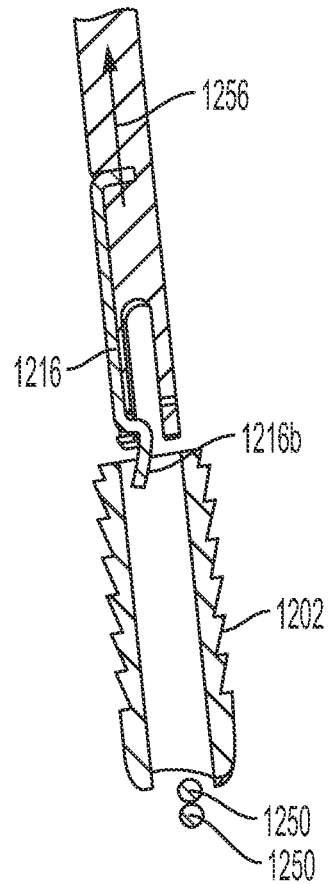
FIG. 65 is a cross-sectional view of the inserter tool of FIG. 64 showing the proximal force continued to be applied to the inserter tool.

After the anchor 1202 has been inserted into the bone hole, the inserter tool 1200 is longitudinally translated in a proximal direction, e.g., pulled axially along a longitudinal axis 1204 of the inserter tool 1200 as shown by an arrow 1256 in FIGS. 63-65, to be removed from the patient's body with the anchor 1202 and the suture 1250 remaining in the bone. The proximal movement of the inserter tool 1200 causes the pliable member 1216 to bend due to the second end 1216b of the pliable member 1216 being free and the first end 1216a of the pliable member 1216 being fixedly attached to the inserter tool 1200. The first end 1216a of the pliable member 1216 attached to the inserter tool 1200 moves proximally with the inserter tool 1200 while pliable member 1216 bends and the free second end 1216b of the pliable member 1216 slides out of the groove 1222 such that the enclosed passage 1232 is open so as to allow exit of the suture 1250 therefrom, as shown in FIG. 64. The cavity 1218 extending substantially perpendicular to the longitudinal axis of the inner shaft 1210 may help prevent the first end 1216a of the pliable member 1216 from being detached from the inner shaft 1210 during proximal movement of the inner shaft 1210 and bending of the pliable member 1216 causes thereby since the pliable member 1216 is bending away from the longitudinal axis of the inner shaft 1210 to open the enclosed passage 1232. Continued proximal movement of the inserter tool 1200 causes the entire pliable member 1216 to exit the patient's body along with the inserter tool 1200. With the enclosed passage 1232 being open, the suture 1250 is freed from the enclosed passage 1232, and thus from the suture retention channel 1204, and can thus stay fixed in position in the bone hole with the anchor 1202, as shown in FIG. 65. Tails of the suture 1250 can be trimmed as desired. Although the suture 1250 is shown distal to the anchor 1202 in FIG. 65, the suture 1250 can be fully or partially located within the anchor 1202, e.g., in embodiments in which the anchor 1202 has an open distal end.

The pliable member 1216 in this illustrated embodiment is passive such that the suture 1250 extends through the enclosed passage 1232 and is freely slidable through the enclosed passage 1232 until the anchor 1202 fixes the suture 1250 in position relative to the bone.

Figure 68:
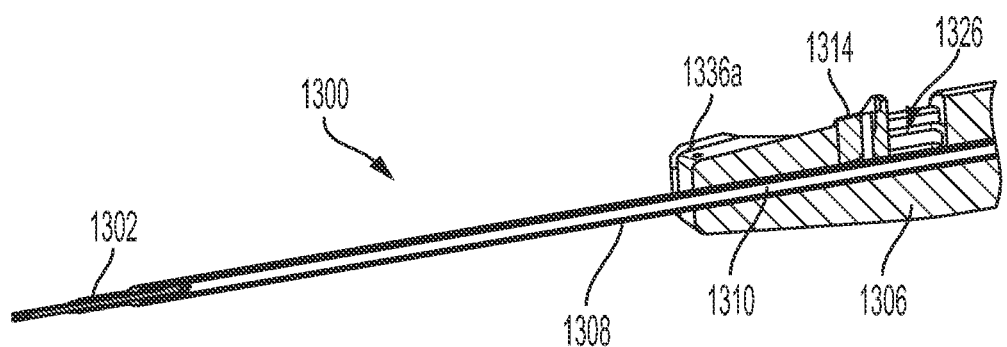
FIG. 68 is a cross-sectional view of the inserter tool of FIG. 66.
Figure 69:
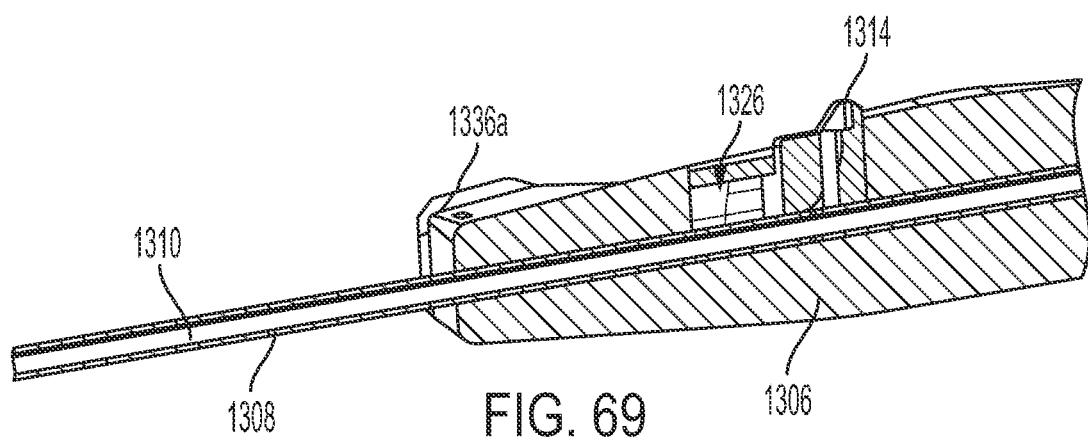
FIG. 69 is a cross-sectional view of a proximal portion of the inserter tool of FIG. 66 after actuation of an actuator of the inserter tool.

FIGS. 66-69 illustrate another embodiment of an inserter tool 1300 for knotless anchor insertion in a soft tissue repair surgical procedure. The inserter tool 1300 is generally configured and used similar to the inserter tool 1200 of FIGS. 49-54, e.g., is configured to insert an anchor 1302 into a bone of a patient to secure a soft tissue relative to the bone and includes a handle 1306, an outer shaft 1308 that extends distally from the handle 1306, an inner shaft 1310 that extends distally from the handle 1306 and includes a notch formed therein that defines a suture retention channel 1304, a pliable member 1316 that cooperates with the inner shaft 1310 to define an enclosed passage 1332, and a suture retention member defined by the handle 1306 and first and second elastomeric cleats (only one of the elastomeric cleats 1336a is shown in FIGS. 68 and 69) fixedly attached to the handle 1306. The anchor 1302 is generally configured and used similar to the anchor 102 of FIG. 1. Although not shown in FIGS. 66-69, the inserter tool 1300 also includes, similar to the inserter tool 1200, a strike cap that extends proximally from the handle 1306 and a locking mechanism configured to lock the outer shaft 1308 in position relative to the inner shaft 1310 when the locking mechanism is in a locked position.

The pliable member 1316 has a first end fixedly attached to the handle 1306 and has a second end that is free so as to not be fixedly attached to the handle 1306. The inner shaft 1310 includes a groove 1322 configured to releasably seat the second end of the pliable member 1316 therein, similar to the groove 1222 that seats the second end 1216a of the pliable member 1216 therein. The first end of the pliable member 1316 is fixedly attached to an actuator 1314 at the handle 1306. The first end of the pliable member 1316 can be attached to the actuator 1314 in any of a variety of ways, similar to that discussed above regarding the first end 1216a of the pliable member 1216 being fixedly attached to the inner shaft 1210.

Figure 66:
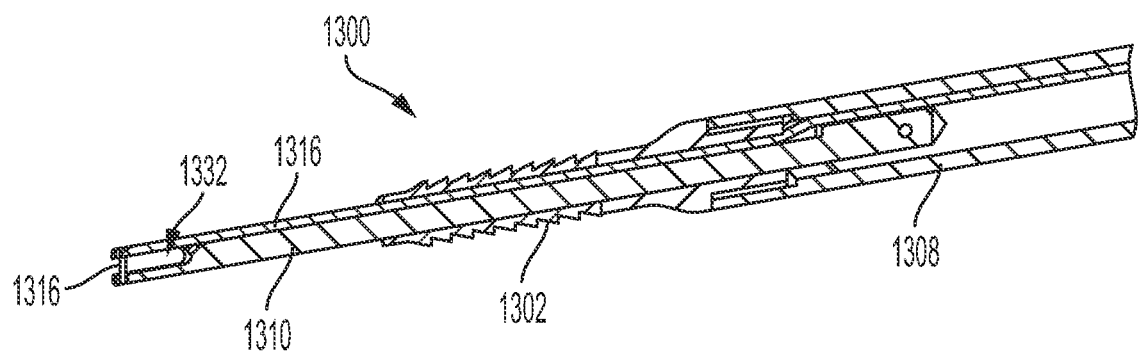
FIG. 66 is a cross-sectional view of a distal portion of another embodiment of an inserter tool.
Figure 67:
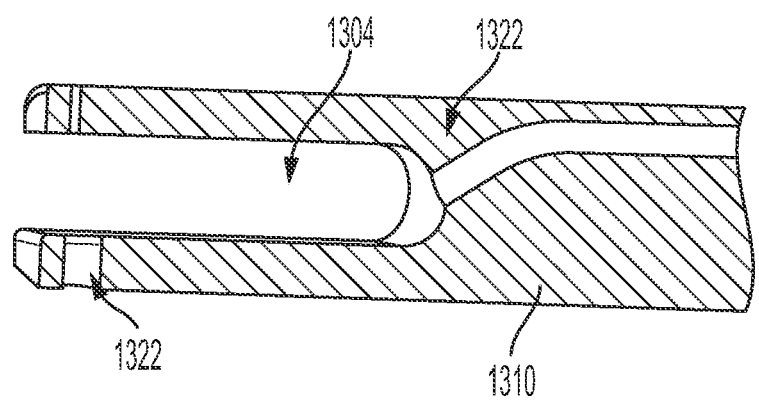
FIG. 67 is a cross-sectional view of a distal portion of an inner shaft of the inserter tool of FIG. 66.

The pliable member 1216 extends from the actuator 1314 to the groove 1322 within an inner lumen of the outer shaft 1308 in which the inner shaft 1310 is disposed, as shown in FIGS. 66 and 68. The inner shaft 1310 includes a longitudinal channel 1320 that extends longitudinally along the inner shaft 1310 that is configured to seat the pliable member 1216 therein. The pliable member 1216 bends to exit the longitudinal channel 1320 to allow the second end of the pliable member 1216 to be seated in the inner shaft's groove 1322.

The pliable member 1216 of the inserter tool 1200 is a passive member, as discussed above. In this illustrated embodiment, the pliable member 1316 is an active member. The pliable member 1316 is configured to be actively moved to open the enclosed passage 1332 using an actuator 1314. Actuation of the actuator 1314 is configured to move the pliable member 1316 to open the enclosed passage 1332. The actuator 1314 is a slidable trigger in this illustrated embodiment but can have other configurations, e.g., a rotatable knob, a pullable lever, etc.

The actuator 1314 is configured to move between an unactuated position and an actuated position. In the unactuated position, shown in FIG. 68, the pliable member 1316 is seated in the groove 1322 of the inner shaft 1310 and the enclosed passage 1332 is present to receive a suture therethrough. The suture can be positioned in the enclosed passage 1332 similar to that discussed above regarding a suture being positioned in the enclosed passage 1232. In the actuated position, shown in FIG. 69, the pliable member 1316 is not seated in the groove 1322 of the inner shaft 1310 and the enclosed passage 1332 is open to allow the suture to exit the suture retention channel of the inner shaft 1310. In some embodiments, the pliable member 1316 is not stiff enough to bend and move back into the groove 1322 if the actuator 1314 is actuated a second time to slide proximally. In other embodiments, the pliable member 1316 has sufficient stiffness to bend and move back into the groove 1322 if the actuator 1314 is actuated a second time to slide proximally.

The handle 1306 includes a channel 1326 configured to slidably seat the actuator 1314 therein. The actuator 1314 is user-accessible outside of the channel 1326. The actuator 1314 is configured to slide proximally within the channel

1326 relative to the handle 1306, the outer shaft 1308, and the inner shaft 1310 from the unactuated position to the actuated position. The proximal movement of the actuator 1314 is configured to cause the pliable member 1316 to move proximally relative to the handle 1306, the outer shaft 1308, and the inner shaft 1310. The proximal movement of the pliable member 1316 causes the second end of the pliable member 1316 to exit the groove 1322 of the inner shaft 1310, thereby opening the enclosed passage 1332.

With the suture coupled to the inserter tool 1300, and with the loading aid removed if a loading aid was used to facilitate suture coupling to the inserter tool 1300, the inserter tool 1300 can be used to insert the suture and the anchor 1302 into a bone hole. In an exemplary embodiment of using the inserter tool 1300 to insert the suture and the anchor 1302 into a bone hole, a drill or other bone removal tool is inserted into a patient's body to form the bone hole, similar to that discussed above regarding the inserter 100 of FIG. 1.

The inserter tool 1300 is advanced distally into the body of the patient and positioned with the distal end of the inner shaft 1310 within the bone hole and thus with the enclosed passage 1332 within the bone hole. The suture that extends through the enclosed passage 1332 is thus positioned in the bone hole before the anchor 1302 is secured in the bone hole. A bottom surface of the bone hole can act as a stop surface that stops distal movement of the inserter tool 1300 relative to the bone, similar to that discussed above regarding the inserter 100 of FIG. 1.

With the distal end of the inner shaft 1310 positioned in the bone hole, and prior to distal advancement of the anchor 1302 relative to the inner shaft 1310, the suture can be tensioned as desired and can be retained by the suture retention member of the inserter tool 1300.

With the distal end of the inner shaft 1310 positioned in the bone hole, the locking mechanism is moved from the locked position to the unlocked position, as discussed above. The outer shaft 1308 is now free to move relative to the inner shaft 1310 in response to a strike on the strike cap. With the distal end of the inner shaft 1310 positioned in the bone hole, the anchor 1302 is advanced distally into the bone hole by longitudinally translating the anchor 1302 relative to the inner shaft 1310 in a distal direction by striking the strike cap to distally advance the outer shaft 1308, similar to that discussed above regarding the inserter 100 of FIG. 1. The anchor 1302 in the bone hole traps the suture between the exterior surface of the anchor 1302 and the bone surface defining the bone hole.

After the anchor 1302 has been inserted into the bone hole, the actuator 1314 is actuated, e.g., slid proximally in the handle's channel 1326, to move the pliable member 1316 and open the enclosed passage 1332. The proximal movement of the actuator 1314 causes the pliable member 1316 to move proximally due to the second end of the pliable member 1316 being free and the first end of the pliable member 1316 being fixedly attached to the actuator 1314. The first end of the pliable member 1316 attached to the actuator 1314 moves proximally with the actuator 1314, and the free second end of the pliable member 1316 slides out of the groove 1322 such that the enclosed passage 1332 is open so as to allow exit of the suture therefrom. With the enclosed passage 1332 being open, the suture is allowed to exit the enclosed passage 1332, and thus also the suture retention channel 1304.

With the enclosed passage 1332 open, e.g., after the actuation of the actuator 1314, the inserter tool 1300 is longitudinally translated in a proximal direction, e.g., pulled axially along a longitudinal axis of the inserter tool 1300, to be removed from the patient's body with the anchor 1302 and the suture remaining in the bone. The proximal movement of the inserter tool 1300 causes the entire pliable member 1316 to exit the patient's body along with the inserter tool 1300. Tails of the suture can be trimmed as desired.

Figure 70:
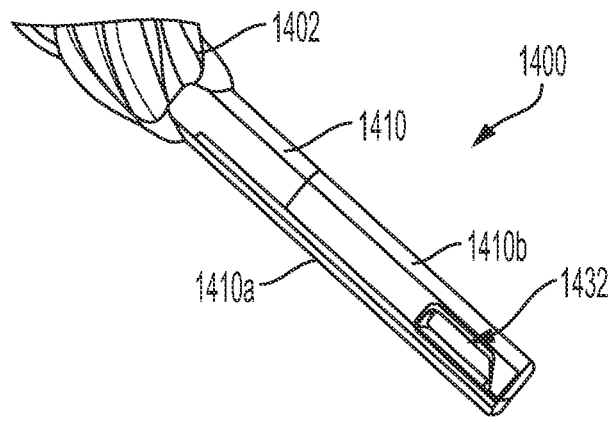
FIG. 70 is a perspective view of a distal portion of yet another embodiment of an inserter tool.
Figure 71:
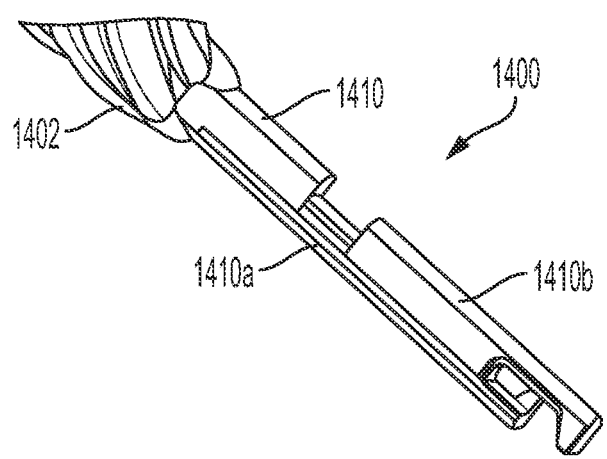
FIG. 71 is a perspective view of the distal portion the inserter tool of FIG. 70 after actuation of an actuator of the inserter tool.

FIGS. 70 and 71 illustrate another embodiment of an inserter tool 1400 for knotless anchor insertion in a soft tissue repair surgical procedure. The inserter tool 1400 is generally configured and used similar to the inserter tool 100 of FIG. 1, e.g., is configured to insert an anchor 1402 into a bone of a patient to secure a soft tissue relative to the bone and includes a handle (not shown), an outer shaft (not shown) that extends distally from the handle, an inner shaft 1410 that extends distally from the handle, a strike cap (not shown) that extends proximally from the handle, a locking mechanism (not shown) configured to lock the outer shaft in position relative to the inner shaft 1410 when the locking mechanism is in a locked position, and a suture retention member (not shown). The anchor 1402 is generally configured and used similar to the anchor 102 of FIG. 1.

In this illustrated embodiment, the inner shaft 1410 includes a first component 1410*a* and a second component 1410*b* that cooperate to define an enclosed passage 1432 that is configured to receive a suture therethrough similar to the enclosed passages discussed above. FIG. 70 shows the first and second components 1410*a*, 1410*b* in an engaged position cooperating to define the enclosed passage 1432. The engaged position is an initial position of the first and second components 1410*a*, 1410*b*. Distal tips of the first and second components 1410*a*, 1410*b* are interlocked in the engaged position, which allows the enclosed passage 1432 to be present. The first and second components 1410*a*, 1410*b* are dovetailed to interlock in this illustrated embodiment but can be interlocked in another way. FIG. 71 shows the first and second components 1410*a*, 1410*b* in a disengaged position in which the enclosed passage 1432 is open. The second component 1410*b* is configured to move relative to the first component 1410*a* to move from the engaged position to the disengaged position.

The inserter tool 1400 includes an actuator (not shown) configured to be actuated to move the second component 1410*b* relative to the first component 1410*a*. The actuator is generally configured and used similar to the actuator 1214 of the inserter tool 1200, e.g., by being a slidable trigger or other actuator. The actuator is configured to move between an unactuated position, corresponding to the engaged position of the first and second components 1410*a*, 1410*b*, and an actuated position, corresponding to the disengaged position of the first and second components 1410*a*, 1410*b*.

With the suture coupled to the inserter tool 1400, and with the loading aid removed if a loading aid was used to facilitate suture coupling to the inserter tool 1400, the inserter tool 1400 can be used to insert the suture and the anchor 1402 into a bone hole. In an exemplary embodiment of using the inserter tool 1400 to insert the suture and the anchor 1402 into a bone hole, a drill or other bone removal tool is inserted into a patient's body to form the bone hole, similar to that discussed above regarding the inserter 100 of FIG. 1.

The inserter tool 1400 is advanced distally into the body of the patient and positioned with the distal end of the inner shaft 1410 within the bone hole and thus with the enclosed passage 1432 within the bone hole. The suture that extends through the enclosed passage 1432 is thus positioned in the bone hole before the anchor 1402 is secured in the bone hole.

A bottom surface of the bone hole can act as a stop surface that stops distal movement of the inserter tool 1400 relative to the bone, similar to that discussed above regarding the inserter 100 of FIG. 1.

With the distal end of the inner shaft 1410 positioned in the bone hole, and prior to distal advancement of the anchor 1402 relative to the inner shaft 1410, the suture can be tensioned as desired and can be retained by the suture retention member of the inserter tool 1400.

With the distal end of the inner shaft 1410 positioned in the bone hole, the locking mechanism is moved from the locked position to the unlocked position, as discussed above. The outer shaft is now free to move relative to the inner shaft 1410 in response to a strike on the strike cap. With the distal end of the inner shaft 1410 positioned in the bone hole, the anchor 1402 is advanced distally into the bone hole by longitudinally translating the anchor 1402 relative to the inner shaft 1410 in a distal direction by striking the strike cap to distally advance the outer shaft, similar to that discussed above regarding the inserter 100 of FIG. 1. The anchor 1402 in the bone hole traps the suture between the exterior surface of the anchor 1402 and the bone surface defining the bone hole.

After the anchor 1402 has been inserted into the bone hole, the actuator is actuated, e.g., slid distally in the handle's channel or otherwise actuated, to move the second component 1410b distally relative to the first component 1410b and thereby open the enclosed passage 1432. With the enclosed passage 1432 being open, the suture is allowed to exit the enclosed passage 1432.

With the enclosed passage 1432 open, e.g., after the actuation of the actuator, the inserter tool 1400 is longitudinally translated in a proximal direction, e.g., pulled axially along a longitudinal axis of the inserter tool 1400, to be removed from the patient's body with the anchor 1402 and the suture remaining in the bone. Tails of the suture can be trimmed as desired.

The inserter tools 100, 500, 600, 700, 800, 900, 1000, 1200, 1300, 1400 discussed above have linear outer and inner shafts but can have curved outer and inner shafts, as mentioned above. Similarly, as also mentioned above, the inserter tool 1100 has curved outer and inner shafts but can have linear outer and inner shafts. FIGS. 72-79 illustrate another embodiment of an inserter tool 1500 having curved outer and inner shafts 1508, 1510.

The inserter tool 1500 is for knotless anchor insertion in a soft tissue repair surgical procedure and is the same as the inserter tool 1200 of FIGS. 49-54 except for the curvature of the outer and inner shafts 1508, 1510 (and an indicator related thereto, discussed below), e.g., is configured to insert the anchor 1202 into a bone of a patient to secure a soft tissue relative to the bone and includes a handle 1506, the outer shaft 1508 that extends distally from the handle 1506, the inner shaft 1510 that extends distally from the handle 1506 and includes a notch formed therein that defines a suture retention channel, a pliable member 1516 that cooperates with the inner shaft 1510 to define an enclosed passage, a suture retention member 1534 defined by the handle 1506 and first and second elastomeric cleats 1536a, 1536b fixedly attached to the handle 1506, a strike cap 1512 that extends proximally from the handle 1506, and a locking mechanism 1538 configured to lock the outer shaft 1508 in position relative to the inner shaft 1510 when the locking mechanism is in a locked position.

The curved outer shaft 1508 in this illustrated embodiment is flexible, unlike the linear outer shaft 1208 of the inserter tool 1200. The outer shaft 1508 being flexible facilitates the outer shaft's translation along the curved inner shaft 1510.

Figure 72:
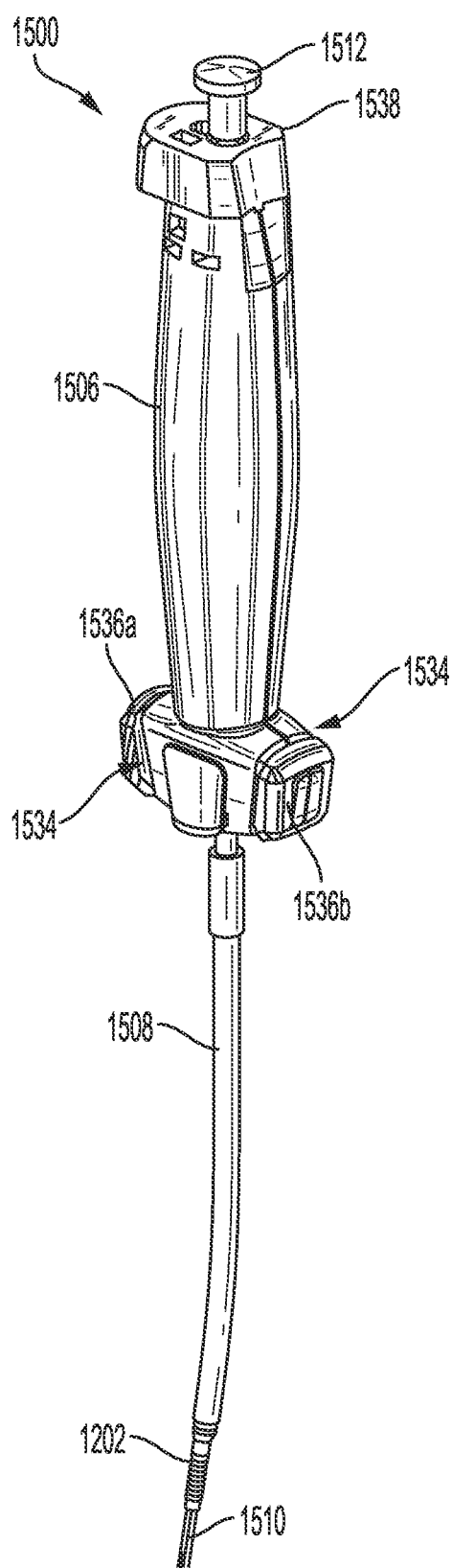
FIG. 72 is a perspective view of still another embodiment of an inserter tool.
Figure 73:
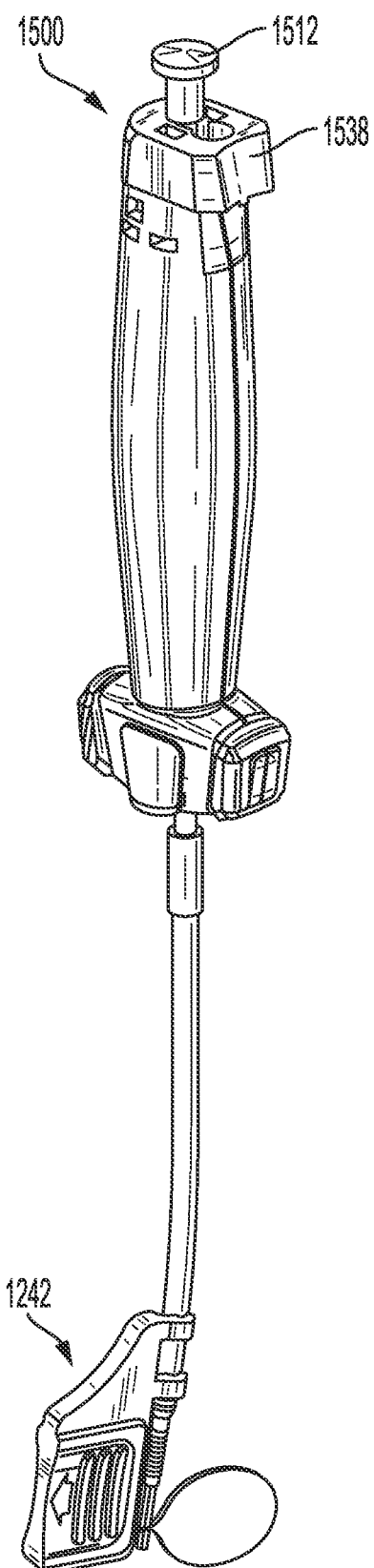
FIG. 73 is another perspective view of the inserter tool of FIG. 72 with a locking mechanism of the inserter tool in a locked position and with the loading aid of FIG. 57 coupled to the inserter tool.
Figure 74:
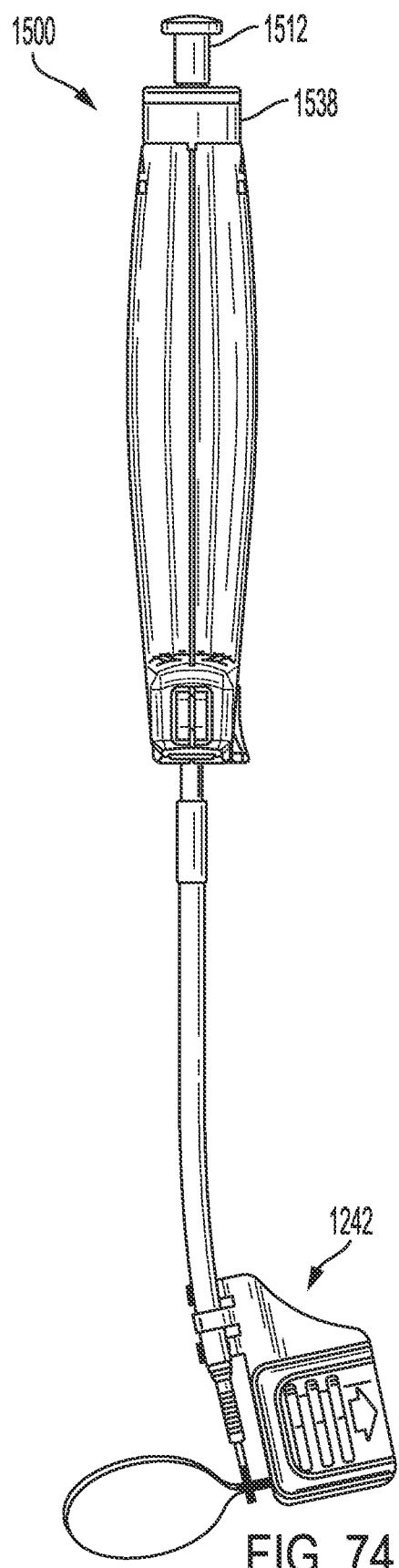
FIG. 74 is another perspective view of the inserter tool and the loading aid of FIG. 73.
Figure 75:
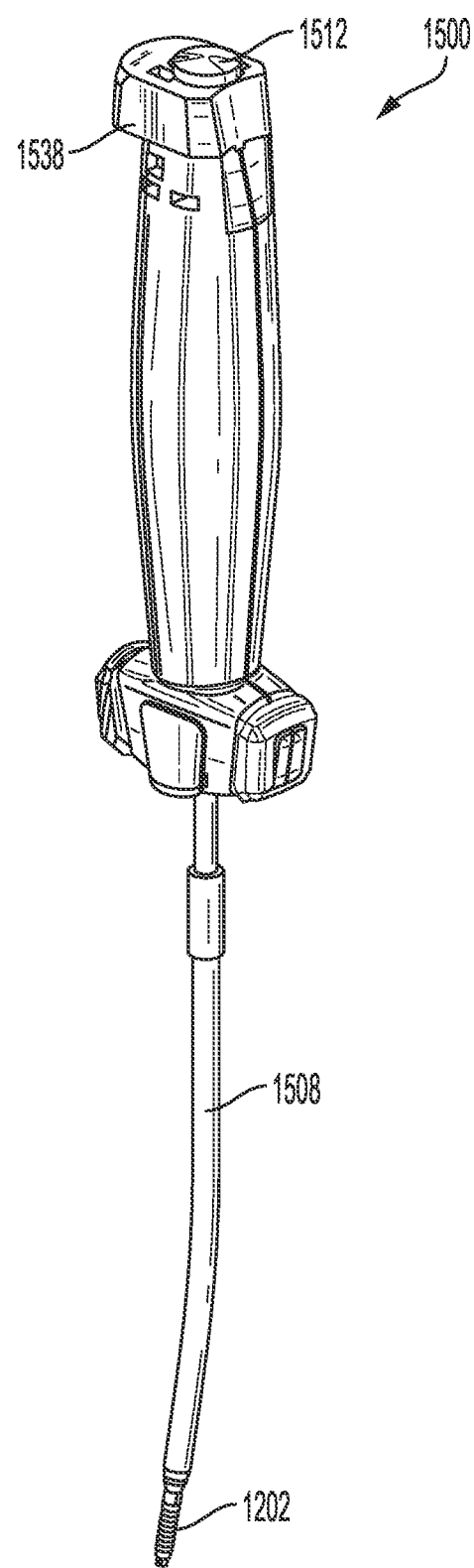
FIG. 75 is a perspective view of the inserter tool of FIG. 72 after striking of a strike cap of the inserter tool.

FIG. 72 is similar to FIG. 49 and shows the locking mechanism 1538 in an unlocked position before the strike cap 1512 has been struck. FIGS. 73 and 74 are similar to FIGS. 57 and 58, respectively, and show the locking mechanism 1538 in a locked position and show the loading aid 1242 releasably attached to the inserter tool 1500. FIG. 75 is similar to FIG. 62 and shows the shows the locking mechanism 1538 in the unlocked position after the strike cap 1512 has been struck.

Figure 76:
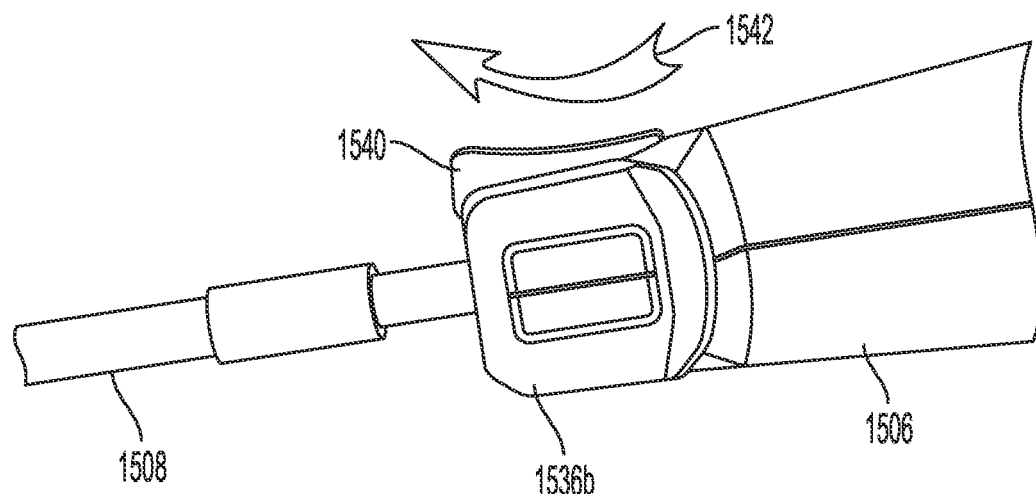
FIG. 76 is a perspective view of an intermediate portion of the inserter tool of FIG. 72.
Figure 77:
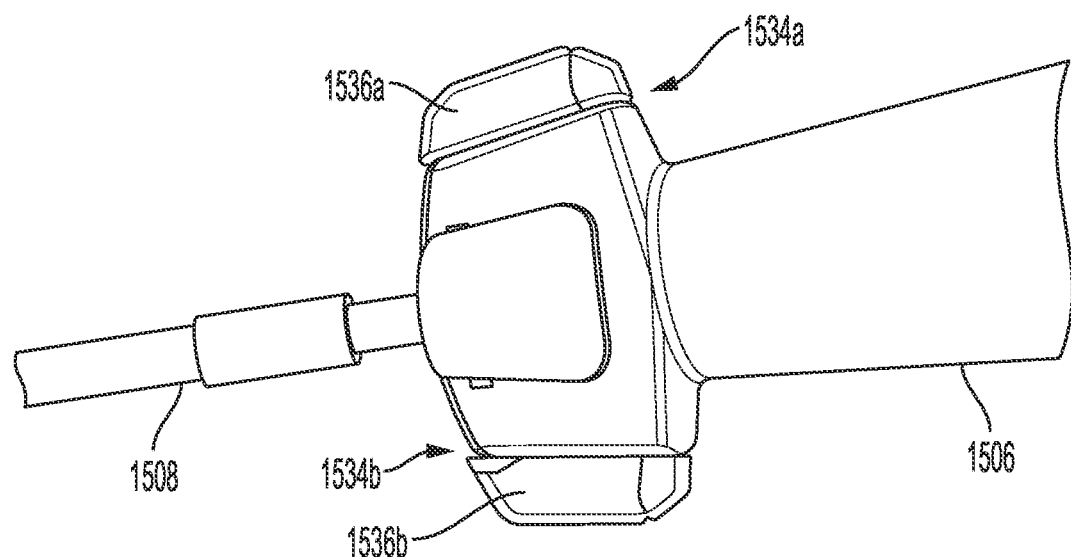
FIG. 77 is another perspective view of the intermediate portion of the inserter tool of FIG. 76.
Figure 78:
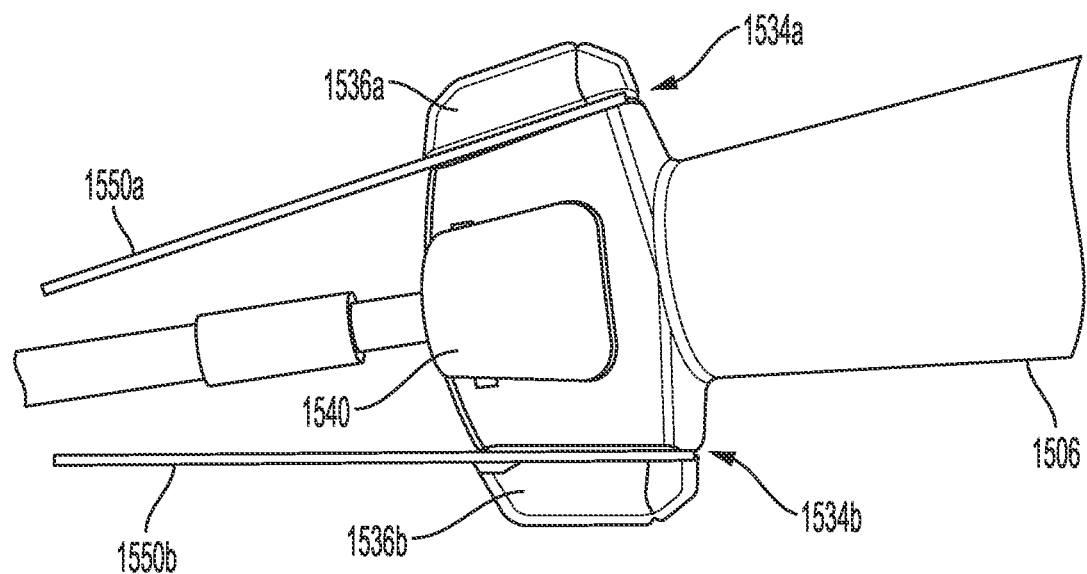
FIG. 78 is a perspective view of the intermediate portion of the inserter tool of FIG. 77 with a suture retained by a suture retention channel of the inserter tool.

FIGS. 76-78 show an indicator 1540 on the handle 1506 includes a fin protruding from the handle 1506 and is curved in a same direction (shown by an arrow 1542) as the outer and inner shafts 1508, 1510. Since the handle 1506 is located outside of a patient's body during use of the inserter tool 1500, the indicator 1540 at the handle 1506 is configured to indicate the direction of the outer and inner shafts' curvature to a user, e.g., in the event that the outer and inner shafts' curvature is not visible within the patient's body. FIG. 78 also shows a first suture 1550a seated in a first suture retention groove 1534a defined by the handle 1506 and the first elastomeric cleat 1536a, and a second suture 1550b seated in a second suture retention groove 1534b defined by the handle 1506 and the second elastomeric cleat 1536b.

Figure 79:
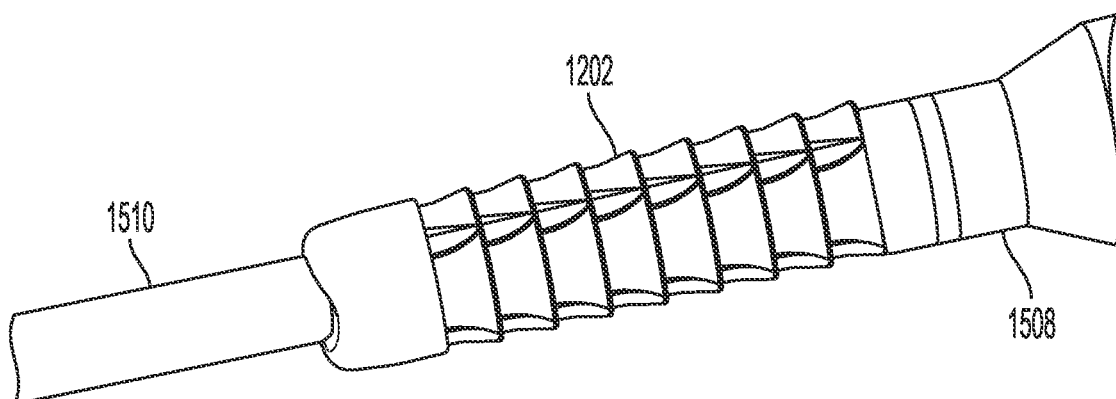
FIG. 79 is another perspective view of an intermediate portion of the inserter tool of FIG. 72.

FIG. 79 shows the outer shaft 1508 abutting the anchor 1202 before the anchor 1202 has been advanced distally into bone.

As mentioned above, any of a variety of anchors can be used with the inserter tools described herein. In an exemplary embodiment, the anchor is a tapered helical anchor. In general, a tapered helical anchor tapers radially inward in a distal direction such that a diameter of the tapered helical anchor at a proximal end of the tapered helical anchor is greater than a diameter of the tapered helical anchor at a distal end of the tapered helical anchor. The tapered helical anchor may thus achieve more cortical bone engagement than cancellous bone engagement, with the increased diameter proximal portion of the tapered helical anchor engaging cortical bone that overlies (is proximal to) cancellous bone. Cortical bone is harder than cancellous bone, so greater engagement of cortical bone than cancellous may better help secure the tapered helical anchor in the bone.

The tapered helical anchor includes a plurality of bone-engaging surface features, e.g., threads or other features. Each of the bone-engaging surface features extends helically along a length of the tapered helical anchor. Each of the bone-engaging surface features is independent from the other of the tapered helical anchor's bone-engaging surface features. Each of the bone-engaging surface features is thus configured to form its own path in bone, which may help minimize unwanted shearing of both cortical and cancellous bone strata. The combination of the distal tapering of the tapered helical anchor and the independent helical bone-engaging surface features allows the tapered helical anchor to progressively engage new areas of bone as the tapered helical anchor is advanced distally into the bone, which may create radial stress through axial displacement and increase fixation of the tapered helical anchor in bone, particularly in cancellous bone that is softer than cortical bone.

In some embodiments each of the tapered helical anchor's bone-engaging surface features can extend along an entire length of the tapered helical anchor. In other embodiments, each of the tapered helical anchor's bone-engaging surface features can extend along only a partial length of the tapered helical anchor such that a proximal portion of the tapered helical anchor includes the bone-engaging surface features, e.g., is threaded, and a distal portion of the tapered helical anchor lacks any threads, e.g., is unthreaded. The distal portion of the tapered helical anchor lacking bone-engaging surface features may facilitate guiding of the tapered helical anchor into a pre-formed bone hole.

The tapered helical anchor is configured to be advanced distally into bone using an inserter tool as described herein, where the inserter tool is configured to longitudinally translate an anchor into bone. The tapered helical anchor can instead, however, be rotationally driven into bone.

FIGS. 80 and 81 illustrate one embodiment of a tapered helical anchor 1600. The tapered helical anchor 1600 includes six helical bone-engaging surface features 1602, in the form of threads, that are independent from one another and that each extend helically around the tapered helical anchor 1600. The threads 1602 each extend along an entire length of the tapered helical anchor 1600. The tapered helical anchor 1600 has rifling for cold-forming the threads 1602. The tapered helical anchor 1600 tapers radially inward in a distal direction such that a diameter of the tapered helical anchor 1600 at a proximal end 1604 of the tapered helical anchor 1600 is greater than a diameter of the tapered helical anchor 1600 at a distal end 1606 of the tapered helical anchor 1600. The tapered helical anchor 1600 is cannulated.

FIGS. 82 and 83 illustrate another embodiment of a tapered helical anchor 1700. The tapered helical anchor 1700 includes six helical bone-engaging surface features 1702, in the form of threads, that are independent from one another and that each extend helically around the tapered helical anchor 1700. The threads 1702 each extend along an entire length of the tapered helical anchor 1700. The threads 1702 have greater depth than the threads 1602 of FIGS. 80 and 81. The tapered helical anchor 1700 has rifling for cold-forming the threads 1702. The tapered helical anchor 1700 tapers radially inward in a distal direction such that a diameter of the tapered helical anchor at a proximal end 1704 of the tapered helical anchor 1700 is greater than a diameter of the tapered helical anchor at a distal end 1706 of the tapered helical anchor 1700. The tapered helical anchor 1700 is cannulated.

FIGS. 84 and 85 illustrate another embodiment of a tapered helical anchor 1800. The tapered helical anchor 1800 includes nine helical bone-engaging surface features 1802, in the form of threads, that are independent from one another and that each extend helically around the tapered helical anchor 1800. The threads 1802 each extend along an entire length of the tapered helical anchor 1800. The threads 1802 have a higher pitch than the threads 1602 of FIGS. 80 and 81. The threads 1802 have a same depth as the threads 1602 of FIGS. 80 and 81. The tapered helical anchor 1800 has rifling for cold-forming the threads 1802. The tapered helical anchor 1800 tapers radially inward in a distal direction such that a diameter of the tapered helical anchor at a proximal end 1804 of the tapered helical anchor 1800 is greater than a diameter of the tapered helical anchor at a distal end 1806 of the tapered helical anchor 1800. The tapered helical anchor 1800 is cannulated.

FIGS. 86 and 87 illustrate another embodiment of a tapered helical anchor 1900. The tapered helical anchor 1900 includes nine helical bone-engaging surface features 1902, in the form of threads, that are independent from one another and that each extend helically around the tapered helical anchor 1900. The threads 1902 each extend along an entire length of the tapered helical anchor 1900. The threads 1902 have a higher pitch than the threads 1702 of FIGS. 82 and 83. The threads 1902 have a same depth as the threads 1702 of FIGS. 82 and 83. The tapered helical anchor 1900 has rifling for cold-forming the threads 1902. The tapered helical anchor 1900 tapers radially inward in a distal direction such that a diameter of the tapered helical anchor at a proximal end 1904 of the tapered helical anchor 1900 is greater than a diameter of the tapered helical anchor at a distal end 1906 of the tapered helical anchor 1900. The tapered helical anchor 1900 is cannulated.

FIGS. 88 and 89 illustrate another embodiment of a tapered helical anchor 2000. The tapered helical anchor 2000 includes six helical bone-engaging surface features 2002, in the form of threads, that are independent from one another and that each extend helically around the tapered helical anchor 2000. The threads 2002 each extend along an entire length of the tapered helical anchor 2000. The tapered helical anchor 2000 includes omnidirectional cutaways along each of the threads 2002 such that the threads 2002 are discontinuous, unlike the threads 1602, 1702, 1802, 1902 that are continuous. The omnidirectional cutaways are configured to allow the threads 2002 to each repeatedly positive engage bone, which may improve fixation of the tapered helical anchor 2002 in the bone. The tapered helical anchor 2000 tapers radially inward in a distal direction such that a diameter of the tapered helical anchor at a proximal end 2004 of the tapered helical anchor 2000 is greater than a diameter of the tapered helical anchor at a distal end 2006 of the tapered helical anchor 2000. The tapered helical anchor 2000 is cannulated.

FIGS. 90 and 91 illustrate another embodiment of a tapered helical anchor 2100. The tapered helical anchor 2100 includes six helical bone-engaging surface features 2102, in the form of threads, that are independent from one another and that each extend helically around the tapered helical anchor 2100. The threads 2102 each extend along a partial length of the tapered helical anchor 2100 such that a proximal portion of the tapered helical anchor 2100 is threaded and a distal portion of the tapered helical anchor 2100 is unthreaded. The tapered helical anchor 2100 tapers radially inward in a distal direction such that a diameter of the tapered helical anchor at a proximal end 2104 of the tapered helical anchor 2100 is greater than a diameter of the tapered helical anchor at a distal end 2106 of the tapered helical anchor 2100. The tapered helical anchor 2100 is cannulated.

FIG. 92 illustrates another embodiment of a tapered helical anchor 2200. The tapered helical anchor 2200 includes six helical bone-engaging surface features 2202, in the form of threads, that are independent from one another and that each extend helically around the tapered helical anchor 2200. The threads 2202 each extend along a partial length of the tapered helical anchor 2200 such that a proximal portion of the tapered helical anchor 2200 is threaded and a distal portion of the tapered helical anchor 2200 is unthreaded. The unthreaded distal portion of the tapered helical anchor 2200 is forked with a pair of distal arms 2208 extending distally from the threaded proximal portion of the tapered helical anchor 2200. The distal arms 2208 are configured to each penetrate into bone, e.g., at a distal bottom of a bone hole in which the tapered distal anchor 2200 is disposed, which may help fix the tapered helical anchor 2200 in the bone. The tapered helical anchor 2200 tapers radially inward in a distal direction such that a diameter of the tapered helical anchor at a proximal end 2204 of the tapered helical anchor 2200 is greater than a diameter of the tapered helical anchor at a distal end 2206 of the tapered helical anchor 2200. The tapered helical anchor 2200 is cannulated.

FIG. 92 shows the tapered helical anchor 2200 as a standalone element. FIG. 93 shows the tapered helical anchor 2200 releasably coupled to the inserter tool 100 of FIG. 1 at an initial position, e.g., before the outer shaft 108 has distally advanced the tapered helical anchor 2200. FIG. 94 shows the tapered helical anchor 220 after the outer shaft 108 has distally advanced the tapered helical anchor 2200 and before the inserter tool 100 is moved proximally relative to the tapered helical anchor 2200. Although FIGS. 93 and 94 show the tapered helical anchor 2200 used with the inserter tool 100 of FIG. 1, the tapered helical anchor 2200 can, as mentioned above, be used with another inserter tool.

The devices disclosed herein can be designed to be disposed of after a single use, or they can be designed to be used multiple times. In either case, however, a device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation or toxic gas that can penetrate the container, such as Ethylene Oxide, gamma radiation, x-rays, or high-energy electrons. The radiation kills bacteria on the instrument and in the container. The sterilized instrument can then be stored in the sterile container. The sealed container keeps the instrument sterile until it is opened in a medical facility.

Sterilization can be done by any number of ways known to those skilled in the art including beta or gamma radiation, ethylene oxide, steam, and a liquid bath (e.g., cold soak).

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety for all purposes.

What is claimed is:

1. A surgical system, comprising:
   a handle;
   an outer shaft extending distally from the handle and including an inner lumen;
   an inner shaft extending distally from the handle, the inner shaft being positioned in the inner lumen of the outer shaft, a distal end of the inner shaft being positioned distal to an open distal end of the outer shaft, and the distal end of the inner shaft having a notch formed therein that is configured to seat a suture therein, the inner shaft including a pair of distal arms that define the notch therebetween, wherein the notch has an open distal end and a closed proximal end, the distal arms being configured to move radially outward from a resting configuration to an expanded configuration, the distal arms being biased to the resting configuration, and the distal arms being in the expanded configuration allows the suture to be released from the notch; a pliable member that is a separate and distinct member from the inner shaft and that extends along the open distal end of the notch so as to define an enclosed passage in cooperation; and an anchor configured to be implanted in bone, the anchor including an inner lumen, and the inner shaft being positioned in the inner lumen of the anchor;
   wherein, with the distal end of the inner shaft positioned in a bone hole, the outer shaft is configured to translate longitudinally and distally relative to the inner shaft and thereby cause the anchor to translate longitudinally and distally into the bone hole.

2. The system of claim 1, wherein, after the translation of the outer shaft, the outer shaft and the inner shaft are configured to simultaneously translate longitudinally and proximally relative to the anchor in the bone hole.

3. The system of claim 1, wherein, prior to the translation of the outer shaft, the distal end of the outer shaft abuts a proximal end of the anchor having the inner shaft positioned in the inner lumen of the anchor.

4. The system of claim 1, wherein the pliable member is configured to bend such that the enclosed passage is opened to allow the suture to be released.

5. The system of claim 1, further comprising the suture seated in the notch.

6. The system of claim 5, wherein the suture is seated in the notch prior to the distal end of the inner shaft being positioned in the bone hole and is seated in the notch after the translation of the outer shaft such that the anchor traps the suture between an exterior surface of the anchor and a wall of the bone hole.

7. The system of claim 5, further comprising a suture retention member at the handle, the suture retention member being configured to releasably retain the suture therein.

8. The system of claim 1, further comprising a locking mechanism configured to move from a locked position, in which the outer shaft is prevented from translating longitudinally and distally relative to the inner shaft, to an unlocked position, in which the outer shaft is allowed to translate longitudinally and distally relative to the inner shaft.

9. The system of claim 1, further comprising a strike cap extending proximally from the handle and being operatively coupled to the outer shaft, the strike cap being configured to be hit by a tool and thereby cause the outer shaft to translate longitudinally and distally relative to the inner shaft.

10. The system of claim 1, further comprising the suture and a loading aid;
    wherein the loading aid is configured to releasably couple to the inner shaft and is configured to guide the suture into the notch.

11. A surgical system, comprising:
    an inserter tool comprising:
       an outer shaft, and
       an inner shaft, a distal end of the inner shaft having a suture retention channel formed therein, and the inner shaft being positioned in the outer shaft with the suture retention channel positioned distal to an open distal end of the outer shaft;
a suture seated in the suture retention channel; and
an anchor configured to be implanted in bone and having the inner shaft seated in a cannulated interior thereof, the anchor being configured to be pushed distally by the outer shaft moving axially and distally along a longitudinal axis of the inserter tool relative to the inner shaft and the suture;
wherein, after the axial movement of the outer shaft, the outer shaft and the inner shaft are configured to simultaneously move axially and proximally along the longitudinal axis of the inserter tool relative to the anchor and the suture and thereby automatically cause the suture to exit the suture retention channel;
a pliable member that is a separate and distinct member from the inner shaft, located at a distal end of the suture retention channel, wherein a first end of the pliable member is fixedly attached to the inserter tool, and a second end of the pliable member is configured to be freely movable relative to the inserter tool; and
the simultaneous movement of the outer shaft and the inner shaft is configured to cause the pliable member to automatically bend to allow the suture to exit the suture retention channel.

12. The system of claim 11, wherein, prior to the axial movement of the outer shaft, the distal end of the outer shaft abuts a proximal end of the anchor having the inner shaft positioned therein.

13. The system of claim 11, wherein the distal end of the suture retention channel is open, and the suture retention channel has a closed proximal end.

14. The system of claim 13, wherein the pliable member extends along the open distal end of the suture retention channel so as to define an enclosed passage in cooperation with the inner shaft, the enclosed passage being configured to seat the suture therethrough.

15. The system of claim 14, wherein the simultaneous movement of the outer shaft and the inner shaft is configured to cause the pliable member to automatically bend such that the enclosed passage is opened to allow the suture to exit the suture retention channel.

16. The system of claim 11, wherein the inner shaft includes a pair of distal arms that define the suture retention channel therebetween.

17. The system of claim 11, wherein the inserter tool further comprises a handle, the outer and inner shafts extending distally from the handle.

18. The system of claim 17, further comprising a suture retention member at the handle, the suture retention member being configured to releasably retain the suture therein.

19. The system of claim 11, wherein the inserter tool further comprises a locking mechanism configured to move from a locked position, in which the outer shaft is prevented from moving axially and distally relative to the inner shaft, to an unlocked position, in which the outer shaft is allowed to move axially and distally relative to the inner shaft.

20. The system of claim 11, wherein the inserter tool further comprises a strike cap operatively coupled to the outer shaft, the strike cap being configured to be hit by a tool and thereby cause the outer shaft to move axially and distally relative to the inner shaft.

21. The system of claim 11, further comprising a loading aid configured to releasably couple to the inner shaft and configured to guide the suture into the suture retention channel.

22. The system of claim 16, wherein the simultaneous movement of the outer shaft and the inner shaft is configured to cause the distal arms to automatically move apart from one another to allow the suture to exit the suture retention channel.

23. The system of claim 16, wherein the suture retention channel has a narrower diameter in a distal portion of the suture retention channel defined by the distal arms than in a proximal portion of the suture retention channel defined by the distal arms.

24. The system of claim 6, wherein, after the translation of the outer shaft, the outer shaft and the inner shaft are configured to simultaneously translate proximally relative to the anchor and the suture and thereby automatically cause the suture to be released from the notch.

25. The system of claim 24, wherein the distal arms are configured to automatically move from the resting configuration to the expanded configuration in response to the simultaneous proximal translation of the outer shaft and the inner shaft.

26. The system of claim 24,
wherein, in response to the simultaneous proximal translation of the outer shaft and the inner shaft, the pliable member is configured to bend relative to the distal arms to allow the suture to be released from the notch.

* * * * *